United States Patent
Bonnert et al.

(10) Patent No.: US 6,297,232 B1
(45) Date of Patent: Oct. 2, 2001

(54) TRIAZOLO[4,5-D]PYRIMIDINYL DERIVATIVES AND THEIR USE AS MEDICAMENTS

(75) Inventors: Roger Victor Bonnert, Hoton; Anthony Howard Ingall; Brian Springthorpe, both of Loughborough; Paul Andrew Willis, West Bridgford, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/011,992

(22) PCT Filed: Dec. 12, 1997

(86) PCT No.: PCT/SE97/02091

§ 371 Date: Feb. 19, 1999

§ 102(e) Date: Feb. 19, 1999

(87) PCT Pub. No.: WO98/28300

PCT Pub. Date: Jul. 2, 1998

(30) Foreign Application Priority Data

Dec. 20, 1996 (SE) .................................................. 9604787
Dec. 20, 1996 (SE) .................................................. 9604788

(51) Int. Cl.[7] ............................ A01N 43/00; A61K 38/28

(52) U.S. Cl. .............................. 514/211.03; 514/212.08; 514/228.8; 514/258; 540/488; 540/524; 544/63; 544/254

(58) Field of Search ..................................... 540/488, 524; 544/63, 254; 514/211, 212, 228.8, 258, 211.03, 212.08

(56) References Cited

U.S. PATENT DOCUMENTS 5,747,496 * 5/1998 Cox et al. ............................ 514/258

FOREIGN PATENT DOCUMENTS 0 215 759 A1   3/1987  (EP) .
0 368 640 A2   5/1990  (EP) .
97/03084       1/1997  (WO) .

OTHER PUBLICATIONS

Williams et al., Ann Reports Med. Chem. 31, pp. 21–30, 1996.*

* cited by examiner

*Primary Examiner*—Mukund J. Shah
*Assistant Examiner*—Thomas C. McKenzie
(74) *Attorney, Agent, or Firm*—Nixon & Vanderhye

(57) ABSTRACT

The invention relates to triazolo[4,5-d]pyrimidin-3-yl derivatives which are useful in the treatment of platelet aggregation disorders.

14 Claims, No Drawings

TRIAZOLO[4,5-D]PYRIMIDINYL DERIVATIVES AND THEIR USE AS MEDICAMENTS

The present invention provides new triazolo[4,5-d] pyrimidine compounds, their use as medicaments, compositions containing them and processes for their preparation.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty is also compromised by platelet mediated occlusion or re-occlusion.

A number of converging pathways lead to platelet aggregation. Whatever the initial stimulus, the final common event is a cross linking of platelets by binding of fibrinogen to a membrane binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp.1638–1642).

It has been found that ADP acts as a key mediator of thrombosis. A pivotal role for ADP is supported by the fact that other agents, such as adrenaline and 5-hydroxytryptamine (SHT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81–106; Antiplatelet Trialists' Collaboration (1994), *Br. Med. J.* 308, pp.159–168). Aspirin has no effect on aggregation produced by other sources of ADP, such as damaged cells or ADP released under conditions of turbulent blood flow. ADP-induced platelet aggregation is mediated by the $P_{2T}$-receptor subtype uniquely located on the platelet membrane. Recently it has been shown that antagonists at this receptor offer significant improvements over other anti-thrombotic agents. Accordingly there is a need to find $P_{2T}$-antagonists as anti-thrombotic agents.

It has now been found that a series of triazolo[4,5-d] pyrimidine derivatives are $P_{2T}$-receptor antagonists. In a first aspect the invention therefore provides a compound of formula (I):

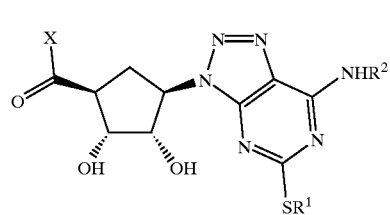

wherein;

X is OH or $NHR^3$;

$R^1$ is $C_{1-6}$-alkyl, $C_{3-8}$-cycloalkyl or a phenyl group, each group being optionally substituted by one or more halogen atoms and/or $OR^4$, $NR^4R^5$, $C_{1-6}$-thioalkyl and/or $C_{1-6}$-alkyl (itself optionally substituted by one or more halogen atoms);

$R^2$ is $C_{1-8}$-alkyl or $C_{2-8}$-alkenyl each of which is optionally substituted by one or more halogen atoms and/or $OR^4$, $NR^4R^5$, $C_{1-6}$-thioalkyl, $C_{3-8}$-cycloalkyl, aryl and/or $C_{1-6}$-alkyl groups; or $R^2$ is a $C_{3-8}$-cycloalkyl group optionally substituted by one or more halogen atoms and/or $OR^4$, $NR^4R^5$, $C_{1-6}$-thioalkyl, phenyl and/or $C_{1-6}$-alkyl groups; the optional phenyl substituent being further optionally substituted by one or more halogen atoms and/or $NO_2$, $C(O)R^4$, $OR^4$, $NR^4R^5$, $C_{1-6}$-thioalkyl and/or $C_{1-6}$-alkyl groups;

$R^3$ is hydrogen or $C_{1-6}$-alkyl substituted by one or more hydroxy and/or phenyl groups and optionally by one or more halogen atoms, wherein the phenyl group is substituted by one or more hydroxy groups and optionally substituted by one or more halogen atoms and/or $NO_2$, $C(O)R^4$, $OR^4$, $NR^4R^5$, $C_{1-6}$-thioalkyl and/or $C_{1-6}$-alkyl groups, or $R^3$ is a $C_{1-6}$-alkyl group substituted by a $C(O)NR^4R^5$ or a COOH group and optionally by one or more halogen atoms and/or $OR^4$, $C(NH)NR^4R^5$, $C(O)NR^4R^5$, phenyl and/or $C_{1-6}$-alkyl groups, wherein the alkyl group is optionally substituted by one or more hydroxy and/or phenyl groups and wherein the phenyl group is optionally substituted as defined above for $R^3$; or $R^3$ is a lactam ring of formula (i):

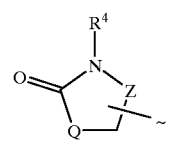

wherein Q is a $(CH_2)_m$ moiety wherein m is 1, 2 or 3, Z is O, C(O) or $CH_2$;

$R^4$ and $R^5$ each independently represent hydrogen, phenyl or a $C_{1-6}$-alkyl wherein the alkyl group is optionally substituted by one or more phenyl groups;

or a salt thereof.

Alkyl groups, whether alone or as part of another group, can be straight chained or branched.

Suitably $R^1$ is $C_{1-6}$-alkyl, $C_{3-8}$-cycloalkyl or a phenyl group, each group being optionally substituted by one or more halogen atoms and/or $OR^4$, $NR^4R^5$, $C_{1-6}$-thioalkyl and/or $C_{1-6}$-alkyl (itself optionally substituted by one or more halogen atoms). Preferably $R^1$ is $C_{1-4}$-alkyl, $C_{4-8}$-cycloalkyl or a phenyl group optionally substituted by one or more halogen atoms or by a $CF_3$ group. More preferably $R^1$ is propyl, cyclohexyl or phenyl optionally substituted by two chlorine atoms or by a CF3 group. Most preferably $R^1$ is propyl or phenyl substituted in the 4-position by $CF_3$.

Suitably $R^2$ is $C_{1-8}$-alkyl or $C_{2-8}$-alkenyl each of which is optionally substituted by one or more halogen atoms and/or $OR^4$, $NR^4R^5$, $C_{1-6}$-thioalkyl, $C_{3-8}$-cycloalkyl, aryl and/or $C_{1-6}$-alkyl groups; or $R^2$ is a $C_{3-8}$-cycloalkyl group optionally substituted by one or more halogen atoms and/or $OR^4$, $NR^4R^5$, $C_{1-6}$-thioalkyl, phenyl and/or $C_{1-6}$-alkyl groups; the optional phenyl substituent being further optionally substituted by one or more halogen atoms and/or $NO_2$, $C(O)R^4$, $OR^4$, $NR^4R^5$, $C_{1-6}$-thioalkyl and/or $C_{1-6}$-alkyl groups. By the term 'aryl' is meant phenyl and naphthyl. Preferably $R^2$ is $C_{1-6}$-alkyl optionally substituted by phenyl or $C_{1-6}$-thioalkyl or $R^2$ is a $C_{3-8}$-cycloalkyl group optionally substituted by phenyl. Most preferably $R^2$ is butyl or 2-phenylcyclopropyl.

Suitably X is OH or $NHR^3$ where $R^3$ is hydrogen or $C_{1-6}$-alkyl substituted by one or more hydroxy and/or phenyl groups and optionally by one or more halogen atoms, wherein the phenyl group is substituted by one or more hydroxy groups and optionally substituted by one or more halogen atoms and/or $NO_2$, $C(O)R^4$, $OR^4$, $NR^4R^5$, $C_{1-6}$-thioalkyl and/or $C_{1-6}$-alkyl groups, or $R^3$ is a $C_{1-6}$-alkyl group substituted by a $C(O)NR^4R^5$ or a COOH group and optionally by one or more halogen atoms and/or $OR^4$, $C(NH)NR^4R^5$, $C(O)NR^4R^5$. phenyl and/or $C_{1-6}$-alkyl groups, wherein the alkyl group is optionally substituted by one or more hydroxy and/or phenyl groups and wherein the phenyl group is optionally substituted as defined above, or $R^3$ is a lactam ring of formula (i).

Preferably $R^3$ is hydrogen or $C_{1-6}$-alkyl substituted by hydroxy and optionally by $C(O)NH_2$ or di-fluoro; $C_{1-6}$-alkyl substituted by $C(O)NH_2$; $C_{1-6}$-alkyl substituted by $C(O)NHMe$; $C_{1-6}$-alkyl substituted by hydroxyphenyl and optionally by $C(O)NR^4R^5$ or $R^3$ is a lactam ring of formula:

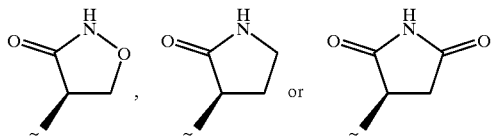

Most preferably $R^3$ is hydrogen.

Particularly preferred compounds of the invention include those exemplified herein, both in free base form and as pharmaceutically acceptable salts thereof.

According to the invention there is further provided a process for the preparation of a compound of formula (I) which comprises (a) deprotecting a compound of formula (II):

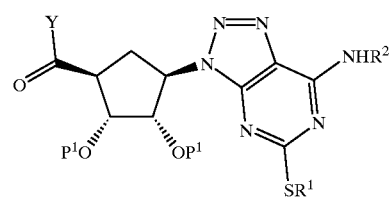

wherein $R^1$ and $R^2$ are as defined above, $P^1$ is a protecting group and Y is X as defined above or $O-C_{1-6}$-alkyl, O-benzyl or NHR wherein R is a $C_{1-6}$-alkyl group substituted by a $C(O)OR^8$ group and optionally one or more halogen atoms and/or $OR^4$, $C(NH)NR^4R^5$, $C(O)NR^4R^5$, phenyl and/or $C_{1-6}$-alkyl groups, wherein $R^4$ and $R^5$ are as defined above and $R^8$ is $C_{1-6}$-alkyl (for example methyl, ethyl, isopropyl or t-butyl) or benzyl; and, optionally (b) reacting the compound of formula (I) thus obtained with a suitable acid or base to prepare a pharmaceutically acceptable salt.

The invention further provides an intermediate of formula (II) wherein its substituents are as defined above. Examples of suitable groups which each $P^1$ may independently represent are a $C_{1-6}$-alkyl (preferably methyl), benzyl, $(C_{1-6}$-alkyl$)_3$Si (preferably trimethylsilyl) and a $C(O)C_{1-6}$-alkyl group (preferably acetyl). Preferably the two groups $P^1$ together with the atoms to which they are attached complete a ring, for example the two groups $P^1$ together represent an alkylidene such as methylidene or, more preferably, isopropylidene, or an alkoxy methylidene such as ethoxymethylidene.

The deprotection reaction in step (a) of the process of the invention may be carried out using methods generally known in the art. Step (a) is preferably carried out as follows:

(i) where one or both of $P^1$ represent $C(O)C_{1-6}$-alkyl, where Y is $O-C_{1-6}$-alkyl and/or where Y is $NHR^7$ and $R^8$ is $C_{1-6}$-alkyl, $C(O)C_{1-6}$-alkyl or $C_{1-6}$-alkyl groups can be removed by basic hydrolysis, for example by using a metal hydroxide, preferably an alkali metal hydroxide, such as sodium hydroxide or lithium hydroxide, or quaternary ammonium hydroxide in a solvent, such as aqueous ethanol or aqueous tetrahydrofuran, at a temperature of from 10 to 100° C., preferably the temperature is around room temperature; or by acidic hydrolysis using a mineral acid such as HCl or a strong organic acid such as trichloroacetic acid in a solvent such as aqueous 1,4-dioxane;

(ii) where one or both of $P^1$ represent $(C_{1-6}$-alkyl$)_3$Si, they may be removed by the use of, for example, a fluoride ion source, for example tetra-n-butylammonium fluoride or hydrogen fluoride;

(iii) where one or both of $P^1$ represent a $C_{1-6}$-alkyl group, where Y is $O-C_{1-6}$-alkyl and/or where Y is $NHR^7$ and $R^8$ is $C_{1-6}$-alkyl, $C_{1-6}$-alkyl groups may be removed by the use of, for example, boron tribromide;

(iv) where Y is O-benzyl, where one or both of $P^1$ represent a benzyl group and/or where Y is $NHR^7$ and $R^8$ is benzyl, benzyl groups may be removed by hydrogenolysis using a transition metal catalyst, for example palladium on charcoal, under an atmosphere of hydrogen, at a pressure of from 1 to 5 bar, in a solvent, such as acetic acid; and/or (v) where both $P^1$ together represent alkylidene or an alkoxy alkylidene, they may be removed by the use of, for example, a mineral or organic acid, preferably by using trifluoroacetic acid in dichloromethane or water at room temperature.

Deprotecting a compound of formula (II) as defined above but wherein Y is $NHR^7$ wherein $R^7$ is as defined above prepares a compound of formula (I) wherein X is $NHR^3$ wherein $R^3$ is a $C_{1-6}$-alkyl group substituted by a COOH group and optionally by one or more halogen atoms and/or $OR^4$, $C(NH)NR^4R^5$, $C(O)NR^4R^5$, phenyl and/or $C_{1-6}$-alkyl groups. Such deprotection is preferably carried out using a compound of formula (II) as defined above but wherein $R^8$ is t-butyl and both $P^1$ together represent isopropylidene with trifluoroacetic acid in dichloromethane at room temperature.

Salts of the compounds of formula (I) may be formed by reacting the free acid, or a salt thereof, or the free base, or a salt or a derivative thereof, with one or more equivalents of the appropriate base (for example ammonium hydroxide optionally substituted by $C_{1-6}$-alkyl or an alkali metal or alkaline earth metal hydroxide) or acid (for example ahydrohalic (especially HCl), sulphuric, oxalic or phosphoric acid). The reaction may be carried out in a solvent or medium in which the salt is insoluble or in a solvent in which the salt is soluble, e.g. water, ethanol, THF or diethyl ether, which may be removed in vacuo, or by freeze drying. The reaction may also be ametathetical process or it may be carried out on an ion exchange resin. The non-toxic physiologically acceptable salts are preferred, although other salts may be useful, e.g. in isolating or purifying the product.

To prepare a compound of formula (II) wherein Y is $NHR^3$ and $R^1$, $R^2$ and $P^1$ are as defined above, a compound of formula (II) wherein Y is OH and $R^1$, $R^2$ and $P^1$ are defined above is reacted with $R^3NH_2$ wherein $R^3$ is as defined above. The reaction is preferably carried out in the presence of a coupling agent using methods known from peptide synthesis (see M. Bodanszky and A. Bodanszky, The Practice of Peptide Synthesis, Springer-Verlag, 1984). Suitable coupling agents include 1,1'-carbonyldiimidazole and dicyclohexylcarbodiimide; the preferred coupling agent is bromo-tris-pyrrolidino-phosphonium hexafluorophosphate or benzotriazole-1-yl-oxy-tris-(dimethylamino) phosphoniumhexafluorophosphate, used in the presence of N,N-diethylisopropylamine. The reaction is preferably carried out in N,N-dimethylformamide (DMF) or tetrahydrofuran (THF) and preferably at a temperature of from $-15°$ to $120°$ C., more preferably at a temperature of from $0°$ C. to room temperature. This reaction may correspondingly be used to convert a compound of formula (I) wherein X is OH and $R^1$ and $R^3$ are as defined above to a compound of formula (I) wherein X is $NHR^3$ and $R^1$, $R^2$ and $R^3$ are as defined above.

To prepare a compound of formula (II) as defined above but where Y is $NHR^7$ wherein $R^7$ is as defined above, a compound of formula (II) wherein Y is OH is reacted with a compound of formula $R^7NH_2$ wherein $R^7$ is as defined above, using the coupling conditions described above.

A compound of formula (II) as defined above but wherein Y is $NHR^3$ wherein $R^3$ is a $C_{1-6}$-alkyl group substituted by a $C(O)NR^4R^5$ group and optionally by one or more halogen atoms and/or $OR^4$, $C(NH)NR^4R^5$, $C(O)NR^4R^5$, phenyl and/or $C_{1-6}$-alkyl groups, may be prepared by reacting a compound of formula (II) as defined above but wherein Y is $NHR^3$ wherein $R^3$ is a $C_{1-6}$-alkyl group substituted by a COOH group and optionally by one or more halogen atoms and/or $OR^4$, $C(NH)NR^4R^5$, $C(O)NR^4R^5$, phenyl and/or $C_{1-6}$-alkyl groups, with $HNR^4R^5$ wherein $R^4$ and $R^5$ are as defined above in the presence of a coupling agent as defined above. This reaction may also be used to convert a compound of formula (I) as defined above but wherein X is $NHR^3$ wherein $R^3$ is a $C_{1-6}$-alkyl group substituted by a COOH group and optionally by one or more halogen atoms and/or $OR^4$, $C(NH)NR^4R^5$, $C(O)NR^4R^5$, phenyl and/or $C_{1-6}$-alkyl groups to a compound of formula (I) as defined above but wherein X is $NHR^3$ wherein $R^3$ is a $C_{1-6}$-alkyl group substituted by a $C(O)NR^4R^5$ group and optionally by one or more halogen atoms and/or $OR^4$, $C(NH)NR^4R^5$, $C(O)NR^4R^5$, phenyl and/or $C_{1-6}$-alkyl groups.

A compound of formula (II) as defined above but wherein Y is $NHR^3$ wherein $R^3$ is a $C_{1-6}$-alkyl group substituted by a COOH group and optionally by one or more halogen atoms and/or $OR^4$, $C(NH)NR^4R^5$, $C(O)NR^4R^5$, phenyl and/or $C_{1-6}$-alkyl groups wherein $R^4$ and $R^5$ are as defined above, may be prepared by deprotecting a compound of formula (II) as defined above but wherein Y is $NHR^7$ using the deprotection procedures given in (i), (iii) or (iv) above.

A compound of formula (II) wherein Y is $NHR^3$ or $NHR^7$ can be prepared by first activating a compound of formula (II) wherein Y is OH and then treating it with $R^3NH_2$ or $R^7NH_2$ wherein $R^3$ and $R^7$ as defined above, or a salt thereof. The treatment is generally carried out in an inert solvent at a temperature of from $-20$ to $150°$ C.

Methods of activating a compound of formula (II) wherein Y is OH include formation of an acyl halide or an acetic anhydride. Acid anhydrides may be formed by treatment with an acyl halide, such as acetyl chloride in the presence of a base, such as pyridine or by treatment with a dehydrating agent such as acetic acid anhydride or phosphorus pentoxide in an inert solvent. Acyl halides may be formed by treatment of the acid with a halogenating agent, for example P(III), P(V) or S(IV) halides such as phosphorus trichloride. Acyl halides may also be prepared by an exchange reaction of the acid with an acyl halide such as oxalyl bromide. The reactions may be performed in the halogenating agent or acyl halide as solvent or in other inert solvents such as methylene chloride, at a temperature of from 0 to $150°$ C. Activation is preferably carried out by treatment with oxalyl chloride in dichloromethane at room temperature.

The substituent $R^1$ in the compound of formula (II) may optionally be replaced by first oxidising the compound of formula (II) to a compound of formula III:

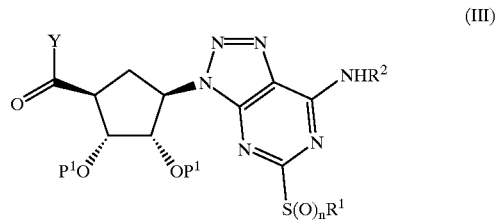

(III)

wherein $R^1$, $P^1$, Y and $R^2$ are as defined above and n is 1 or 2, using an organic oxidant such as dimethyldioxirane or an inorganic oxidant such as sodium hypochlorite in an inert solvent, such as dichloromethane or a mixture of methanol and water, at a temperature of from $-20$ to $40°$ C., preferably the oxidant is either Oxone (registered trademark) and the reaction is carried out in acetonitrile/water at room temperature or the oxidant is 3-chloroperoxybenzoic acid and the reaction is carried out in dichloromethane. This reaction may correspondingly be used to change the substituent $R^1$ in a compound of formula (I).

The compound of formula (III) is then treated with a compound of formula $R^1SM$ wherein $R^1$ is as defined above and M is an alkali metal, for example lithium or potassium, to give a compound of formula (II) with a different substituent $R^1$. The reaction is generally carried out in an inert solvent at a temperature of from $-20$ to $40°$ C. M is preferably sodium and the reaction is preferably carried out in tetrahydrofuran at room temperature.

A compound of formula $R^1SM$ may be prepared by reacting $R^1SH$ with a base such as $C_{1-6}$-alkyl-M or MH, wherein M is as defined above, in an inert solvent at a temperature of from $-20$ to $40°$ C.

A compound of formula (II) wherein Y is OH, $O-C_{1-6}$-alkyl or O-benzyl can be prepared by reacting a compound of formula IV:

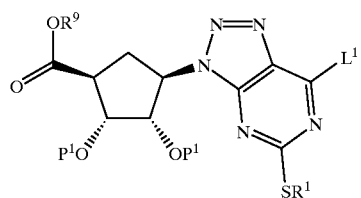

(IV)

wherein $R^1$ and $P^1$ are as defined above, $L^1$ is a leaving group, for example a halogen atom and $R^9$ is a H atom or a $C_{1-6}$-alkyl or benzyl group, with $NH_2R_2$ or a salt of $NH_2R^2$ wherein $R^2$ is as defined above, in the presence of a base. Suitable salts of $NH_2R^2$ include hydrochlorides. Suitable bases include an organic base such as triethylamine or an inorganic base such as potassium carbonate.

A compound of formula (IV) can be prepared by diazotising a compound of formula V:

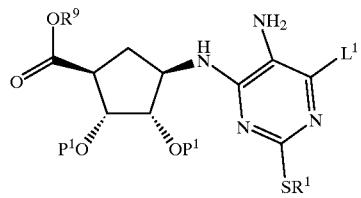

(V)

wherein $R^1$, $R^9$, $L^1$ and $P^1$ are as defined above, with a metal nitrite, for example an alkali metal nitrite, especially sodium nitrite in dilute aqueous acid, for example 2M HCl, or with a $C_{1-6}$-alkyl nitrite in an inert solvent, at a temperature of from −20 to 100° C.; preferred conditions are isoamyl nitrite in acetonitrile at 80° C.

A compound of formula (V) wherein $R^9$ is H can be prepared by reducing and hydrolysing a compound of formula VI:

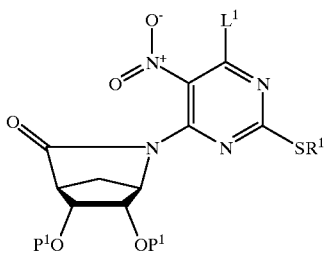

(VI)

wherein $R^1$, $L^1$ and $P^1$ are as defined above. The reduction may be carried for example by using hydrogenation with a transition metal catalyst at a temperature around room temperature, for example palladium on charcoal under an atmosphere of hydrogen, preferably at a pressure from 1 to 5 atmospheres, in a solvent, for example ethanol, or by using iron in an acidic solvent such as acetic acid at a temperature of about 100° C.

To prepare a compound of formula (V) wherein $R^9$ is H, hydrolysis of the compound of formula (VI) may be performed by using a mineral acid such as HCl or a strong organic acid such as trifluoroacetic acid in a solvent such as aqueous 1,4-dioxane, at a temperature of from 20 to 150° C. Preferably the reduction and hydrolysis are carried out simultaneously using iron in an acidic solvent, for example acetic acid, containing an alkaline earth metal halide, for example calcium chloride, at a temperature of about 80° C.

To prepare a compound of formula (V) wherein $R^9$ is $C_{1-6}$-alkyl or benzyl, the compound of formula (VI) is treated with iron in acetic acid at a temperature of from 50 to 80° C. so that the nitro group is reduced. The resulting intermediate is then treated with sodium borohydride in a mixture of water and $C_{1-6}$-alkyl alcohol or benzyl alcohol at around room termperature.

A compound of formula (VI) can be prepared by reacting a compound of formula VII:

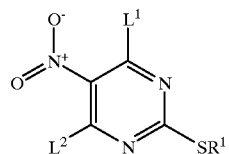

(VII)

wherein $L^1$ and $R^1$ are as defined above and $L^2$ is a leaving group, for example a halogen atom, wherein $L^1$ and $L^2$ are preferably the same, with a compound of formula VIII:

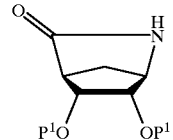

(VIII)

wherein $P^1$ is as defined above, in the presence of a base such as $C_{1-6}$-alkyl-M or MH wherein M is as defined above, for example butyl lithium, in an inert solvent, such as tetrahydrofuran (THF), at a temperature of from −10 to 100° C. Preferably sodium hydride is used in THF at room temperature.

A compound of formula (VII) may be prepared from 4,6-dihydroxy-2-mercaptopyrimidine by alkylation with $R^1L^3$ wherein $R^1$ is as defined above and $L^3$ is a suitable leaving group, for example a halogen atom, followed by nitration, whereafter the two alcohols are converted to leaving groups $L^1$ and $L^2$.

All novel intermediates form an aspect of the invention. In particular the invention further provides an intermediate of formula (III) wherein $R^1$, $R^2$, $P^1$, n and Y are as defined above.

The compounds of the invention act as $P_{2T}$-receptor antagonists. Accordingly, the compounds are useful in therapy, especially adjunctive therapy, particularly they are indicated for use as: inhibitors of platelet activation, aggregation and degranulation, anti-thrombotic agents or in the treatment or prophylaxis of unstable angina, coronary angioplasty (PTCA), myocardial infarction, perithrombolysis, primary arterial thrombotic complications of atherosclerosis such as thrombotic or embolic stroke, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, antiphospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia; or in the prevention of mechanically-induced platelet activation in vivo, such as cardiopulmonary bypass (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, atheromatous plaque formation/progression, vascular stenosis/restenosis and asthma, in which platelet-derived factors are implicated in the disease process.

According to the invention there is further provided the use of a compound according to the invention in the manufacture of a medicament for the treatment of the above disorders, in particular a platelet aggregation disorder. The invention also provides a method for the treatment of the above disorders, in particular a platelet aggregation disorder which comprises administering to a patient suffering from such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, or by rectal administration in the form of suppositories or transdermally.

The compounds of the invention may be administered on their own or as a pharmaceutical composition comprising the compound of the invention in combination with a pharmaceutically acceptable diluent, adjuvant or carrier.

Dry powder formulations and pressurized HFA aerosols of the compounds of the invention may be administered by oral or nasal inhalation. For inhalation the compound is desireably finely divided. The finely divided compound preferably has a mass median diameter of less than 10 μm, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure.

This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral solutions or suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

The invention is illustrated by the following examples which should not be interpreted as limiting the invention. In the examples the NMR spectra were measured on a Varian Unity Inova 300 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as ($SiO_2$)) was carried out using Fisher Matrix silica, 35–70 μm.

EXAMPLE 1

[1S-(1α,2β,3β,4α)]-4-[7-(butylamino)-5-(propylthio)-3H-1,2,3-triazolo[4,5-d]pyrimidin-3-yl]-2,3-dihydroxy-cyclopentanecarboxamide (a) 4,6-Dihydroxy-2-(propylthio)pyrimidine Propyl iodide (136 ml) was added to a suspension of 4,6-dihydroxy-2-mercaptopyrimidine (200 g) in water (800 ml), containing sodium hydroxide (55.6 g). The reaction mixture was stirred for 2 weeks then concentrated to half volume, 2N hydrochloric acid was added and the subtitle compound was isolated by filtration (167 g).

MS (EI) 186 (M⁺, 100%).

(b) 4,6-Dihydroxy-5-nitro-2-(propylthio)pyrimidine

The product of step (a) (70 g) was added slowly to ice-cooled fuming nitric acid (323 ml). The reaction mixture was stirred for 1 hour then poured onto ice and the subtitle compound was isolated by filtration (65 g).

MS (EI) 231 (M⁺), 41 (100%).

(c) 4,6-Dichloro-5-nitro-2-(propylthio)pyrimidine

N,N-Diethylaniline (150 ml) was added dropwise to a stirred suspension of the product of step (b) (134 g) in phosphoryl chloride (500 ml) then the resulting solution heated at reflux for 1 hour. The cooled reaction mixture was poured onto ice then extracted with diethyl ether (3×500 ml). The combined extracts were dried and concentrated. Chromatography ($SiO_2$, isohexane: diethyl ether, 19:1 as eluant) gave the subtitle compound (128 g).

MS (EI) 271, 269, 267 (M⁺), 41 (100%).

(d) [3aS-(3aα,4β,7β,7aα)]5-[6-Chloro-5-nitro-2-(propylthio)pyrimidin-4-yl]-tetrahydro-2,2-dimethyl-4,7-methano-1,3-dioxolo[4,5-c]pyridin-6(3aH)-one Sodium hydride (60%, 4.00 g) was added portionwise to [3aS-(3aα,4β,7β,7aα] tetrahydro-2,2-dimethyl-4,7-methano-1,3-dioxolo[4,5-c]pyridin-6(3aH)-one (18.3 g) in THF (500 ml). On stirring for 1 hour the solution was added dropwise to the product of step (c) (54.0 g) in THF (500 ml). The reaction mixture was stirred at room temperature for 45 minutes then concentrated and purified by chromatography ($SiO_2$, dichloromethane: isohexane, 3:2 as eluant) to afford the subtitle compound (79.2 g).

MS (APCI) 417, 415 (M+H⁺), 415 (100%).

(e) [3aR-(3aα,4α,6α,6aα)]-6-[[5-Amino-6-chloro-2-(propylthio)-4-pyrimidinyl]amino]-tetrahydro-2,2-dimethyl-4H-cyclopenta-1,3-dioxole-4-carboxylic acid Iron powder (10.0 g) was added to a stirred solution of the product of step (d) (100 g), and calcium chloride (1.49 g) in ethanol (140 ml). The reaction mixture was heated at reflux for 10 minutes then filtered through celite, washing several times with hot ethanol. The filtrate was concentrated to afford the subtitle compound (9.3 g).

MS (FAB) 405, 403 (M+H⁺), 405 (100%).

(f) [3aR-(3aα,4α,6α,6aα)]-6-[7-Chloro-5-(propylthio)-3H-1,2,3-triazolo[4,5-d]pyrimidin-3-yl]-tetrahydro-2,2-dimethyl-4H-cyclopenta-1,3-dioxole-4-carboxylic acid Isoamyl nitrite (6.02 ml) was added to a solution of the product of step (e) (9.28 g) in acetonitrile (80 ml) and the solution heated at 70° C. for 1 hour. The cooled reaction mixture was concentrated and purified ($SiO_2$, ethyl acetate:isohexane 2:1 as eluant) to afford the subtitle compound (7.9 g).

MS (FAB) 416, 414 (M+H⁺), 414 (100%).

(g) [3aR-(3aα,4α,6α,6aα)]-6-[7-(butylamino)-5-(propylthio)-3H-1,2,3-triazolo[4,5-d]pyrimidin-3-yl]-tetrahydro-2,2-dimethyl-4H-cyclopenta-1,3dioxole-4-carboxylc acid The product from step (f) (5.52 g) and butylamine (5 ml) in 1,4-dioxane (25 ml) were stirred at room temperature for 1 hour. The reaction mixture was concentrated and the residue purified ($SiO_2$, dichloromethane:ethyl acetate 2:1 as eluant) to afford the subtitle compound (2.2 g).

MS (FAB) 451 (M+H⁺, 100%).

(h) [3aR-(3aα,4α,6α,6aα)]-6-[7-(Butylamino)-5-(propylthio)-3H-1,2,3-triazolo[4,5-d]pyrimidin-3-yl]-tetrahydro-2,2-dimethyl-4H-cyclopenta-1,3-dioxole-4-carboxamide Oxalyl chloride (0.24 ml) was added dropwise to a solution of the product of step (g) (0.60 g) in dichloromethane (15 ml) and the solution stirred at room temperature for 2 hours then concentrated. The residue was taken into dichloromethane (10 ml) cooled to 0° C. and 880 ammonia (10 ml) added, then the solution stirred at room temperature for 18 hours. The resulting solid was collected by filtration and dried under vacuum to afford the subtitle compound (0.48 g).

MS (FAB) 438 (M+H⁺, 100%).

(i) [1S-(1α,2β,3β,4α)]-4-[7-(Butylamino)-5-(propylthio)-3H-1,2,3-triazolo[4,5-d]pyrimidin-3-yl]-2,3-dihydroxycyclopentanecarboxamide A solution of the product from step (h) (0.48 g) in trifluoroacetic acid (9 ml)/water (1 ml) was stirred at room temperature for 5 hours. The reaction mixture was concentrated and the residue purified by chromatography ($SiO_2$, dichloromethane:methanol, 15:1 as eluant) to afford the title compound (0.17 g).

Melting point: 209–211° C. (EtOAc);

NMR δH ($d_6$-DMSO) 8.96 (1H, t), 7.40–6.90 (2H, m), 5.03–4.96 (2H, m), 4.22 (1H, m), 3.89 (1H, m), 3.40 (2H, m), 2.80 (2H, m), 2.43–2.31 (2H, m), 1.73–1.51 (4H, m), 1.37–1.31 (2H, m), 0.98 (3H, t), 0.90 (3H, t).

EXAMPLE 2

[1S-(1α,2β,3β,4α)]-4-[7-(butylamino)-5-(propylthio)-3H-1,2,3-triazolo[4,5-d]pyrimidin-3-yl]-2,3-dihydroxy-cyclopentanecarboxylic acid Prepared according to the method of Example 1 step (i) using the product of Example 1 step (g).

NMR δH ($d_6$-DMSO) 9.01–8.98 (1H, t), 5.03–4.96 (1H, m), 4.42–4.39 (1H, m), 4.21 (1H, m), 3.89 (1H, m), 3.52–3.46 (2H, m), 3.15–3.03 (2H, m), 1.73–1.55 (4H, m), 1.37–1.31 (2H, m), 0.98 (3H, t), 0.91 (3H, t);

MS (FAB) 411 (M+H⁺, 100%).

EXAMPLE 3

[1S-(1α,2β,3β,4α)]-4-[7-(cyclopropylamino)-5-(propylthio)-3H-1,2,3-triazolo[4,5-d]pyrimidin-3-yl]-2,3-dihydroxy-cyclopentanecarboxamide (a) [3aR-(3aα,4α,6α,6aα)]-6-[7-(Cyclopropylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of Example 1 step (g) using the product of Example 1 step (f) and cyclopropylamine.

NMR δH ($d_6$-DMSO) 7.95 (1H, d), 5.72 (1H, m), 5.58 (1H, m), 5.12 (1H, d), 3.36–3.01 (2H, m), 3.02–2.88 (2H, m), 2.60–2.46 (1H, m), 1.88–1.78 (2H, m), 1.56 (3H, s), 1.45 (3H, s), 1.10 (3H, t), 0.75 (2H, t), 0.38 (2H, br s).

(b) [3aR-(3aα,4α,6α,6aα)]-6-[7-(Cyclopropylamino)-5-(propylthio)-3H-1,2,3-triazol[4,5-d]pyrimidin-3-yl]-tetrahydro-2,2-dimethyl-4H-cyclopenta-1,3-dioxole-4-carboxamide Prepared according to the method of Example 1 step (h) using the product of step (a).

MS (FAB) 434 (M+H⁺, 100%).

(c) [1S-(1α,2β,3β,4α)]-4-[7-(Cyclopropylamino)-5-(propylthio)-3H-1,2,3-triazolo[4,5-d]pyrimidin-3-yl]-2,3-dihydroxy-cyclopentanecarboxamide Prepared according to the method of Example 1 step (i) using the product of step (b).

MS (FAB) 394 (M+H⁺, 100%).

EXAMPLE 4

[1S-(1α,2β,3β,4α)]-4-[7-(cyclopropylamino)-5-(propylthio)-3H-1,2,3-triazolo[4,5-dlpyrimidin-3-yl]-2,3-dihydroxy-cyclopentanecarboxylic acid Prepared according to the method of Example 1 step (i) using the product of Example 3 step (a).

MS (APCI) 395 (M+H⁺, 100%);

NMR δH (d₆-DMSO) 9.10 (1H, d), 5.07 (1H, m), 4.45 (1H, m), 4.42 (1H, m), 3.26–3.00 (3H, m), 2.80 (1H, t), 2.57–2.43 (2H, m), 1.74 (2H, m), 1.01 (3H, t), 0.94–0.72 (4H, m).

EXAMPLE 5

[1S-[1α,2β,3β,4α(trans)]]-2,3-dihydroxy-4-[7-[(2-phenylcyclopropyl)amino]-5-(propylthio)-3H-1,2,3-triazolo[4,5-d]pyrimidin-3-yl]-cyclopentanecarboxylic acid (a) [3aR-[3aα,4α,6α(trans),6aα]]-6-[7-[2-Phenylcyclopropyl)amino]-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of Example 1 step (g) using the product of Example 1 step (f), (trans) 2-phenylcyclopropylamine hydrochloride and triethylamine.

MS (APCI) 511 (M+H⁺, 100%).

(b) [1S-(1α,2β,3β,4α)]-4-[(2-Phenylcyclopropyl)amino]-5-(propylthio)-3H-1,2,3-triazolo[4,5-d]pyrimidin-3-yl]-2,3-dihydroxy-cyclopentanecarboxylic acid Prepared according to the method of Example 1 step (i) using the product of step (a).

MS (APCI) 471 (M+H⁺, 100%); NMR δH (d₆-DMSO) 9.36 (1H, d), 7.31–7.15 (5H, m), 5.01 (1H, q), 4.40 (1H, m), 4.21 (1H, m), 3.19 (1H, m), 2.91–2.82 (3H, m), 2.51–2.13 (4H, m), 1.53–1.48 (2H, m), 1.34 (1H, m), 0.81 (2H, m).

EXAMPLE 6

[1S-[1α,2β,3β,4α(trans)]]-2,3-dihydroxy-4-[7-[(2-phenylcyclopropyl)-amino]-5-(propylthio)-3H-1,2,3-triazolo[4,5-d]pyrimidin-3-yl]-cyclopentanecarboxamide Prepared according to the method of Example 1 step (h) using the product of Example 5 and purified by flash chromatography (SiO₂, chloroform:methanol 93:7 as eluant).

MS (APCI) 470 (M+H⁺, 100%); NMR δH (d₆-DMSO) 9.36 (1H, d), 7.39 (1H, s), 7.29 (2H, m), 7.18 (3H, m), 6.93 (1H, s), 5.12 (1H, d), 4.99 (1H, d), 4.96 (1H, m), 4.39 (1H, m), 4.11 (1H, q), 3.20 (1H, m), 2.89 (2H, m), 2.74 (1H, m), 2.28 (2H, m), 2.13 (1H, m), 1.47 (3H, m), 1.34 (1H, m), 0.81 (3H, t).

EXAMPLE 7

[1S-[1α,2β,3β,4α)]]-2,3-dihydroxy-4-[7-(2-phenylethylamino)-5-(propylthio)-3H-1,2,3-triazolo[4,5-d]pyrimidin-3-yl]-cyclopentanecarboxylic acid (a) [3aS-(3aα,4β,7β,7aα)]5-[5-amino-6-chloro-2-(propylthio)-pyrimidin-4-yl]-tetrahydro-2,2-dimethyl-4,7-methano-1,3-dioxolo[4,5-c]pyridin-6(3aH)-one Reduced iron powder (50 g) was added to a solution of the product of Example 1 step (d) (50.0 g) in glacial acetic acid (1800 ml) and the reaction mixture heated at reflux for 15 minutes. The cooled reaction mixture was concentrated and the residue taken into ether (300 ml) then washed with sodium bicarbonate solution (2×200 ml). The organic phase was dried and concentrated and the residue purified (SiO₂, dichloromethane:diethyl ether 9:1 as eluant) to afford the subtitle compound (42.6 g).

(b) [3aR-(3aα,4α,6α,6aα)]-6-[[5-Amino-6-chloro-2-(propylthio)-4-pyrimidinyl]amino]-tetrahydro-2,2-dimethyl-4H-cyclopenta-1,3-dioxole-4-carboxylic acid, methyl ester Sodium borohydride (0.60 g) was added, over 30 minutes to an ice-cooled solution of the product of step (a) (4.50 g) in methanol (100 ml). The solution was concentrated and purified by chromatography (SiO₂, dichloromethane: ethyl acetate, 95:5 as eluant) to give the subtitle compound (2.1 g).

MS (APCI) 419, 417 (M+H⁺), 417 (100%).

Further elution gave [3aR-(3aα,4α,6α,6aα)]-6-[[5-amino-6-chloro-2-(propylthio)-4-pyrimidinyl]amino]-tetrahydro-2,2-dimethyl-4H-cyclopenta-1,3-dioxole-4-methanol (2.4 g).

MS (APCI) 419, 417 (M+H⁺), 417 (100%).

(c) [3aR-(3aα,4α,6α,6aα)]-6-[7-Chloro-5-(propylthio)-3H-1,2,3-triazolo[4,5-d]pyrimidin-3-yl]-tetrahydro-2,2-dimethyl-4H-cyclopenta-1,3-dioxole-4-carboxylic acid, methyl ester Prepared according to the method of Example 1 step (f) using the product of step (b).

MS (FAB) 430, 428 (M+H⁺), 417 (100%).

(d) [3aR-(3aα,4α,6α,6aα)]-6-[7-(2-Phenylethylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid, methyl ester Prepared according to the method of Example 1 step (g) using the product of step (c), phenylethylamine hydrochloride and potassium carbonate.

MS (APCI) 513 (M+H⁺, 100%).

(e) [1S-(1α,2β,3β,4α)]-4-[7-(2-Phenylethylamino)-5-(propylthio)-3H-1,2,3-triazolo[4,5-d]pyrimidin-3-yl]-2,3-dihydroxy-cyclopentanecarboxylic acid, methyl ester Prepared according to the method of Example 1 step (i) using the product of step (d).

MS (APCI) 473 (M+H⁺, 100%).

(f) [1S-(1α,2β,3β,4α)]-4-[7-(2-Phenylethylamino)-5-(propylthio)-3H-1,2,3-triazolo[4,5-d]pyrimidin-3-yl]-2,3-dihydroxycyclopentanecarboxylic acid Lithium hydroxide monohydrate (56 mg) was added to a solution of the product of step (e) (0.25 g) in THF (30 ml)/water (30 ml). The solution was stirred at room temperature for 18 hours then 2M HCl (aq) added until the pH was 7 before extracting with ethyl acetate (3×40 ml). The combined organics were dried and concentrated to afford the title compound.

MS (APCI) 459 (M+H⁺, 100%); Elemental analysis Found C: 54.77; H: 5.72; N: 18.00; S: 7.34% Required C: 55.00; H: 5.72; N: 18.30; S: 7.00%

EXAMPLE 8

[1S-(1α,2β,3β,4α)]-2,3-dihydroxy-4-[7-(2-phenylethylamino)-5-(propylthio)-3H-1,2,3-triazolo[4,5-d]pyrimidin-3-yl]-cyclopentanecarboxamide Prepared according to the method of Example 1 step (h) using the product of Example 7.

NMR δH (d₆-DMSO) 9.10 (1H, d), 7.31 (1H, s), 7.30–7.15 (4H, m), 6.94 (1H, s), 5.14 (1H, d), 5.00 (1H, d), 5.004.90 (1H, m), 4.45–4.30 (lH, m), 4.20–4.00 (1H, m), 3.80–3.60 (2H, m), 3.20–3.00 (2H, m), 3.00–2.90 (2H, m), 2.80–2.70 (1H, m), 2.40–2.10 (2H, m), 1.75–1.60 (2H, m), 0.97 (3H, t).

EXAMPLE 9

[1S-(1α,2β,3β,4α)]-2,3-dihydroxy-4-[7-[2-(methylthio)ethylaminol-5-(propylthio)-3H-1,2,3-triazolo[4,5-d]pyrimidin-3-yl]-cyclopentanecarboxylic acid The product of Example 1 step (f) (2.0 g) and 2-(methylthio)ethylamine (0.91 g) in 1,4-dioxane (25 ml)

were stirred at room temperature for 1 hour. The reaction mixture was concentrated and the residue taken into trifluoroacetic acid (20 ml)/water (10 ml) then stirred at room temperature for 1 hour. The reaction mixture was concentrated and the residue purified by chromatography (HPLC, Nova-pak® C18 column, 0.1% ammonium acetate:methanol, 60:40 as eluant) to afford the product (0.17 g).

MS (APCI) 429 (M+H$^+$, 100%); NMR δH (d$_6$-DMSO) 5.00 (1H, m), 4.44 (1H, m), 4.19 (1H, m), 3.71 (2H, m), 3.01 (2H, m), 2.78–2.65 (3H, m), 2.35 (2H, t), 2.12 (3H, s), 1.74 (2H, m), 0.98 (3H, m).

EXAMPLE 10

[1S-(1α,2β,3β,4α)]-2,3-dihydroxy-4-[7-[2-(methylthio)ethylamino]-5-(propylthio)-3H-1,2,3-triazolo[4,5-d]pyrimidin-3-yl]-cyclopentanecarboxamide Prepared according to the method of Example 1 step (h) using the product of Example 9.

MS (APCI) 428 (M+H$^+$, 100%);

NMR δH (d$_6$-DMSO) 9.07 (1H, t), 8.66 (1H, t), 7.38 (IH, s), 6.93 (1H, s), 5.15 (2H, br s), 4.97 (1H, m), 4.46 (1H, m), 4.12 (1H, m), 3.70 (2H, m), 3.10 (2H, m), 2.75 (3H, m), 2.39–2.18 (2H, m), 1.70 (2H, m), 1.00 (3H, t).

EXAMPLE 11

[1S-[1α,2β,3β,4α(trans)]]-4-[5-(Cyclohexylthio)-7-[2-(phenylcyclopropyl)amino]-3H-1,2,3-triazolo[4,5-d]pyrimidin-3-yl]-2,3-dihydroxy-cyclopentanecarboxylic acid (a) [3aR-[3aα,4α,6α,6aα(trans)]]-Tetrahydro-2,2-dimethyl-6-[7-(2-phenylcyclopropylamino)-5-(propylsulfonyl)-3H-1,2,3-triazolo[4,5-d]pyrimidin-3-yl]-4H-cyclopenta-1,3-dioxole-4-carboxylic acid 3-Chloroperoxybenzoic acid (0.14 g) was added to a solution of the product of Example 5 step (a) (0.11 g) in dichloromethane (8 ml) and the resulting solution stirred at room temperature for 18 hours. The solution was washed with aqueous sodium metabisulfite solution (3×10 ml) then dried and concentrated. Purification by chromatography (SiO$_2$, ethyl acetate: isohexane, 1:1 as eluant) gave the subtitle compound (0.12 g).

MS (APCI) 543 (M+H$^+$, 100%).

(b) [3aR-[3aα,4α,6α,6aα(trans)]]-6-[5-(cyclohexylthio)-7-[2-phenylcyclopropyl)amino]-3H-1,2,3-triazolo[4,5-d]pyrimidin-3-yl]-tetrahydro-2,2-dimethyl-4H-cyclopenta-1,3-dioxole-4-carboxylic acid Cyclohexanethiol (0.16 g) was added dropwise to a suspension of sodium hydride (60%, 55 mg) in N,N-dimethylformamide (DMF) (10 ml). After 30 minutes, a solution of the product of step (a) (0.30 g) in DMF (10 ml) was added dropwise over 45 minutes then the reaction was stirred for 45 minutes. The reaction mixture was added slowly to a solution of sodium chloride (10 ml), containing acetic acid (1 ml) then the solution extracted with ethyl acetate (50 ml). The organic phase was dried and concentrated and the residue purified by chromatography (SiO$_2$, ethyl acetate: isohexane, 2:1 as eluant) to give the subtitle compound (0.26 g).

MS (APCI) 551 (M+H$^+$, 100%).

(c) [1S-[1α,2β,3β,4α(trans)]]-4-[5-(Cyclohexylthio)-7-[2-(phenylcyclopropyl)amino]-3H-1,2,3-triazolo[4,5-d]pyrimidin-3-yl]-2,3-dihydroxy-cyclopentanecarboxylic acid Prepared according to the method of Example 1 step (i) using the product of step (b).

MS (APCI) 511 (M+H$^+$, 100%); NMR δH (d$_6$-DMSO) 12.42 (1H, s), 7.29 (2H, m), 7.18 (3H, m), 5.16 (2H, m), 5.00 (1H, q), 4.42 (1H, m), 4.22 (1H, q), 3.58 (1H, m), 3.20 (1H, m), 2.82 (1H, m), 2.40 (2H, m), 2.15 (IH, m), 1.94 (1H, m), 1.79 (1H, m), 1.57–1.18 (10H, m).

EXAMPLE 12

[1S-[1α,2β,3β,4α(trans)]]-2,3-Dihydroxy-4-[7-[(2-phenylcyclopropyl)amino]-5-(cyclohexylthio)-3H-1,2,3-triazolo[4,5-d]pyrimidin-3-yl]-cyclopentanecarboxamide Prepared according to the method of Example 1 step (h) using the product of Example 11.

MS (APCI) 510 (M+H$^+$, 100%); NMR δH (d$_6$-DMSO) 9.32 (1H, d), 7.37 (1H, s), 7.29 (2H, m), 7.18 (3H, m), 6.92 (1H, s), 5.11 (1H, d), 4.93 (2H, m), 4.40 (1H, q), 4.12 (1H, m), 3.60 (1H, m), 3.20 (1H, m), 2.75 (1H, m), 2.28 (2H, m), 2.14 (1H, m), 1.92 (1H, m), 1.77 (1H, m), 1.57–1.18 (10H, m).

EXAMPLE 13

[1S-(1α,2β,3β,4α)]-4-[7-(Butylamino)-5-(3,4-dichlorophenylthio)-3H-1,2,3-triazolo[4,5-d]pyrimidin-3-yl]-2,3-dihydroxy-cyclopentanecarboxylic acid (a) [3aR-(3aα,4α,6α,6aα)]-6-[7-(Butylamino)-5-(propylsulfonyl)-3H-1,2,3-triazolo[4,5-d]pyrimidin-3-yl]-tetrahydro-2,2-dimethyl-4H-cyclopenta-1,3-dioxole-4-carboxylic acid Prepared according to the method of Example 11 step (a) using the product of Example 1 step (g).

MS (APCI) 483 (M+H$^+$), 349 (100%).

(b) [1S-(1α,2β,3β,4α)]-4-[7-(Butylamino)-5-(propylsulfonyl)-3H-1,2,3-triazolo[4,5-d]pyrimidin-3-yl]-2,3-dihydroxy-cyclopentanecarboxylic acid Prepared according to the method of Example 1 step (i) using the product of step (a).

MS (APCI) 443 (M+H$^+$, 100%).

(c) [1S-(1α,2β,3β,4α)]-4-[7-(Butylamino)-5-(3,4-dichlorophenylthio)-3H-1,2,3-triazolo[4,5-d]pyrimidin-3-yl]-2,3-dihydroxy-cyclopentanecarboxylic acid Prepared according to the method of Example 11 step (b) using the product of step (b) and 3,4-dichlorothiophenol.

MS (APCI) 517, 515, 513 (M+H$^+$), 513 (100%); NMR δH (d$_6$-DMSO) 12.40 (1H, br s), 9.15 (1H, t), 7.94 (1H, s), 7.72 (1H, d), 7.61 (1H, d), 4.97–4.94 (1H, m), 4.36–4.33 (1H, m), 4.19–4.16 (1H, m), 3.21–3.14 (2H, m), 2.82–2.78 (1H, m), 2.51–2.44 (1H, m), 2.26–2.21 (1H, m), 1.33 (2H, q), 1.13 (2H, q), 0.79 (3H, t).

EXAMPLE 14

[1S-(1α,2β,3β,4α)]-4-[7-(Butylamino)-5-(3,4-dichlorophenylthio)-3H-1,2,3-triazolo[4,5-d]pyrimidin-3-yl]-2,3-dihydroxy-cyclopentanecarboxamide Prepared according to the method of Example 1 step (h) using the product of Example 13.

MS (APCI) 516, 514, 512 (M+H$^+$), 512 (100%); NMR δH (d$_6$-DMSO) 9.16 (1H, t), 7.95–7.60 (3H, m), 7.40 (1H, s), 6.92 (1H, s), 5.14 (1H, d), 4.99 (1H, d), 4.92–4.89 (1H, m), 4.36–4.34 (1H, m), 4.08–4.05 (1H, m), 3.20–3.14 (2H, m), 2.76–2.72 (1H, m), 2.49–2.18 (2H, m), 1.35–1.30 (2H, m), 1.16–1.09 (2H, m), 0.79 (3H, t).

EXAMPLE 15

[1S-(1α,2β,3β,4α)]4-[7-(Butylamino)-5-[4-(trifluoromethyl)phenylthio]-3H-1,2,3-triazolo[4,5-d]pyrimidin-3-yl]-2,3-dihydroxy-cyclopentanecarboxylic acid Prepared according to the method of Example 11 step (b) using the product of Example 13 step (b) and 4-(trifluoromethyl)thiophenol.

MS (APCI) 513 (M+H$^+$, 100%); NMR δH (d$_6$-DMSO) 9.14 (1H, t), 7.88 (2H, d), 7.81 (2H, d), 5.00–4.91 (1H, m), 4.35–4.33 (1H, m), 4.16–4.10 (1H, m), 3.16–3.14 (2H, m), 2.78–2.75 (1H, m), 2.41–2.21 (2H, m), 1.36–1.27 (2H, q), 1.15–1.03 (2H, q), 0.77 (3H, t).

EXAMPLE 16

[1S-(1α,2β,3β,4α)]-4-[7-(Butylamino)-5-[4-(trifluoromethyl)phenylthio]-3H-1,2,3-triazolo[4,5-d]pyrimidin-3-yl]-2,3-dihydroxy-cyclopentanecarboxamide Prepared according to the method, of Example 1 step (h) using the product of Example 15.

MS (APCI) 512 (M+H$^+$, 100%); NMR δH (d$_6$-DMSO) 9.14 (1H, t), 7.90–7.79 (4H, m), 7.39 (1H, br s), 6.95 (1H, br s), 5.14 (1H, d), 4.99 (1H, d), 4.93 (1H, m), 4.36–4.34 (1H, m), 4.06 (1H, m), 3.15 (2H, q), 2.76–2.72 (1H, m), 2.49–2.19 (2H, m), 1.33–1.29 (2H, m), 1.12–1.05 (2H, m), 0.76 (3H, t).

EXAMPLE 17

[1S-(1α,2β,3β,4α)]-4-[7-(Butylamino)-5-(phenylthio)-3H-1,2,3-triazolo[4,5-d]pyrimidin-3-yl]-2,3-dihydroxy-cyclopentanecarboxylic acid Prepared according to the method of Example 11 step (b) using the product of Example 13 step (b) and thiophenol.

MS (APCI) 445 (M+H$^+$, 100%); NMR δH (d$_6$-DMSO) 9.01 (1H, t), 7.62 (2H, m), 7.46–7.43 (3H, m), 4.95–4.86 (1H, q), 4.36–4.31 (1H, m), 4.16–4.09 (1H, m), 3.20–3.14 (2H, m), 2.72–2.68 (1H, m), 2.50–2.17 (2H, m), 1.39–1.29 (2H, m), 1.19–1.07 (2H, m), 0.79 (3H, t).

EXAMPLE 18

[1S-(1α,2β,3β,4α)]-4-[7-(Butylamino)-5-(phenylthio)-3H-1,2,3-triazolo[4,5-d]pyrimidin-3-yl]-2,3-dihydroxy-cyclopentanecarboxamide Prepared according to the method of Example 1 step (h) using the product of Example 17.

MS (APCI) 444 (M+H$^+$, 100%); NMR δH (d$_6$-DMSO) 9.03 (1H, t), 7.64–7.44 (5H, m), 7.39 (1H, s), 6.95 (1H, m) 5.12 (1H, m), 4.99 (1H, m), 4.89 (1H, m), 4.35–4.31 (1H, m), 4.07 (1H, m), 3.17–3.15 (2H, m), 2.75–2.72 (1H, m), 2.49–2.16 (2H, m), 1.35–1.34 (2H, m), 1.12 (2H, m), 0.79 (3H, t).

EXAMPLE 19

[1S-(1α,2β,3β,4α)]-4-[7-(Cyclopropylamino)-5-(3,4-dichlorophenylthio)-3H-1,2,3-triazolo[4,5-d]pyrimidin-3-yl]-2,3-dihydroxy-cyclopentanecarboxamide (a) [1S-(1α,2β,3β,4α)]-4-[7-(Cyclopropylamino)-5-(propylsulfonyl)-3H-1,2,3-triazolo[4,5-d]pyrimidin-3-yl]-2,3-dihydroxy-cyclopentanecarboxalide Prepared according to the method of Example 11 step (a) using the product of Example 3.

MS (APCI) 426 (M+H$^+$, 100%).

(b) [1S-(1α,2β,3β,4α)]-4-[7-(Cyclopropylamino)-5-(3,4-dichlorophenylthio)-3H-1,2,3-triazolo[4,5-d]pyrimidin-3-yl]-2,3-dihydroxy-cyclopentanecarboxamide Prepared according to the method of Example 11 step (b) using the product of step (a) and 3,4-dichloro-thiophenol.

MS (APCI) 498, 496 (M+H$^+$), 496 (100%); NMR δH (d$_6$-DMSO) 9.28 (1H, d), 8.01 (1H, d), 7.81–7.60 (2H, m), 7.40 (1H, s), 6.95 (1H, s), 5.11 (1H, d), 4.98 (1H, d), 4.85 (1H, d), 4.35 (1H, m), 4.07 (1H, q), 2.80 (2H, m), 2.31 (1H, m), 2.11 (1H, m), 0.65 (4H, m).

EXAMPLE 20

[1S-(1α,2β,3β,4α)]-4-[7-(Butylamino)-5-(propylthio)-3H-1,2,3-triazolo[4,5-d]pyrimidin-3-yl]-2,3-dihydroxy-N-(2-hydroxyethyl)-cyclopentanecarboxamide (a) [3aR-(3aα,4α,6α,6aα)]-6-[7-Chloro-5-(propylthio)-3H-1,2,3-triazolo[4,5-d]pyrimidin-3-yl]-N-(2-hydroxyethyl)-tetrahydro-2,2-dimethyl-4H-cyclopenta-1,3-dioxole-4-carboxamide N,N-Diisopropylethylamine (0.52 ml) was added to a solution of ethanolamine (66 ml), bromo-tris-pyrrolidino-phosphonium hexafluorophosphate (0.56 g) and the product of Example 1 step (g) (0.45 g) in DMF (15 ml). The reaction mixture was stirred at room temperature for 1 hour then concentrated. Chromatography (SiO$_2$, ethyl acetate as eluant) gave the subtitle compound (0.18 g).

MS (APCI) 494 (M+H$^+$, 100%).

(b) [1S-(1α,2β,3β,4α)]-4-[7-(Butylamino)-5-(propylthio)-3H-1,2,3-triazolo[4,5-d]pyrimidin-3yl]-2,3-dihydroxy-N-(2-hydroxyethyl)-cyclopentanecarboxamide Prepared according to the method of Example 1 step (i) using the product of step (a) (55 mg).

MS (APCI) 454 (M+H$^+$, 100%); NMR δH (d$_6$-DMSO) 9.00 (1H, t), 7.94 (1H, t), 5.13 (1H, d), 5.00–4.93 (2H, m), 4.68 (1H, t), 4.45–4.11 (1H, m), 4.10 (1H, m), 3.53–3.38 (4H, m), 3.17–3.07 (4H, m), 2.78 (1H, m), 2.33–2.24 (2H, m), 1.74–1.57 (4H, m), 1.38–1.30 (2H, m), 0.99 (3H, t), 0.91 (3H, t).

EXAMPLE 21

[1S-(1α,2β,3β,4α)]-4-[7-(Butylamino)-5-(propylthio)-3H-1,2,3-triazolo[4,5-d]yrimidin-3-yl]-2,3-dihydroxy-N-(3-hydroxy-2,2-difluoropropyl)-cyclopentanecarboxamide (a) [3aR-(3aα,4α,6α,6aα)]-6-[7-(Butylamino)-5-(propylthio)-3H-1,2,3-triazolo[4,5-d]pyrimidin-3-yl]-N-(3-hydroxy-2,2-difluoropropyl)-tetrahydro-2,2-dimethyl-4H-cyclopenta-1,3-dioxole-4-carboxamide Prepared according to the method of Example 20 step (a) using 2,2-difluoro-1,3-propanediamine and was isolated as a by-product.

MS (APCI) 544 (M+H$^+$, 100%).

(b) [1S-(1α,2β,3β,4α)]-4-[7-(Butylamino)-5-(propylthio)-3H-1,2,3-triazolo[4,5-d]pyrimidin-3-yl]-2,3-dihydroxy-N-(3-hydroxy-2,2-difluoropropyl)cyclopentane-carboxamide Prepared according to the method of Example 1 step (i) using the product of step (a).

MS (APCI) 504 (M+H$^+$, 100%); NMR δH (d$_6$-DMSO) 9.00 (1H, t), 8.32 (1H, t), 8.46 (1H, t), 5.18 (1H, d), 5.04 (1H, d), 5.01–4.92 (1H, m), 4.48–4.39 (1H, m), 4.14–4.10 (1H, m), 3.64–3.48 (6H, m), 3.12–3.06 (2H, m), 2.93–2.83 (1H, m), 2.37–2.10 (3H, m), 1.73–1.57 (4H, m), 1.36–1.30 (2H, m), 0.98 (3H, t), 0.90 (3H, t).

EXAMPLE 22

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-(4-hydroxyphenyl)ethyl]-cyclopentanecarboxamide (a) [3aR-(3aα,4α,6α,6aα)]-6-[7-(Butylamino)-5-(propylthio)-3H-1,2,3-triazolo[4,5-d]pyrimidin-3-yl]-N-[2-(4-hydroxyphenyl)ethyl]-tetrahydro-2,2-dimethyl-4H-cyclopenta-1,3-dioxole-4-carboxamide Prepared according to the method of Example 20 step (a) using (4-hydroxyphenyl)ethylamine.

MS (APCI) 570 (M+H$^+$, 100%).

(b) [1S-(1α,2β,3β,4α)]-4-[7-(Butylamino)-5-(propylthio)-3H-1,2,3-triazolo[4,5-d]pyrimidin-3-yl]-2,3-dihydroxy-N-[2-(4-hydroxyphenyl)ethyl]-cyclopentanecarboxamide Prepared according to the method of Example 1 step (i) using the product of step (a).

MS (APCI) 530 (M+H$^+$, 100%);

NMR δ H (d$_6$-DMSO) 9.16 (1H, br s), 8.98 (1H, m), 7.97 (1H, m), 6.99 (2H, d), 6.67 (2H, d), 5.12 (1H, d), 4.97–4.93 (2H, m), 4.42 (1H, m), 4.10 (1H, m), 3.48 (2H, m), 3.26–3.19 (2H, m), 3.13–3.07 (2H, m), 2.78–2.70 (1H, m), 2.60 (2H, t), 2.31–2.24 (2H, m), 1.74–1.58 (4H, m), 1.38–1.31 (2H, m), 0.99 (3H, t), 0.91 (3H, t).

EXAMPLE 23

[1S-(1α,2β,3β,4α)]-4-[7-(Butylamino)-5-[4-(trifluoromethyl)phenylthio]-3H-1,2,3-triazolo[4,5-d]pyrimidin-3-yl]-2,3-dihydroxy-N-(2-hydroxyethyl)-cyclopentanecarboxamide (a) [3aR-(3aα,4α,6α,6aα)]-6-[7-(Butylamino)-5-(propylsulfonyl)-3H-1,2,3-triazolo[4,5-d]pyrimidin-3-yl]-tetrahydro-2,2-dimethyl-4H-cyclopenta-1,3-dioxole-4-carboxylic acid Oxone® (5.0 g) was added to a solution of the product of Example 1 step (f) (1.0 g) in acetonitrile (150 ml)/water (10 ml) and the resulting solution was stirred at room temperature for 3 hours. The solution was then diluted with water (100 ml) and extracted with ethyl acetate (3×75 ml). The combined extracts were dried and concentrated and the residue purified (SiO$_2$, ethyl acetate: methanol, 9:1 as eluant) to give the subtitle compound (0.79 g).

MS (ESI) 467 (M+H$^+$, 100%).

(b) [3aR-(3aα,4α,6α,6aα)]-6-[7-(Butylamino)-5-[4-(trifluoromethyl)phenylthio]-3H-1,2,3-triazolo[4,5-d]pyrimidin-3-yl]-tetrahydro-2,2-dimethyl-4H-cyclopenta-1,3-dioxole-4-carboxylic acid Prepared according to the method of Example 11 step (b) using the product of step (a) and 4-(trifluoromethyl)thiophenol (0.38 g).

MS (ESI) 553 (M+H$^+$, 100%).

(c) [3aR-(3aα,4α,6α,6aα)]-6-[7-(Butylamino)-5-[4-(trifluoromethyl)phenylthio]-3H-1,2,3-triazolo[4,5-d]pyrimidin-3-yl]-N-(2-hydroxyethyl)-tetrahydro-2,2-dimethyl-4H-cyclopenta-1,3-dioxole-4-carboxamide Prepared according to the method of Example 20 step (a) using the product of step (b).

MS (ESI) 596 (M+H$^+$, 100%).

(d) [1S-(1α,2β,3β,4α)]-4-[7-(Butylamino)-5-[4-(trifluoromethyl)phenylthio]-3H-1,2,3-triazolo[4,5-d]pyrimidin-3-yl]-2,3-dihydroxy-N-(2-hydroxyethyl)-cyclopentanecarboxamide Prepared according to the method of Example 1 step (i) using the product of step (a).

MS (APCI) 556 (M+H$^+$, 100%); NMR δH (d$_6$-DMSO) 9.14 (1H, t), 7.94 (1H, m), 7.89 (1H, m), 5.14 (1H, d), 4.99 (1H, d), 4.93 (1H, m), 4.70 (1H, t), 4.38 (1H, m), 4.06 (1H, m), 3.44 (2H, m), 3.18 (4H, m), 2.78 (1H, m), 2.33 (1H, m), 2.17 (1H, m), 1.33 (2H, m), 1.09 (2H, m), 0.76 (3H, t).

EXAMPLE 24

[1S-(1α,2β,3β,4α)]-N-[1-(Aminocarbonyl)-2-(hydroxy)ethyl]-4-[7-(butylamino)-5-(propylthio)-3H-1,2,3-triazolo[4,5-d]pyrimidin-3-yl]-2,3-dihydroxy-cyclopentanecarboxamide (a) [1S-(1α,2β,3β,4α)]-N-[1-(Aminocarbonyl)-2-(hydroxy)ethyl]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-carboxamide Prepared according to the method of example 20, step (a) using the product of example 1 step (g) and (2S)-2-amino-3-hydroxy-propanamide hydrochloride.

MS (APCI) 537 (M+H$^+$, 100%).

(b) [1S-(1α,2β,3β,4α)]-N-[1-(Aminocarbonyl)-2-(hydroxy)ethyl]-4-[7-(butylamino)-5-(propylthio)-3H-1,2,3-triazolo[4,5-d]pyrimidin-3-yl]-2,3-dihydroxy-cyclopentanecarboxamide A solution of the product of step (a) (0.39 g) in methanol (10 ml)/0.1N HCl(aq) (20 ml) was stirred at room temperature for 2 hours. The solution was concentrated and the residue purified (HPLC, Nova-pak® C18 column, 0.1% aqueous ammonium acetate:methanol, gradient elution 50:50 to 0:100 over 15 minutes) to afford the subtitle compound.

MS (APCI) 497 (M+H$^+$, 100%); NMR δH (d$_6$-DMSO): 9.01 (1H, t), 7.89 (1H, d), 7.28 (2H, d), 5.19 (1H, d), 5.09 (1H, d), 4.97 (1H, m), 4.87 (1H, t), 4.38 (1H, m), 4.27 (1H, m), 4.13 (1H, m), 3.59 (2H, m), 3.50 (2H, m), 3.09 (2H, m), 2.94 (1H, m), 2.34–2.26 (2H, m), (2H, m), 1.72 (2H, s), 1.62 (2H, m), 1.36 (1H, m), 0.99 (3H, t), 0.91 (3H, t).

EXAMPLE 25

[1S-[1αa(S*),2β,3β,4α]]-4-[7-(Butylamino)-5-(propylthio)-3H-1,2,3-triazolo[4,5-d]pyrimidin-3-yl]-N-(tetrahydro-3-oxo-isoxazol-4-yl)-2,3-dihydroxy-cyclopentanecarboxamide Prepared according to the method of Example 20 step (a) using the product of Example 2 and D-cycloserine.

Melting point: 209–211° C. (EtOAc);

MS (APCI) 495 (M+H$^+$, 100%); NMR δH (d$_6$-DMSO) 11.53 (1H, s), 9.01 (1H, t), 8.55 (1H, d), 5.16 (1H, d), 5.03 (1H, d), 4.98 (1H, q), 4.78 (1H, m), 4.55 (1H, t), 4.42 (1H, q), 4.11 (1H, m), 3.95 (1H, t), 3.49 (2H, q), 3.10 (2H, m), 2.83 (1H, m), 2.39 (1H, m), 2.27 (1H, m), 1.70 (2H, m), 1.60 (2H, m), 1.34 (2H, m), 0.99 (3H, t), 0.91 (3H, t).

EXAMPLE 26

[1S-[1α(R*),2β,3β,4α]]-4-[7-(Butylamino)-5-(propylthio)-3H-1,2,3-triazolo[4,5-d]pyrimidin-3-yl]-2,3-dihydroxy-N-(2-oxo-pyrrolidin-3-yl)-cyclopentanecarboxamide (a) [1S-[1α(R*),2β,3β,4α]]-6-[7-(Butylamino)-5-(propylthio)-3H-1,2,3-triazolo[4,5-d]pyrimidin-3-yl]-2,3-dihydroxy-tetrahydro-2,2-dimethyl-N-(2-oxo-pyrrolidin-3-yl)-4H-cyclopenta-1,3-dioxole-4-carboxamide Prepared according to the method of Example 20 step (a) using 3-amino-pyrrolidin-2-one hydrochloride (prepared as described in by R. Pellegata, M. Pinza, G. Pifferi, Synthesis 1978, 614).

MS (APCI) 533 (M+H+, 100%).

(b) [1S-[1α(R*),2β,3β,4α]]-4-[7-(Butylamino)-5-(propylthio)-3H-1,2,3-triazoio[4,5-d]pyrimidin-3-yl]-2,3-dihydroxy-N-(2-oxo-pyrrolidin-3-yl)-cyclopentanecarboxamide A solution of the product from step (a) (0.44 g) in trifluoroacetic acid (25 ml)/dichloromethane (25 ml) was stirred at room temperature for 5 hours. The reaction mixture was concentrated and the residue purified by chromatography (HPLC, Nova-pak® C18 column, 0.1% aqueous ammonium acetate:methanol, gradient elution 50:50 to 0:100 over 15 minutes) to afford the title compound (0.16 g).

MS (APCI) 493 (M+H+, 100%); NMR δH (d$_6$-DMSO) 9.00 (1H, t), 8.25 (1H, d), 7.84 (1H, s), 5.05 (1H, br s), 5.21 (1H, br s), 4.98 (1H, m), 4.53 (1H, m), 4.33 (1H, m), 4.09 (1H, m), 3.47 (2H, m), 3.13 (2H, m), 3.08 (2H, m), 2.81 (1H, m), 2.34 (3H, m), 1.78 (1H, m), 1.74 (2H, m), 1.69 (2H, m), 1.60 (2H, m), 0.99 (3H, t), 0.91 (3H, t).

EXAMPLE 27

[1S-[1α(R*),2β,3β,4α]]-4-[7-(Butylamino)-5-(propylthio)-3H-1,2,3-triazolo[4,5-d]pyrimidin-3-yl]-2,3-dihydroxy-N-(2,3-di-oxo-pyrrolidin-3-yl)-cyclopentanecarboxamide (a) [1S-[1α(R*),2β,3β,4α]]-6-[7-(Butylamino)-5-(propylthio)-3H-1,2,3-triazolo[4,5-d]pyrimidin-3-yl]-2,3-dihydroxy-N-(2,5-di-oxo-pyrrolidin-3-yl)-tetrahydro-2,2-dimethyl-4H-cyclopenta-1,3-dioxole-4-carboxamide Prepared according to the method of Example 20 step (a) using 3-amino-2,5-pyrrolidinedione (prepared as described by T Polonski, J. Chem. Soc., 1988, 629).

MS (APCI) 547 (M+H+, 100%).

[1S-[1α(R*),2β,3β,4α]]-4-[7-(Butylamino)-5-(propylthio)-3H-1,2,3-triazolo[4,5-d]pyrimidin-3-yl]-2,3-dihydroxy-N-(2-oxo-pyrrolidin-3-yl)-cyclopentanecarboxamide Prepared according to the method of example 26 step (b) using the product of step (a).

MS (APCI) 507 (M+H+, 100%); NMR δH (d$_6$-DMSO) 11.22 (1H, s), 8.99 (1H, t), 8.63 (1H, d), 5.17 (1H, d), 5.15 (1H, d), 4.99 (1H, m), 4.46 (2H, m), 4.12 (1H, m), 3.49 (2H, m), 3.11 (2H, m), 2.93 (1H, m), 2.77 (1H, m), 2.56 (1H, m), 2.36–2.34 (2H, m), 1.71 (2H, m), 1.64 (2H, m), 1.36 (2H, m), 0.98 (3H, t), 0.91 (3H, t).

EXAMPLE 28

[1S-[1α(R*),2β,3β,4α]]-N-[(Aminocarbonyl)-methyl]-4-[7-(butylamino)-5-(propylthio)-3H-1,2,3-triazolo[4,5-d]pyrimidin-3-yl]-2,3-dihydroxy-cyclopentanecarboxamide Prepared using the method of Example 20 step (a) using aminoacetamide, followed by the method of Example 26 step (b).

MS (APCI) 467 (M+H+, 100%); NMR δH (d$_6$-DMSO) 8.99 (1H, t), 8.08 (1H, d), 7.28 (1H, s), 7.05 (1H, s), 4.98 (1H, m), 4.40 (1H, m), 4.12 (1H, m), 3.66 (2H, m), 3.46 (2H, m), 2.85 (1H, m), 2.38–2.27 (2H, m), 1.74 (2H, m), 1.62 (2H, m), 1.36 (2H, m), 0.99 (3H, t), 0.89 (3H, t).

EXAMPLE 29

[1S-[1α(R*),2β,3β,4α]]-N-[1-(Aminocarbonyl)-2-(4-hydroxyphenyl)ethyl]4-[7-(butylamino)-5-(propylthio)-3H-1,2,3-triazolo[4,5-d]pyrimidin-3-yl]-2,3-dihydroxy-cyclopentanecarboxamide (a) [1S-[1α(R*),2β,3β,4α]]-N-[1-(Aminocarbonyl)-2-(4-hydroxyphenyl)ethyl]-[6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-carboxamide Prepared according to the method of Example 20 step (a) using (S)-α-amino-4-hydroxy-benzenepropanamide.

MS (APCI) 613 (M+H+, 100%).

(b) [1S-[1α(R*),2β,3β,4α]]-N-[1-(Aminocarbonyl)-2-(4-hydroxyphenyl)ethyl]4-[7-(butylamino)-5-(propylthio)-3H-1,2,3-triazolo[4,5-d]pyrimidin-3-yl]-2,3-dihydroxy-cyclopentanecarboxamide Prepared according to the method of Example 26 step (b) using the product of step (a).

MS (APCI) 573 (M+H+, 100%); NMR δ H (d$_6$-DMSO) 9.07 (1H, s), 8.98 (1H, t), 8.61 (1H, t), 8.03 (1H, d), 7.39 (1H, s), 7.07 (1H, s), 7.00 (2H, d), 6.58 (2H, d), 4.92 (1H, m), 4.36 (2H, m), 4.10 (1H, m) 3.90 (2H, m), 3.50 (2H, m), 3.09 (2H, m), 2.86 (2H, m), 2.66 (1H, m), 2.21 (1H, m), 2.06 (1H, m), 1.71 (2H, m), 1.61 (2H, m), 1.36 (2H, m), 0.99 (3H, t), 0.91 (3H, t).

EXAMPLE 30

[1S-[1α(R*),2β,3β,4α]]-N-[1-(Aminocarbonyl)-2-(hydroxy)ethyl]-4-[7-(butylamino)-5-[4-(trifluoromethyl)phenylthio]-3H-1,2,3-triazolo[4,5-d]pyrimidin-3-yl]-2,3-dihydroxy-cyclopentanecarboxamide (a) [3aR-[3aα,4α,4α,6α,6aα]]-6-[7-(butylamino)-5-[4-(trifluoromethyl)phenylthio]-3H-1,2,3-triazolo[4,5-d]pyrimidin-3-yl]-tetrahydro-2,2-dimethyl-4H-cyclopenta-1,3-dioxole-4-carboxylic acid (0.38 g)

Prepared according to the method of Example 11 (b) using the product of example 23, step (a) and 4-(trifluoromethyl) thiophenol.

MS (ESI) 553 (M+H+, 100%).

(b) [1S[1α(R*),2β,3β,4α]]-N-[1-(Aminocarbonyl)-2-(hydroxy)ethyl]-4-[7-(butylamino)-5-[4-(trifluoromethyl) phenylthio]-3H-1,2,3-triazolo[4,5-d]pyrimidin-3-yl]-2,3-dihydroxy-cyclopentanecarboxamide Prepared according to the method of Example 20 step (a), followed by the method of Example 26 step (b) using the product of step (a) above.

MS (ESI) 599 (M+H+, 100%); NMR δH (d$_6$-DMSO) 8.73 (1H, s), 7.80 (4H, d), 7.56 (1H, d), 6.89 (2H, br s), 4.94 (1H, m), 4.81 (1H, d), 4.72 (1H, d), 4.71 (1H, t), 4.42 (1H, m), 4.31 (1H, m), 4.20 (1H, m), 3.69 (2H, m), 3.61 (2H, m), 2.99 (1H, m), 2.51–2.25 (2H, m), 1.43 (2H, br s), 1.21 (2H, br s), 0.84 (3H, t).

EXAMPLE 31

[1S-[1α(1R*,2S*),2β,3β,4α]]-N-[1-(Aminocarbonyl)-2-hydroxy)propyl]-4-[7-(butylamino)-5-(propylthio)-3H-1,2,3-triazolo[4,5-d]pyrimidin-3-yl]-2,3-dihydroxycyclopentanecarboxamide (a) [1S-[1α(1R*,2S*),2β,3β,4α]]-N-[1-(Aminocarbonyl)-2-(hydroxy)propyl]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-carboxamide Prepared according to the method of Example 20 step (a) using [S-(S*,S*)]-2-amino-3-hydroxy-butanamide.

MS (APCI) 551 (M+H+, 100%).

(b) [1S-[1α(1R*,2S*),2β,3β,4α]]-N-[1-(Aminocarbonyl)-2-(hydroxy)propyl]-4-[7-(butylamino)-5-(propylthio)-3H-1,2,3-triazolo[4,5-d]pyrimidin-3-yl]-2,3-dihydroxy-cyclopentanecarboxamide Prepared according to the method of Example 26 step (b) using the product of step (a) and purified by chromatography (HPLC, Nova-pak® C18 column, 0.1% aqueous ammonium acetate:methanol, gradient elution 30:70 to 0:100 over 15 minutes).

MS (APCI) 511 (M+H$^+$, 100%). NMR δH (d$_6$-DMSO) 8.98 (1H, t), 7.68 (1H, d), 7.15 (2H, d), 5.18 (1H, d), 5.08 (1H, d), 4.97(1H, m), 4.84 (1H, d), 4.40–4.38 (1H, m), 4.17 (1H, d), 4.14 (1H, d), 4.05 (1H, br s), 3.49 (2H, q), 3.12–3.08 (2H, m), 3.06–3.00 (1H, m), 2.40 (1H, m), 2.26 (1H, m), 1.69 (2H, m), 1.63 (2H, m), 1.34 (2H, m), 1.02 (3H, sext), 0.99 (3H, t), 0.91 (3H, t).

EXAMPLE 32

[1S-[1α,2β,3β,4α]]-N-[2-(Aminocarbonyl)ethyl]-4-[7-(butylamino)-5-(propylthio)-3H-1,2,3-triazolo[4,5-d]pyrimidin-3-yl]-2,3-dihydroxy-cyclopentanecarboxamide (a) [3aR-[3aα,4α,6α,6α]]-N-[2-(Aminocarbonyl)ethyl]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-carboxamide Prepared according to the method of example 20 step (a) using 3-amino-propanamide.

MS (APCI) 521 (M+H$^+$, 100%).

(b) [1S-[1α,2β,3β,4α]]-N-[2-(Aminocarbonyl)ethyl]-4-[7-(butylamino)-5-(propylthio)-3H-1,2,3-triazolo[4,5-d]pyrimidin-3-yl]-2,3-dihydroxy-cyclopentanecarboxamide Prepared according to the method of Example 26 step (b) using the product of step (a) above.

MS (APCI) 481 (M+H$^+$, 100%); NMR δH (d$_6$-DMSO) 8.99 (1H, t), 7.97 (1H, t), 7.33 (1H, br s), 6.84 (1H, br s), 5.05 (1H, br s), 4.97–4.92 (1H, m), 4.43–4.39 (1H, m), 4.09 (1H, m), 3.52–3.46 (2H, m), 3.28–3.22 (2H, m), 3.12–3.07 (2H, m), 2.75–2.72 (1H, m), 2.31–2.20 (4H, m), 1.73–1.55 (4H, m), 1.37–1.31 (2H, m), 1.01–0.88 (6H, m).

EXAMPLE 33

[1S-[1α,2β,3β,4α]]-4-[7-(Butylamino)-5-(propylthio)-3H-1,2,3-triazolo[4,5-d]pyrimidin-3-yl]-2,3-dihydroxy-N-[2-(methylaminocarbonyl)-ethyl]-cyclopentanecarboxamide (a) [3aR-[3aα,4α,6α,6α]]-N-[6-[7-(Butylamino)-5-(propylthio)-3H-1,2,3-triazolo[4,5-d]pyrimidin-3-yl]-tetrahydro-2,2-dimethyl-4H-cyclopenta-1,3-dioxole-4-carbonyl]-β-alanine, 1,1-dimethylethyl ester Prepared according to the method of Example 20 step (a) using β-alanine, 1,1-dimethylethyl ester.

MS (APCI) 578 (M+H$^+$, 100%).

(b) [1S-[1α,2β,3β,4α]]-N-[4-[7-(Butylamino)-5-(propylthio)-3H-1,2,3-triazolo[4,5-d]pyrimidin-3-yl]-2,3-dihydroxycyclopentyl-4-carbonyl]-β-alanine Prepared according to the method of Example 26 step (b) using the product of step (a) above.

MS (APCI) 482 (M+H$^+$, 100%).

(c) [1S-[1α,2β,3β,4α]]-4-[7-(Butylamino)-5-(propylthio)-3H-1,2,3-triazolo[4,5-d]pyrimidin-3-yl]-2,3-dihydroxy-N-[2-(Methylaminocarbonyl)ethyl]-cyclopentanecarboxamide Prepared according to the method of example 20 step (a) using the product of step (b) and methylamine.

MS (APCI) 495 (M+H$^+$, 100%); NMR δH (d$_6$-DMSO) 9.01 (1H, t), 8.00–7.98 (1H, m), 7.81 (1H, m), 5.13 (1H, d), 5.01 (1H, d), 4.96–4.92 (1H, m), 4.44–4.40 (1H, m), 4.12–4.08 (1H, m), 3.48 (2H, q), 3.26 (2H, q); 3.13–3.07 (2H, m), 2.76–2.74(1H, m), 2.55 (3H, d), 2.31–2.21 (4H, m), 1.70 (2H, sext), 1.62 (2H, m), 1.34 (2H, sext), 0.99 (3H, t), 0.91 (3H, t).

EXAMPLE 34

[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentanecarboxylic acid a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxylic acid A mixture of the product of example 1, step f) (413 mg), (1R-trans)-2-phenylcyclopropylamine, [R-(R*,R*)]-2,3-dihydroxybutanedioate (1:1) (prepared as described by L. A. Mitscher et al., J. Med. Chem. 1986, 29, 2044) (283 mg) and triethylamine (1.1 ml) in dichloromethane (6 ml) was stirred at room temperature for 4 hours. The reaction mixture was concentrated and the residue purified (SiO$_2$, ethyl acetate then methanol:ethyl acetate 1:4 as eluant) to afford the subtitle compound (390 mg).

MS (APCI) 511 (M+H$^+$, 100%).

b) [1S-[1α,2β,3α,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentanecarboxylic acid Prepared according to the method of example 1, step i) using the product of step a).

MS (APCI) 471 (M+H$^+$, 100%); NMR δH (d$_6$-DMSO) 9.34 and 8.98 (1H, d), 7.31–7.15 (5H, m), 5.18 (2H, br s), 5.02 (1H, m), 4.42 (1H, m), 4.22 (1H, m), 3.22 (1H, m), 3.17–2.75 (3H, m), 2.50–2.08 (3H, m), 1.78–1.25 (4H, m), 0.81 and 0.99 (3H, t).

EXAMPLE 35

[1S-[1α,2β,3β,4α(1S*,2R*)]]-2,3-Dihydroxy-4-[7-[(2-phenylcyclopropyl)amino]- 5-(propylthio)-3H-1,2,3-triazolo[4,5-d]pyrimidin-3-yl]-cyclopentanecarboxamide a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide Prepared according to the method of example 1, step h) using the product of example 34, step a).

MS (APCI) 510 (M+H$^+$, 100%).

b) [1S-[1α,2β,3β,4α(1S*,2R*)]]-2,3-Dihydroxy-4-[7-(2-phenylcyclopropylamino)]-5-(propylthio)-3H-1,2,3-triazolo[4,5-d]pyrimidin-3-yl]-cyclopentanecarboxamide Prepared according to the method of example 1, step i) using the product of step a).

MS (APCI) 470 (M+H$^+$, 100%);

NMR δH (d$_6$-DMSO) 9.32 and 8.92 (1H, d), 7.34 (1H, m), 7.29 (2H, m), 7.18 (3H, m), 6.89 (1H, s), 5.09 (1H, d), 4.97 (2H, m), 4.42 (1H, m), 4.14 (1H, m), 3.21 and 3.88 (1H, m), 2.96 (1H, m), 1.51 and 1.70 (1H, m), 1.32 (1H, m), 0.82 and 1.00 (3H, t).

EXAMPLE 36

[1S-(1α,2β,3β,4α)]-2,3-Dihydroxy-4-[7-(cyclobutylamino)-5-(propylthio)-3H-1,2,3-triazolo[4,5-d]pyrimidin-3-yl]-cyclopentanecarboxylic acid a) [3aR-(3aα,4α,6α,6aα)]-6-[7-(Cyclobutylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step g) using the product of example 1, step f) and cyclobutylamine.

MS (APCI) 449 (M+H$^+$, 100%).

b) [1S-(1α,2β,3β,4α)]-4-[7-(Cyclobutylamino)-5-(propylthio)-3H-1,2,3-triazolo[4,5-d]pyrimidin-3-yl]-2,3-dihydroxy-cyclopentanecarboxylic acid Prepared according to the method of example 1, step i) using the product of step a).

MS (APCI) 409 (M+H$^+$, 100%); NMR δH (d$_6$-DMSO) 0.95–1.01(3H, m), 1.64–1.90 (4H, m), 2.11–2.45 (6H, m), 2.75–2.82 (1H, m), 3.03–3.14 (2H, m), 4.19–4.22 (1H, m), 4.38–4.45 (1H, m), 4.61–4.69 (1H, m), 4.95–5.03 (1H, m), 9.22 (1H, d).

EXAMPLE 37

[1S-(1α,2β,3β,4α)]-4-[7-(Cyclobutylamino)-5-(propylthio)-3H-1,2,3-triazolo[4,5-d]pyrimidin-3-yl]-2,3-dihydroxy-cyclopentanecarboxamide Sieber amide resin (2.0 g) was washed sequentially with a 20% solution of piperidine in N,N-dimethylformamide (10 ml), N,N-dimethylformamide (DMF) (3×10 ml), dichloromethane (3×10 ml) and diethyl ether (1×10 ml). To the resin was added a solution of the product from example 36 step b) (0.25 g) in dichloromethane (10 ml) and N,N'-diisopropylcarbodiimide (0.13 g). The mixture was shaken for 18 hours then filtered and the residue washed with dichloromethane and a solution of trifluoroacetic acid in dichloromethane (2%, 4×10 ml). The filtrate was evaporated to dryness and the residue purified by chromatography (HPLC, Nova-pak® C18 column, 0.1% aqueous ammonium acetate:methanol, gradient elution 40:60 to 0:100 over 20 minutes) to afford the title compound (0.095 g).

MS (APCI) 408 (M+H$^+$, 100%); NMR δH (d$_6$-DMSO) 0.96–1.02 (3H, m), 1.64–1.76 (4H, m), 2.08–2.39 (6H, m), 2.72–2.80 (1H, m), 3.05–3.15 (1H, m), 4.61–4.69 (1H, m), 4.91–4.99 (2H, m), 5.11 (1H, d), 6.91 (1H,s), 7.36 (1H, s), 9.23(1H, d).

EXAMPLE 38

[1S-(1α,2β,3β,4α)]-4-[7-(Cyclopropylamino)-5-[[4-(trifluoromethyl)phenyl]thio]-3H-1,2,3-triazolo[4,5-d]pyrimidin-3-yl]-2,3-dihydroxy-cyclopentanecarboxylic acid.

Prepared according to the method of example 11, step b) using the product of example 19, step a) and 4-(trifluoromethyl)thiophenol, followed by the method of example 1 step i).

MS (EI) 497 (M+H$^{30}$ ); NMR δH (d$_6$-DMSO) 9.32–9.22 (2H, d), 7.95–7.92 (2H, d), 7.81–7.78 (2H, d), 4.98–4.86 (1H, m) 4.40–4.34 (1H, m), 4.18–4.10 (1H, m), 2.76–2.66 (2H, m), 2.5–2.1(2H, t), 0.89–0.50 (4H, m).

EXAMPLE 39

[1S-(1α,2β,3β,4α)]-4-[7-(Cyclopropylamino)-5-[[4-(trifluoromethyl)phenyl]thiol-]-3H-1,2,3-triazolo[4,5-d]pyrimidin-3-yl]-2,3-dihydroxy-cyclopentanecarboxamide Prepared according to the method of example 1, step h) using the product of example 38, followed by the method of example 1, step i).

MS (EI) 496 (M+H$^+$); NMR δH (d$_6$-DMSO) 9.25 (1H, d), 7.95–7.92 (2H, d),7.81–7.78 (2H, d), 7.37 (1H, s) 6.94 (1H, s), 5.15 (1H, d), 4.96 (1H, d), 4.98–4.86 (1H, m), 4.40–4.34 (1H, m), 4.13–4.02 (1H, m), 2.76–2.66 (2H, m), 2.51–2.10 (2H, t), 0.89–0.50 (4H, m).

EXAMPLE 40

[1S-(1α,2β,3β,4α)]-4-[7-(Butylamino)-5-[(3,3,3-trifluoropropyl)thio]-3H-1,2,3-triazolo[4,5-d]pyrimidin-3-yl]-2,3-dihydroxy-cyclopentanecarboxylic acid a) [3aR-(3aα,4α,6α,6aα)]-6-[[5-Amino-6-chloro-2-[(3,3,3-trifluoropropyl)thio]-4-pyrimidinyl]amino]-tetrahydro-2,2-dimethyl-4H-cyclopenta-1,3-dioxole-4-carboxylic acid Prepared according to the method of example 1, step e) using 4,6-dichloro-5-nitro-2-(3,3,3-trifluoropropylthio)pyrimidine (Prepared as described in WO 9703084).

b) (3aR-(3aα,4α,6α,6aα)]-6-[7-Chloro-5-[(3,3,3-trifluoropropyl)thio]-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step f) using the product of step a).

MS (EI, negative ionization) 466 (M–H$^+$).

c) [3aR-(3aα,4α,6α,6aα)]-6-[7-(Butylamino)-5-[(3,3,3-trifluoropropyl)thio]-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step g) using the product of step b) and butylamine.

MS (APCI) 505 (M+H$^+$, 100%).

d) [1S-(1α,2β,3β,4α)]-4-[7-(Butylamino)-5-[(3,3,3-trifluoropropyl)thio]-3H-1,2,3-triazolo[4,5-d]pyrimidin-3-yl]-2,3-dihydroxy-cyclopentanecarboxylic acid.

Prepared according to the method of example 1, step i) using the product of step c).

MS (APCI) 465 (M+H$^+$); NMR δH (d$_6$-DMSO) 9.10 (1H, t), 4.97–4.93 (1H, m), 4.45 (1H, br s), 4.2 (1H, br s), 3.55–3.50 (2H, m), 3.33–3.22 (1H, m), 2.80–2.55 (2H, m), 2.35–2.33 (2H, m), 1.71 (2H, s), 1.65–1.52 (2H, m), 1.4–1.3 (2H, m), 0.90 (1H t).

EXAMPLE 41

[1S-(1α,2β,3β,4α)]-4-[7-(Butylamino)-5-[(3,3,3-trifluoropropyl)thio]-3H-1,2,3-triazolo[4,5-d]pyrimidin-3-yl]-2,3-dihydroxy-cyclopentanecarboxamide Prepared according to the method of example 1, step h) using the product of example 40, step c), followed by the method of example 1, step i).

MS (EI) 464 (M+H$^+$); NMR δH (d$_6$-DMSO) 9.10 (1H, t), 7.4 (1H s), 6.93 (1H s), 5.1 (1H, d), 5.00–4.93 (2H, m), 4.12–4.00 (1H, m), 3.56–3.46 (3H, m), 3.35–3.25 (2H, t), 2.82–2.60 (3H, m), 2.4–2.15 (2H, m), 1.7–1.5 (2H m), 1.4–1.3 (2H m) 0.92–0.88 (3H t).

EXAMPLE 42

[1S-(1α,2β,3β,4α)]-2,3-Dihydroxy-4-[7-[(1,4-dimethylpentyl)amino]-5-(propylthio)-3H-1,2,3-triazolo[4,5-d]pyrimidin-3-yl]-cyclopentanecarboxylic acid a) [3aR-(3aα,4α,6α,6aα)]-Tetrahydro-2,2-dimethyl-6-[7-[(1,4-dimethylpentyl)amino]-5-(propylthio)-3H-1,2,3-triazolo[4,5-d]pyrimidin-3-yl]-4H-cyclopenta-1,3-dioxole-4-carboxylic acid Prepared according to the method of example 1, step g) using the product of example 1, step f) and 1,4-dimethylpentylamine.

MS (APCI) 493 (M+H$^+$, 100%).

b) [1S-(1α,2β,3β,4α)]-2,3-Dihydroxy-4-[7-[(1,4-dimethylpentyl)amino]-5-(propylthio)-3H-1,2,3-triazolo[4,5-d]pyrimidin-3-yl]-cyclopentanecarboxylic acid Prepared according to the method of example 1, step i) using the product of step a).

MS (APCI) 493 (M+H$^+$, 100%); NMR δH (d$_6$-DMSO) 0.83–0.86 (6H, m), 0.97–1.00 (3H, t), 1.20–1.25 (4H, m), 1.51–1.54 (2H, m), 1.67–1.72 (3H, m), 2.33–2.40 (2H, m), 2.72–2.76 (1H, m), 3.06–3.10 (2H, m), 4.20–4.46 (3H, m), 4.95–5.01 (2H, m), 8.73 (1H, d)

EXAMPLE 43

[1S-(1α,2β,3β,4α)]-2,3-Dihydroxy-4-[7-[(1,4-dimethylpentyl)amino]-5-(propylthio)-3H-1,2,3-triazolo[4,5-d]pyrimidin-3-yl]-cyclopentanecarboxamide a) [3aR-(3aα,4α,6α,6aα)]-Tetrahydro-2,2-dimethyl-6-[7-[(1,4-dimethylpentyl)amino]-5-(propylthio)-3H-1,2,3-triazolo[4,5-d]pyrimidin-3-yl]-4H-cyclopenta-1,3-dioxole-4-carboxamide Prepared according to the method of example 20, step a) using the product of example 42, step a) and a solution of ammonia in acetonitrile.

MS (APCI) 479 (M+H+, 100%).

b) [1S-(1α,2β,3β,4α)]-2,3-Dihydroxy-4-[7-[(1,4-dimethylpentyl)amino]-5-(propylthio)-3H-1,2,3-triazolo[4,5-d]pyrimidin-3-yl]-cyclopentanecarboxamide Prepared according to the method of example 1, step i) using the product of step a).

MS (APCI) 452 (M+H+, 100%); NMR δH (d$_6$-DMSO) 0.82–0.86 (6H, m), 0.98 (3H, t), 1.18–1.25 (5H, m), 1.49–1.72 (5H, m), 2.24–2.34 (2H, m), 2.75–2.76 (1H, m), 3.06–3.10 (2H, m), 4.11–4.14 (2H, m), 4.93–5.00 (2H, m), 5.13 (1H, d), 6.92 (1H, s), 7.38 (1H, s), 8.82 (1H, d).

EXAMPLE 44

[1S-(1α,2β,3β,4α)]-2,3-Dihydroxy-4-[7-[(1-methylbutyl)amino]-5-(propylthio)-3H-1,2,3-triazolo[4,5-d]pyrimidin-3-yl]-cyclopentanecarboxylic acid a) [3aR-(3aα,4α,6α,6aα)]-Tetrahydro-2,2-dimethyl-6-[7-[(1-methylbutyl)amino]-5-(propylthio)-3H-1,2,3-triazolo[4,5-d]pyrimidin-3-yl]-4H-cyclopenta-1,3-dioxole-4-carboxylic acid Prepared according to the method of example 1, step g) using the product of example 1, step f) and 1-methylbutylamine.

NMR δH (d$_6$-DMSO) 0.81–0.90 (5H, m), 1.03–1.11 (7H, m), 1.21–1.44 (8H, m), 1.55 (3H, s), 1.75–1.80 (3H, m), 2.50–2.59 (1H, m), 2.77–2.84 (2H, m), 2.99–3.06 (2H, m), 3.14–3.23 (2H, m), 4.07–4.18 (1H, m), 5.12–5.14 (1H, m), 5.64–5.66 (2H, m), 7.76 (1H, d)

b) 1S-(1α,2β,3β,4α)]-2,3-Dihydroxy-4-[7-[(1-methylbutyl)amino]-5-(propylthio)-3H-1,2,3-triazolo[4,5-d]yrimidin-3-yl]-cyclopentanecarboxylic acid Prepared according to the method of example 1, step i) using the product of step a).

MS (APCI) 425 (M+H+, 100%); NMR δH (d$_6$-DMSO) 0.84–0.90 (3H, m), 0.98 (3H, t), 1.19–1.35 (5H, m), 1.48–1.52 (2H, m), 1.62–1.73 (4H, m), 2.35–2.46 (2H, m), 2.76–2.80 (1H, m), 3.04–3.10 (2H, m), 4.20–4.22 (1H, m), 4.39–4.43 (2H, m), 4.97–5.03 (1H, m), 8.79 (1H, d)

EXAMPLE 45

[1S-(1α,2β,3β,4α)]-2,3-Dihydroxy-4-[7-[(1-methylbutyl)amino]-5-(propylthio)-3H-1,2,3-triazolo[4,5-d]pyrimidin-3-yl]-cyclopentanecarboxamide a) [3aR-(3aα,4α,6α,6aα)]-Tetrahydro-2,2-dimethyl-6-[7-[(1-methylbutyl)amino]-5-(propylthio)-3H-1,2,3-triazolo[4,5-d]pyrimidin-3-yl]-4H-cyclopenta-1,3-dioxole-4-carboxamide Prepared according to the method of example 20, step a) using the product of example 44, step a) and a solution of ammonia in acetonitrile.

MS (APCI) 479 (M+H+, 100%).

b) [1S-(1α,2β,3β,4α)]-2,3-Dihydroxy-4-[7-[(1-methylbutyl)amino]-5-(propylthio)-3H-1,2,3-triazolo[4,5-d]pyrimidin-3-yl]-cyclopentanecarboxamide Prepared according to the method of example 1, step i) using the product of step a).

MS (APCI) 452 (M+H+, 100%); NMR δH (d$_6$-DMSO) 0.82–0.86 (6H, m), 0.98 (3H, t), 1.18–1.25 (5H, m), 1.49–1.72 (5H, m), 2.24–2.34 (2H, m), 2.75–2.76 (1H, m), 3.06–3.10 (2H, m), 4.11–4.14 (2H, m), 4.93–5.00 (2H, m), 5.13 (1H, d), 6.92 (1H, s), 7.38 (1H, s), 8.82 (1H, d)

EXAMPLE 46

[1S-(1α,2β,3β,4α)]-2,3-Dihydroxy-4-[7-[(1,3-dimethylbutyl)amino]-5-(propylthio)-3H-1,2,3-triazolo[4,5d]pyrimidin-3-yl]-cyclopentanecarboxylic acid a) [3aR-(3aα,4α,6α,6aα)]-Tetrahydro-2,2-dimethyl-6-[7-[(1,3-dimethylbutyl)amino]-5-(propylthio)-3H-1,2,3-triazolo[4,5-d]pyrimidin-3-yl]-4H-cyclopenta-1,3-dioxole-4-carboxylic acid Prepared according to the method of example 1, step g) using the product of example 1, step f) and 1,3-dimethylbutylamine.

MS (APCI) 479 (M+H+, 100%).

b) [1S-(1α,2β,3β,4α)]-2,3-Dihydroxy-4-[7-[(1,3-dimethylbutyl)amino]-5-(propylthio)-3H-1,2,3-triazolo[4,5-d]pyrimidin-3-yl]-cyclopentanecarboxylic acid Prepared according to the method of example 1, step i) using the product of step a).

MS (APCI) 439 (M+H+, 100%); NMR δH (d$_6$-DMSO) 0.83–0.91 (6H, m), 0.95–1.00 (3H, t), 1.18–1.33 (4H, m), 1.58–1.73 (4H, m), 2.30–2.40 (3H, m), 2.67–2.72 (1H, m), 3.02–3.10 (2H, m), 4.17–4.20 (1H, m), 4.38–4.48 (2H, m), 4.94–5.00 (1H, m), 8.78(1H, d).

EXAMPLE 47

[1S-(1α,2β,3β,4α)]-2,3-Dihydroxy-4-[7-[(1,3-dimethylbutyl)amino]-5-(propylthio)-3H-1,2,3-triazolo[4,5-d]pyrimidin-3-yl]-cyclopentanecarboxamide Prepared according to the method of example 1, step h) using the product from example 46, step b).

MS (APCI) 438 (M+H+, 100%); NMR δH (d$_6$-DMSO) 0.83–0.91 (6H, m), 0.98 (3H, t), 1.18–1.34 (4H, m), 1.58–1.74 (4H, m), 2.20–2.36 (2H, m), 2.72–2.76 (1H, m), 3.06–3.11 (2H, m), 4.10–4.14 (1H, m), 4.39–4.49 (2H, m), 4.93–4.98 (2H, m), 5.11 (1H, d), 6.91 (1H, s), 7.37 (1H, s), 8.79 (1H, d).

EXAMPLE 48

[1S-(1α,2β,3β,4α)]-4-[7-(Ethylamino)-5-(propylthio)-3H-1,2,3-triazolo[4,5-d]pyrimidin-3-yl]-2,3-dihydroxy-cyclopentanecarboxylic acid Prepared according to the method of example 1, step g) using the product of example 1, step f) and ethylamine, followed by the method of example 1, step i).

MS (APCI) 381(M–H+); NMR δH (d$_6$-DMSO) 8.98 (1H, t), 5.04–4.99 (1H, m), 4.43–4.39 (1H, m), 4.33–4.22 (1H, m), 3.53–3.50 (2H, m), 3.11–3.05 (2H, m), 2.85–2.75 (1H, m), 2.35–2.25(1H, m), 1.80–1.60 (2H, t),1.30–1.15 (3H, t),1.00–0.92 (3H, t).

EXAMPLE 49

[1S-(1α,2β,3β,4α)]-4-[7-(4-Hydroxybutylamino)-5-(propylthio)-3H-1,2,3-triazolo[4,5-d]pyrimidin-3-yl]-2,3-dihydroxy-cyclopentanecarboxylic acid a) [3aR-(3aα,4α,6α,6aα)]-Tetrahydro-6-[7-(4-hydroxybutylamino)-5-(propylthio)-3H-1,2,3-triazolo[4,5-d]pyrimidin-3-yl]-2,2-dimethyl-4H-cyclopenta-1,3-dioxole-4-carboxylic acid Prepared according to the method of example 1, step g) using the product of example 1, step f) and 4-aminobutanol.

MS (APCI) 467 (M+H+, 100%).

b) [1S-(1α,2β,3β,4α)]-4-[7-(4-Hydroxybutylamino)-5-(propylthio)-3H-1,2,3-triazolo[4,5-d]pyrimidin-3-yl]-2,3-dihydroxy-cyclopentanecarboxylic acid Prepared according to the method of example 1, step i) using the product of step a).

MS (APCI) 427 (M+H+, 100%); NMR δH (d$_6$-DMSO) 9.00 (1H, t), 5.19 (2H, br s), 5.00 (1H, q), 4.43–4.39 (2H, m), 4.22 (1H, t), 3.49 (2H, q), 3.41(2H, q), 3.13–3.03(2H, m), 2.85–2.78 (1H, m), 2.49–2.31 (2H, m), 1.74–1.59 (4H, m), 1.52–1.45 (2H, m), 0.99 (3H, t).

EXAMPLE 50

[1S-(1α,2β,3β,4α)]4-[7-(Cyclopentylamino)-5-(propylthio)-3H-1,2,3-triazolo[4,5-d]pyrimidin-3-yl]-2,3-dihydroxy-cyclopentanecarboxylic acid Prepared according to the method of example 1, step g) using the product of example 1, step f) and cyclopentylamine, followed by the method of example 1, step i).

MS (APCI) 423 (M+H, 100%); NMR δH (d$_6$-DMSO) 9.98 (1H, d), 5.23 (1H, bs), 4.97 (2H, q), 4.37–4.21 (1H, m), 3.22–3.01 (2H, m), 2.83 (1H, m), 2.50–2.20 (1H, m), 2.10–1.90 (2H, m), 1.83–1.51 (8H, m), 0.98 (3H, t).

EXAMPLE 51

[1S-(1α,2β,3β,4α)]-4-[5-[(4-Bromophenyl)thio]-7-(butylamino)-3H-1,2,3-triazolo[4,5-d]yrimidin-3-yl]-2,3-dihydroxy-cyclopentanecarboxylic acid Prepared according to the method of example 11, step b) using the product of Example 13, step a) and 4-bromothiophenol.

MS (ESI) 525, 523 (M+H$^+$, 100%); NMR δH (d$_6$-DMSO) 9.15–9.11 (1H, t), 7.64–7.55 (4H, 2d), 5.24–5.20 (1H, m), 5.01 (1H, m), 4.36–4.33 (1H, m), 4.19–4.16 (1H, m), 3.24–3.17 (2H, m), 2.92–2.84 (1H, m), 2.26–2.21 (1H, m), 1.38–1.31 (2H, m), 1.19–1.12 (2H, m), 0.87–0.80 (3H, t).

EXAMPLE 52

[1S-(1α,2β,3β,4α)]-4-[7-[(6-Hydroxyhexyl)amino]-5-(propylthio)-3H-1,2,3-triazolo[4,5-d]pyrimidin-3-yl]-2,3-dihydroxy-cyclopentanecarboxylic acid Prepared according to the method of example 1, step g) using the product of example 1, step f) and 6-amino-1-hexanol, followed by the method of example 1, step i).

MS (APCI) 455 (M+H$^+$); NMR δH (d$_6$-DMSO) 12.44 (1H, s), 9.00 (1H, s), 5.20–5.15 (2H, m), 5.05–4.95 (1H, m), 4.55–4.3 (2H, m), 4.25–4.2 (1H, m), 3.50–3.40 (2H, m), 3.40–3.30 (2H, m), 3.15–3.05 (1H, t), 2.85–2.75 (1H, t), 2.5–2.35 (1H, m), 1.75–1.6 (2H, m), 1.64–1.52 (2H, n), 2.45–2.25 (1H, m), 1.00 (1H, t).

EXAMPLE 53

[1S-[1α,2β,3β,4α(trans)]]-2,3-Dihydroxy-4-[5-[[4-(trifluoromethyl)phenyl]thio]-7-[(2-phenylcyclopropyl)amino]-3H-1,2,3-triazolo[4,5-d]pyrimidin-3-yl]-cyclopentanecarboxylic acid a) [3aR-(3aα,4α,6α(trans),6aα]]-Tetrahydro-2,2-dimethyl-6-[7-[(2-phenylcyclopropyl)amino]-5-(propylsulfonyl)-3H-1,2,3-triazolo[4,5-d]pyrimidin-3-yl]-4H-cyclopenta-1,3-dioxole-4-carboxylic acid Prepared according to the method of example 11, step a) using the product of example 5, step a).

MS (APCI) 543 (M+H$^+$, 100%).

b) [3aR-[3aα,4α,6α(trans),6aα]]-Tetrahydro-2,2-dimethyl-6-[5-[[4-(trifluoromethyl)phenyl]thio]-7-[(2-phenylcyclopropyl)amino]-3H-1,2,3-triazolo[4,5-d]pyrimidin-3-yl]-4H-cyclopenta-1,3-dioxole-4-carboxylic acid Prepared according to the method of example 11, step b) using the product of step a) and 4-trifluoromethylthiophenol.

MS (APCI) 613 (M+H$^+$, 100%).

c) [1S-[1α,2β,3β,4α(trans)]]-2,3-Dihydroxy-4-[5-[[4-(trifluoromethyl)phenyl]thio]-7-[(2-phenylcyclopropyl)amino]-3H-1,2,3-triazolo[4,5-d]pyrimidin-3-yl]-cyclopentanecarboxylic acid Prepared according to the method of example 1, step i) using the product of step b).

MS (APCI) 573 (M+H$^+$, 100%); NMR δH (d$_6$-DMSO) 9.44 (1H, d), 7.89–7.59 (4H, m), 7.29–7.06 (5H, m), 5.16 (1H, br s), 4.96 (1H, q), 4.34 (1H,br s), 4.15 (1H, t), 3.12–3.00 (1H, m), 2.84–2.77 (1H, m), 2.46–2.40 (1H, m), 2.30–2.20 (2H, m), 1.42–1.35 (1H, m), 1.18–1.07 (1H, m).

EXAMPLE 54

[1S-(1α,2β,3β,4α)]-4-[7-(Butylamino)-5-(cyclopentylthio)-3H-1,2,3-triazolo[4,5-d]pyrimidin-3-yl]-2,3-dihydroxy-cyclopentanecarboxylic acid Prepared according to the method of example 11, step b) using the product of example 13, step a) and cyclopentanethiol, followed by the method of example 1, step i.

MS (APCI) 437 (M+H$^+$, 100%); NMR δH (d$_6$-DMSO) 8.95 and 8.60 (1H, t), 5.00 (1H, m), 4.41 (1H, m), 4.22 (1H, m), 3.98 (1H, m), 3.48 and 3.89 (2H, q), 3.32 (2H, br, s), 2.81 (1H, td), 2.5–2.3 (2H, m), 2.19 (2H, m), 1.63 (8H, m), 1.34 (2H, sextet). 0.91 (3H, t)

EXAMPLE 55

[1S-(1α,2β,3β,4α)]-2,3-Dihydroxy-4-[7-[(3-methylbutyl)amino]-5-(Propylthio)-3H-1,2,3-triazolo[4,5-d]pyrimidin-3-yl]-cyclopentanecarboxylic acid a) [3aR-(3aα,4α,6α,6aα)]-tetrahydro-2,2-dimethyl-6-[7-[(3-methylbutyl)amino]-5-(propylthio)-3H-1,2,3-triazolo[4,5-d]pyrimidin-3-yl]-4H-cyclopenta-1,3-dioxole-4-carboxylic acid Prepared according to the method of example 1, step g) using the product of example 1, step f) and (3-methylbutyl)amine.

MS (APCI) 465 (M+H$^+$, 100%); NMR δH (d$_6$-DMSO) 7.95 (1H, d), 5.72 (1H, m), 5.58 (1H, m), 5.12 (1H, d), 3.36–3.01 (2H, m), 3.02–2.88 (2H, m), 2.60–2.46 (1H, m), 1.88–1.78 (2H, m), 1.56 (3H, s), 1.45 (3H), s), 1.10 (3H, t), 0.75 (2H, t), 0.38 (2H, br s).

b) (1α,2β,3β,4α)]-2,3-Dihydroxy-4-[7-[(3-Methylbutyl)amino]-5-(propylthio)-3H-1,2,3-triazolo[4,5-d]pyrimidin-3-yl]-cyclopentanecarboxylic acid Prepared according to the method of example 1, step i) using the product from step a).

MS (APCI) 425 (M+H$^+$, 100%); NMR δH (d$_6$-DMSO) 12.43 (1H, s), 8.73(1H, t), 5.16–5.19 (2H, m), 5.00 (1H, q), 4.70–4.30 (1H, m), 4.22 (1H, t), 3.49–3.96 (2H, m), 3.06–3.12 (2H, m), 2.79–2.82 (1H, m), 2.46–2.32 (2H, m), 1.62–1.73 (3H, m), 1.48–1.54 (2H, m), 0.99 (3H, t), 0.94 (6H, d).

EXAMPLE 56

[1S-[1α,2β,3β,4α(1R*,2S*)]]-2,3-Dihydroxy-4-[7-[(2-phenylcyclopropyl)amino]-5-(propylthio)-3H-1,2,3-triazolo[4,5-d]pyrimidin-3-yl]-cyclopentanecarboxylic acid a) [3aR-[3aα,4α,6α(1S*,2R*),6aα]]-Tetrahydro-2,2-dimethyl-6-[7-[(2-phenylcyclopropyl)amino)]-5-(propylthio)-3H-1,2,3-triazolo[4,5-d]pyrimidin-3-yl]-4H-cyclopenta-1,3-dioxole-4-carboxylic acid A mixture of the product of example 1, step f) (1.0 g), (1S-trans)-2-phenylcyclopropylamine[R-(R*,R*)]-2,3-dihydroxybutanedioate (1:1) (prepared as described by L. A. Mitscher et al., J. Med. Chem. 1986, 29, 2044) (680 mg) and diisopropylethylamine (1.68 ml) in dichloromethane (30 ml)

was stirred at room temperature for 3 days. The reaction mixture was concentrated and the residue purified (SiO$_2$, dichloromethane:methanol:acetic acid 1650:150:1 as eluant) to afford the subtitle compound (862 mg).

MS (APCI) 511 (M+H$^+$, 100%).

b) [1S-[1α,2β,3β,4α(1R*,2S*)]]-2,3-Dihydroxy-4-[7-[(2-phenylcyclopropyl)amino]-5-(propylthio)-3H-1,2,3-triazolo[4,5-d]pyrimidin-3-yl]-cyclopentanecarboxylic acid Prepared according to the method of example 1, step i) using the product of step a).

MS (APCI) 471 (M+H$^+$, 100%); NMR δH (d$_6$-DMSO) 12.42 (1H, br s), 9.34 and 8.98 (1H, d), 7.31–7.15 (5H, m), 5.02 (1H, m), 4.40 (1H, m), 4.22 (1H, m), 3.19 (1H, m), 3.16–2.75 (3H, m), 2.50–2.08 (3H, m), 1.75–1.22 (4H, m), 0.82 and 0.98 (3H, t)

EXAMPLE 57

[1S-[1α(R*),2β,3β,4α]]-N-(3-Amino-3-oxo-2-propyl)-4-[7-(butylamino)-5-(propylthio)-3H-1,2,3-triazolo[4,5-d]pyrimidin-3-yl]-2,3-dihydroxy-cyclopentylcarboxamide a) [3aR-[3aα,4α(S*),6α,6aα]]-N-(3-Amino-3-oxo-2-propyl)-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole-4-carboxamide Prepared according to the method of example 20, step a), using the product of example 1, step g) and (2S)-2-amino-propanamide, hydrobromide.

MS (APCI) 521 (M+H$^+$, 100%).

b) [1S-[1α(R*),2β,3β,4α]]-N-(3-Amino-3-oxo-2-propyl)-4-[7-(butylamino)-5-(propylthio)-3H-1,2,3-triazolo[4,5-d]pyrimidin-3-yl]-2,3-dihydroxy-cyclopentylcarboxamide.

Prepared according to the method of example 1, step i) using the product of step a).

NMR δH (d$_6$-DMSO) 8.99 (1H, t), 8.04 (1H, d), 7.31 (1H, s), 7.03 (1H, s), 4.97 (1H, q), 4.40 (1H, t), 4.25 (1H, m), 4.12 (1H, t), 3.50 (2H, q), 3.09 (2H, m), 2.87 (1H, m), 2.27 (2H, m), 1.69 (2H, m), 1.60 (2H, m), 1.36 (2H, m), 1.19 (2H, d), 0.99 (3H, t), 0.91 (3H, t).

EXAMPLE 58

[1S-[1α(R*),2β,3β,4α]]-3-[7-(Butylamnino)-5-(propylthio)-3H-1,2,3-triazolo[4,5-d]pyrimidin-3-yl]-2,3-dihydroxy-N-[3-hydroxy-1-(methylamino)-1-oxo-2-propyl]-cyclopentanecarboxamide Prepared according to the method of example 20, step a) using the product of example 1, step g) and (2S)-2-amino-3-hydroxy-N-methyl-propanamide, hydrochloride (prepared as described by Zahn, H. Reinert, G , Hoppe-Seyler, Z-Physiol.Chem, 1968, 349, 608) followed by the method of example 1, step i).

NMR δH (d$_6$-DMSO) 8.98 (1H, t), 7.93 (1H, d), 7.80 (1H, d), 5.17 (1H, d), 5.07 (1H, d), 4.97 (1H, m), 4.88 (1H, t), 4.45 (1H, m), 4.28 (1H, m), 4.17 (1H, m), 3.53 (4H, m), 3.10 (2H, m), 2.93 (1H, m), 2.61 (3H, d), 2.24–2.37 (2H, m), 1.73 (2H, m), 1.64 (2H, m), 1.64 (2H, m), 1.35 (2H, m), 0.98 (3H, t), 0.90 (3H, t).

EXAMPLE 59

[1S-(1α,2β,3β,4α)]-4-[7-(Butylamino)-5-(propylthio)-3H-1,2,3-triazo[4,5-d]pyrimidin-3-yl]-2,3-dihydroxy-N-[3-(dimethylamino)-3-oxo-propyl]-cyclopentanecarboxamide a) [3aR-(3aα,4α,6α,6aα)]-N-[6-[7-(Butylamino)-5-(propylthio)-3H-1,2,3-triazo[4,5-d]pyrimidin-3-yl]-tetrahydro-2,2-dimethyl-4H-cyclopenta-1,3-dioxol-4-ylcarbonyl]-β-alanine, 1,1-dimethylethyl ester N,N-Diisopropylethylamine (0.37 ml) was added to a solution of β-alanine, 1,1-dimethylethyl ester, hydrochloride (0.20 g), benzotriazole-1-yl-oxy-tris-(dimethylamino)-phosphoniumhexafluorophosphate (0.49 g) and the product of example 1, step g) (0.45 g) in THF (10 ml). The reaction mixture was stirred at room temperature for 3 hours then concentrated. The residue was taken into ethyl acetate and washed with saturated aqueous sodium bicarbonate solution then dried and concentrated. Purification (SiO$_2$, dichloromethane:methanol 197:3 as eluant) gave the subtitle compound (0.45 g).

MS (APCI) 578 (M+H$^+$, 100%).

b) [1S-(1α,2β,3β,4α)]-N-[[4-[7-(Butylamino)-5-(propylthio)-3H-1,2,3-triazolo[4,5-d] pyrimidin-3-yl]-2,3-dihydroxy-cyclopent-1-yl]carbonyl]-β-alanine Prepared according to the method of example 1, step i) using the product of step a).

MS (APCI) 482 (M+H$^+$, 100%).

c) [1S-(1α,2β,3β,4α)]4-[7-(Butylamino)-5-(propylthio)-3H-1,2,3-triazolo[4,5-d]pyrimidin-3-yl]-2,3-dihydroxy-N-[3-(dimethylamino)-3-oxo-propyl]-cyclopentanecarboxamide Prepared according to the method of step a) using the product of step b) and dimethylamine hydrochloride.

MS (FAB) 509 (M+H$^+$, 100%); NMR δH (d$_6$-DMSO) 0.91 (3H, t), 0.99 (3H, t), 1.31–1.37 (2H, m), 1.58–1.73 (4H, m), 2.24–2.31 (2H, m), 2.69–2.73 (2H, m), 2.74–2.76 (1H, m), 2.81 (3H, s), 2.94 (3H, s), 3.07–3.12 (2H, m), 3.25–3.33 (2H, m), 3.47–3.50 (2H, m), 4.084.11 (1H, m), 4.40–4.42 (1H, m), 4.93–5.20 (3H, m), 7.93 (1H, t), 8.99 (1H, t).

EXAMPLE 60

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-(dimethylamino)-2-oxo-ethyl)-cyclopentanecarboxamide a) [3aR-(3aα,4α,6α,6aα)]-N-[[6-[7-(Butylamino)-5-(propylthio)-3H-1,2,3-triazolo[4,5-d]pyrimidin-3-yl]-tetrahydro-2,2-dimethyl-4N-cyclopenta-1,3-dioxol-4-yl]carbonyl]-glycine, 1,1-dimethylethyl ester Prepared according to the method of example 59, step a) using the product of example 1, step g) and glycine, 1,1-dimethylethyl ester, hydrochloride.

MS (APCI) 564 (M+H$^+$, 100%).

b) [1S-(1α,2β,3β,4α)]-N-[[4-[7-(Butylamino)-5-(propylthio)-3H-1,2,3-triazolo[4,5-d] pyrimidin-3-yl]-2,3-dihydroxy-cyclopent-1-yl]carbonyl]-glycine Prepared according to the method of example 1, step i) using the product of step a).

MS (APCI) 468 (M+H$^+$, 100%).

c) [1S-(1α,2β,3β,4α)]-4-[7-(Butylamino)-5-(propylthio)-3H-1,2,3-triazolo[4,5-d]pyrimidin-3-yl]-2,3-dihydroxy-N-[2-(dimethylamino)-2-oxo-ethyl)-cyclopentanecarboxamide Prepared according to the method of example 59, step a) using the product of step b) and dimethylamine hydrochloride.

MS (FAB) 495 (M+H$^+$, 100%); NMR δH (d$_6$-DMSO) 0.90 (3H, t), 1.01 (3H, t), 1.30–1.38 (2H, m), 1.57–1.73 (4H, m), 2.23–2.38 (2H, m), 2.83 (3H, s), 2.86–2.92 (1H, m), 2.95 (3H, s), 3.06–3.12 (2H, m), 3.46–3.52 (2H, m), 3.94–3.96 (2H, m), 4.13 (1H, m), 4.95–5.14 (3H, m), 7.98 (1H, t), 8.98 (1H, t).

EXAMPLE 61

[1S-(1α,2β,3β,4α)]-4-[7-(Butylamino)-5-(propylthio)-3H-1,2,3-triazolo[4,5-d] pyrimidin-3-yl]-2,3-dihydroxy-N-[3-oxo-3-[(phenylmethyl)amino]-propyl]-cyclopentanecarboxamide Prepared according to the method of example 59, step a) using the product of example 59, step b) and benzylamine.

MS (APCI) 571 (M+H$^+$, 100%); NMR δH (d$_6$-DMSO) 0.91 (3H, t), 0.99 (3H, t), 1.32–1.37 (2H, m), 1.58–1.73 (4H, m), 2.15–2.34 (4H, m), 2.72–2.78 (1H, m), 3.07–3.12 (2H, m), 3.49–3.50 (2H, m), 4.11–4.12 (1H, m), 4.24–4.28 (2H, m), 4.42–4.44 (1H, m), 4.93–4.98 (2H, m), 5.12–5.14(1H, m), 7.19–7.29 (5H, m), 8.01 (1H, t), 8.39 (1H, t), 8.99 (1H, t).

EXAMPLE 62

[1S-(1α,2β,3β,4α)]-4-[7-(Butylamino)-5-(propylthio)-3H-1,2,3-triazolo[4,5-d] pyrimidin-3-yl]-2,3-dihydroxy-N-[2-(methylamino)-2-oxo-ethyl)-cyclopentanecarboxamide Prepared according to the method of example 59, step a) using the product of example 60 step b) and methylamine hydrochloride.

MS (APCI) 481 (M+H$^+$, 100%); NMR δH (d$_6$-DMSO) 0.88–1.00 (6H, m), 1.30–1.38 (2H, m), 1.57–1.73 (4H, m), 2.26–2.38 (3H, m), 2.59 (2H, d), 2.86–2.87 (1H, m), 3.06–3.12 (2H, m), 3.46–3.52 (2H, m), 3.68 (2H, d), 4.13 (1H, t), 4.38–4.42 (1H, m), 4.94–5.00 (2H, m), 7.75 (2H, d), 8.14 (1H, t), 8.98 (1H, t).

EXAMPLE 63

[1S-(1α(R*),2β,3β,4α)]-N-[4-Amino-1-(aminocarbonyl)-4-oxo-butyl]4-[7-(butylamino)-5-(propylthio)-3H-1,2,3-triazolo[4,5-d]pyrimidin-3yl]-2,3-dihydroxy-cyclopentanecarboxamide a)[3aR-(3aα,4α(S*),6α,6aα)]-N-[4-Amino-1-(aminocarbonyl)-4-oxo-butyl]-6-[7-(butylamino)-5-(propylthio)-3H-1,2,3-triazolo[4,5-d]pyrimidin-3-yl]-tetrahydro-2,2-dimethyl-4H-cyclopenta-1,3-dioxole]-cyclopentanecarboxamide.

Sieber amide resin (1.0 g) was washed sequentially with a solution of piperidine in dimethylformamide (20%; 10 ml), N,N-dimethylformamide (DMF) (3×10 ml) and dichloromethane (3×10 ml). To the resin was added a solution of N-α-(9-fluorenylmethoxycarbonyl)-L-glutamine (0.37 g) in DMF (10 ml), followed by N,N'-diisopropylcarbodiimide (0.16 ml) and the mixture stirred for 4 hours. The mixture was filtered and the residue washed sequentially with dichloromethane (3×10 ml), DMF (3×10 ml), a solution of piperidine in DMF (20%, 10 ml), DMF (3×10 ml) and dichloromethane (3×10 ml). The resin was suspended in dichloromethane (5 ml) and treated with the product of example 1, step g) (0.30 g) and N,N'-diisopropylcarbodiimide (0.16 ml). After stirring for 16 hours the resin was washed with dichloromethane (3×10 ml) then trifluoroacetic acid in dichloromethane (2%, 3×10 ml). The combined washings were concentrated and the residue purified by chromatography (HPLC, Nova-pak® C18 column, 0.1% aqueous ammonium acetate:acetonitrile, gradient elution 40:60 to 60:40 over 12 minutes) to afford the subtitle compound (0.05 g).

MS (APCI) 578 (M+H$^+$, 100%)

b) [1S-(1α(R*),2β,3β,4α)]-N-[4-Amino-1-(aminocarbonyl)-4-oxo-butyl]-4-[7-(butylamino)-5-(propylthio)-3H-1,2,3-triazolo[4,5-d]pyrimidin-3yl]-2,3-dihydroxy-cyclopentanecarboxamide.

Prepared according to the method of example 1, step i) using the product of step a).

NMR δH (d$_6$-DMSO) 9.00 (1H, t), 8.03 (1H, d), 7.34 (1H, s), 7.25 (1H, s), 7.08 (1H, s), 6.73 (1H, s), 4.97 (1H, q), 4.40 (1H, t), 4.14 (1H, t), 3.51 (2H, q), 3.10 (2H, m), 2.91 (1H, m), 2.38 (1H, m), 2.21 (1H, m), 2.06 (2H, t), 1.88 (1H, m), 1.69 (3H, m), 1.60 (2H, m), 1.36 (2H, m), 0.99 (3H, t), 0.91 (3H, t).

EXAMPLE 64

[1S-(1α,2β,3β,4α)]-N-[4-Amino-1-[(methylamino) carbonyl]-4-oxo-butyl]4-[7-(butylamino)-5-(propylthio)-3H-1,2,3-triazolo[4,5-d]pyrimidin-3-yl]-2,3-dihydroxy-cyclopentanecarboxamide a) (2S)-5-Amino-N-methyl-2-[[(1,1-dimethylethoxy)carbonyl]amino]-5-oxo-propanamide Prepared according to the method of example 20, step a) using N-2-[(1,1-dimethylethoxy)carbonyl]-L-glutamine and methylamine hydrochloride.

MS (APCI) 258 (M–H$^+$),184 (100%)

b) (4S)-4-Amino-5-(methylamino)-5-oxo-pentanamide hydrochloride

A solution of the product from step a) (0.52 g) in 4M hydrogen chloride/1,4-dioxane (10 ml) was stirred at room temperature for 2 hours. The reaction mixture was concentrated and the residue purified by reverse phase chromatography (Preparative C18 125 Å bulk packing material, water: methanol, gradient elution 0:100 to 100:0) to afford the sub-title compound (0.36 g).

NMR δH (d$_6$-DMSO) 1.82–2.01 (2H, m), 2.14–2.19 (2H, m), 2.65 (3H, d), 3.74–3.76 (1H, m), 6.90 (1H , s), 7.48 (1H, s), 8.34 (1H, s), 8.60 (1H, q).

c) [3aR-(3aα,4α(S*),6α,6aα)]-N-[4-Amino-1-(1-methylamino)carbonyl-4-oxobutyl]-6-[7-(butylamino)-5-(propylthio)-3H-1,2,3-triazolopyrimidin-3-yl]-tetrahydro-2,2-dimethyl-4H-cyclopenta-1,3-dioxol-4-yl-carboxamide Prepared according to the method of example 20, step a) using the product of step b) and the product of example 1, step g).

MS (APCI) 592 (M+H$^+$, 100%).

d) [1S-(1α,2β,3β,4α)]-N-[4-Amino-1-[(methylamino)carbonyl]-4-oxo-butyl]4-[7-(butylamino)-5-(propylthio)-3H-1,2,3-triazolo[4,5-d]pyrimidin-3-yl]-2,3-dihydroxy-cyclopentanecarboxamnide Prepared according to the method of example 1, step i) using the product of step c).

MS (APCI) 552 (M+H$^+$, 100%); NMR δH (d$_6$-DMSO) 0.91 (3H,t), 0.98 (3H,t), 1.36 (2H,sex), 1.62 (2H,quin), 1.69 (2H, sex), 1.66–1.74 (1H, m), 1.80–1.95 (1H, m), 2.03 (2H, t), 2.15–2.25 (1H, m), 2.30–2.40 (1H, m), 2.60 (3H, d), 2.89–2.90 (1H, m), 3.06–3.18 2H, m), 3. (2H, q), 4.12–4.16 (1H, m), 4.19–4.21 (1H, m), 4.39–4.42 (1H, m), 4.90–5.00 (1H, m), 5.03 (1H, d), 5.15 (1H, d), 6.71 (1H, s), 7.23 (1H, s), 7.85 (1H, q), 8.07 (1H, d), 8.99 (1H, t).

EXAMPLE 65

[1S-(1α(R*),2β,3β,4α)]-N-[1-(Aminocarbonyl)-3-hydroxy-propyl)-4-[7-(butylamino)-5-(propylthio)-3H-1,2,3-triazolo[4,5-d]pyrimidin-3-yl]-2,3-dihydroxy-cyclopentanecarboxamide Prepared according to the method of example 59, step a) using the product of example 2 and (2S)-2-amino-4-hydroxy-butanamide (prepared as described by R. M. Khomutov et al, Chem. Abs., 58, 13944)

MS (APCI) 511 (M+H$^+$, 100%); NMR δH (d$_6$-DMSO) 8.99 (1H, t), 8.02 (1H, d), 7.29 (1H, s), 7.05 (1H, s), 5.16 (1H, d), 5.03 (1H, d), 5.00–4.92 (1H, m), 4.46 (1H, t), 4.43–4.37 (1H, m), 4.33–4.26 (1H, m), 4.18–4.12 (1H, m), 3.50 (2H, q), 3.43–3.37 (2H, m), 3.20–3.02 (2H, m), 2.94–2.87 (1H, m), 2.42–2.32 (1H, m), 2.28–2.15 (1H, m), 1.90–1.79 (1H, m), 1.77–1.55 (5H, m), 1.44–1.29 (2H, m), 0.99 (3H, t), 0.91 (3H, t).

EXAMPLE 66

[1S-(1α(R*),2β,3β,4α)]-N-[1-(Aminocarbonyl)-2-hydroxy-ethyl)-2,3-dihydroxy-4-[7-[(4-phenylbutyl) amino]-5-(propylthio)-3H-1,2,3-triazolo[4,5-d] pyrimidin-3-yl]-cyclopentanecarboxamide a) [3aR-(3aα,4α,6α,6aα)]-Tetrahydro-2,2-dimethyl-6-[7-[(4-phenylbutyl)amino]-5-(propylthio)-3H-1,2,3-triazolo[4, 5-d]pyrimidin-3-yl]4H-cyclopenta-1,3-dioxole-4-carboxylic acid Prepared according to the method of example 1, step g) using the product of example 1, step f) and 4-phenylbutylamine.

MS (APCI) 527 (M+H$^+$, 100%)

b) [3aR-(3aα,4α,6α(S*),6aα)]-N-[1-(Aminocarbonyl)-2-hydroxy-ethyl)-tetrahydro-2,2-dhnethyl-6-[7-[(4-phenylbutyl)amino]-5-(propylthio)-3H-1,2,3-triazolo[4,5-d]pyrimidin-3-yl]-4H-cyclopenta-1,3-dioxole-4-carboxamide Prepared according to the method of example 59, step a) using the product of step a) and (2S)-2-amino-3-hydroxy-propanamide, hydrochloride.

MS (APCI) 613 (M+H$^+$, 100%)

c) [1S-(1α(R*),2β,3β,4α) ]-N-[1-(Aminocarbonyl)-2-hydroxy-ethyl)-2,3-dihydroxy-4-[7-[(4-phenylbutyl)amino]-5-(propylthio)-3H-1,2,3-triazolo[4,5-d]pyrimidin-3-yl]-cyclopentanecarboxamide Prepared according to the method of example 1, step i) using the product from step (b).

MS (APCI) 573 (M+H$^+$, 100%); NMR δH (d$_6$-DMSO) 9.01 (1H, t), 7.88 (1H, d), 7.27–7.13 (7H, m), 5.17 (1H, d), 5.07 (1H, d), 4.97–4.95 (1H, m), 4.87–4.84 (1H, m), 4.39–4.37 (1H, m), 4.26–4.24 (1H, m), 4.15–4.13 (1H, m), 3.60–3.51 (4H, m), 3.10–3.05 (2H, m), 2.93–2.29 (1H, m), 2.61 (2H, m), 2.34 (1H, m), 2.25 (1H, m), 1.71–1.63 (6H, m), 0.98 (3H, t).

EXAMPLE 67

1S-[1α,2β,3β,4α(1S*,2R*)]-N-[(Aminocarbonyl)methyl]-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-(3aα,4α,6α(1R*,2S*),6aα)]-N-[(Aminocarbonyl)methyl]-tetrahydro-2,2-dimethyl-6-[7-[2-(phenylcyclopropyl)amino]-5-(propylthio)-3H-1,2,3-triazolo[4,5-d]pyrimidin-3-yl]-4H-cyclopenta-1,3-dioxole-4-carboxamide Prepared according to the method of example 59, step a) using the product of example 34, step a) and glycinamide hydrochloride.

MS (APCI) 567 (M+H$^+$)

b) 1S-[1α,2β,3β,4α(1S*,2R*)]-N-[(Aminocarbonyl)methyl]-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide Prepared according to the method of example 26, step b) using the product of step a).

MS (APCI) 527 (M+H$^+$); NMR δH (d$_6$-DMSO) 9.31 (1H, d), 8.04 (1H, br t), 7.26–7.11 (6H, m), 7.00 (1H, br s), 5.12 (1H, d), 5.00 (1H, d), 4.94 (1H, m), 4.37 (1H, m), 4.10 (1H, m), 3.63 (2H, m), 3.16 (1H, m), 2.91 (1H, m), 2.81 (2H, m), 2.33–2.18(2H, m), 2.08 (1H, m), 1.47 (1H, m), 1.28 (1H, m), 0.76 (3H, t).

EXAMPLE 68

[1S-(1α(R*),2β,3β,4α)]-N-[(1-Aminocarbonyl)-4-(methylamino)-4-oxo-butyl]-4-[7-(butylamino)-5-(propylthio)-3H-1,2,3-triazolo[4,5-d]pyrimidin-3-yl]-2,3-dihydroxy-cyclopentanecarboxamide a) (2S)-2-Amino-5-(methylamino)-5-oxo-pentanamide N,N-Diisopropylethylamine (2.0 ml) was added to a solution of (4S)-5-amino-4-[[(1,1-dimethylethoxy)carbonyl]amino]-5-oxo-pentanoic acid (0.49 g), bromo-tris-pyrrolidino-phosphonium hexafluorophosphate (1.20 g) and methylamine (0.16 g) in acetonitrile (20 ml). The reaction mixture was stirred at room temperature for 2 hours then concentrated. The residue was taken into 4M HCl in 1,4-dioxane (20 ml), stirred for 4 hours then concentrated. Purification (Preparative C18 125 Å bulk packing material, water:methanol, gradient elution 0:100 to 100:0) gave the sub-title compound (0.48 g).

NMR δH (d$_6$-DMSO) 8.24 (2H, br s), 8.00–7.98 (1H, m), 7.95 (1H, be s), 7.58 (1H, br s), 3.74 (1H, br s), 2.56 (3H, d), 2.26–2.12 (2H, m), 2.10–1.92 (2H, m).

b) [3aR-[3aα,4α(S*),6α,6aα]]-N-[(1-(Aminocarbonyl)-4-(methylamino)-4-oxobutyl]-6-[7-(butylamino)-5-(propylthio)-3H-1,2,3-triazolo[4,5-d]pyrimidin-3-yl]-tetrahydro-2,2-dimethyl-4-cyclopenta-1,3-dioxole4-carboxamide Prepared according to the method of example 20, step a) using the product of step a) and the product of example 1, step g).

MS (APCI) 593 (M+H$^+$, 100%)

c) [1S-(1α(R*),2β,3β,4α)]-N-[(1-Aminocarbonyl)-4-(methylamino)-4-oxo-butyl]4-[7-(butylamlino)-5-(propylthio)-3H-1,2,3-triazolo[4,5-d]pyrimidin-3yl]-2,3-dihydroxy-cyclopentanecarboxamide Prepared according to the method of example 1, step i) using the product from step b).

MS (APCI) 552 (M+H$^+$, 100%); NMR δH (d$_6$-DMSO) 8.99 (1H, t), 8.02 (1H, d), 7.69 (1H, q), 7.33 (1H, s), 7.08 (1H, s), 5.15 (1H, br s), 5.03 (1H, br s), 4.97–4.94 (1H, m), 4.40 (1H, br s), 4.21–4.16 (1H, br s), 4.16–4.14 (1H, br s), 3.49 (2H, q), 3.13–3.06 (2H, m), 2.91–2.89 (1H, m), 2.53 (3H, d), 2.38–2.35 (1H, m), 2.23 (1H, m), 2.06 (2H, t), 1.90–1.89 (1H, m), 1.77–1.66 (1H, m), 1.74 (2H, sextuplet), 1.63 (2H, quint), 1.34 (2H, sextuplet), 0.99 (3H, t), 0.91 (3H, t).

EXAMPLE 69

[1S-(1α,2β,3β,4α)]-2,3-Dihydroxy-4-[7-[(4-phenylbutyl)amino]-5-(propylthio)-3H-1,2,3-triazolo[4,5-d]pyrimidin-3-yl]-cyclopentanecarboxylic acid Prepared according to the method of example 1, step i) using the product of example 66, step a).

MS (APCI) 487 (M+H$^+$); NMR δH (d$_6$-DMSO) 9.00 (1H, t), 7.28–7.12 (5H, m), 5.18–5.14 (1H, m), 5.04–4.95 (1H, m), 4.43–4.37 (1H, m), 4.22–4.21 (1H, m), 3.53–3.51 (1H, m), 3.12–2.99 (2H, m), 2.85–2.78 (1H, m), 2.61 (2H, m), 2.49–2.27 (2H, m), 1.74–1.63 (6H, m), 0.98 (3H, m), 0.98 (3H, t).

EXAMPLE 70

[1S-(1α,2β,3β,4α)]-2,3-Dihydroxy-4-[7-[(1-phenylcyclopropyl)amino]-5-(propylthio)-3H-1,2,3-triazolo[4,5-d]pyrimidin-3-yl]-cyclopentanecarboxylic acid a) [3aR-(3aα,4α,6α,6aα)]-Tetrahydro-2,2-dimethyl-6-[7-[(1-phenylcyclopropyl)amino]-5-(propylthio)-3H-1,2,3-triazolo[4,5-d]pyrimidin-3-yl]-4H-cyclopenta-1,3-dioxole-4-carboxylic acid Prepared according to the method of example 1 step g) using the product of example 1, step f) and 1-phenylcyclopropylamine.

MS (APCI) 511 (M+H$^+$, 100%)

b) [1S-(1α,2β,3β,4α)]-2,3-Dihydroxy-4-[7-[(1-phenylcyclopropyl)amino]-5-(propylthio)-3H-1,2,3-triazolo[4,5-d]pyrimidin-3-yl]-cyclopentanecarboxylic acid Prepared according to the method of example 1, step i) using the product of step a).

MS (APCI) 471 (M+H⁺); NMR δH (d₆-DMSO) 9.79 (1H, s), 7.27–7.13 (5H, m), 5.18 (2H, br s), 5.00 (1H, q), 4.40 (1H, br s), 4.22–4.20 (1H, m), 2.88–2.80 (3H, m), 2.49–2.30 (2H, m), 1.47–1.35 (6H, m), 0.77 (3H, t).

EXAMPLE 71

[1S-(1α,2β,3β,4α)]-4-[7-(Butylamino)-5-(propylthio)-3H-1,2,3-triazolo[4,5-d]pyrimidin-3-yl]-2,3-dihydroxy-N-(2,3-dihydroxypropyl)-cyclopentanecarboxamide Prepared according to the method of example 59, step a) using the product of example 2 and 3-amino-1,2-propanediol.

MS (APCI) 484 (M+H⁺, 100%); NMR δH (d₆-DMSO) 8.98 and 8.60 (1H, t), 7.89 (1H, m), 5.12 (1H, d), 5.00–4.90 (2H, m), 4.76 and 4.75 (1H, d), 4.52 (1H, t), 4.42 (1H, m), 4.12 (1H, m), 3.49 and 3.90 (3H, m), 3.32–3.19 (3H, m), 3.18–2.98 (3H, m), 2.83 (1H, m), 2.40–2.18 (2H, m), 1.71 (2H, sextet), 1.63 (2H, quintet), 1.35 (2H, sextet), 0.99 (3H, t), 0.91 (3H, t).

EXAMPLE 72

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-hydroxy-2-(4-hydroxyphenyl)-ethyl]-cyclopentanecarboxamide Prepared according to the method of example 59, step a) using the product of example 2 and α-(aminomethyl)-4-hydroxybenzylalcohol hydrochloride.

NMR δH (d₆-DMSO) 9.24 (1H, s), 8.98 (1H, t), 7.91 (1H, m), 7.12 (2H, t), 6.70 (2H, m), 5.27 (1H, m), 5.12 (1H, d), 4.51 (1H, m), 4.42 (1H, m), 4.10 (1H, m), 3.51 (2H, q), 3.10 (3H, m), 2.82 (1H, m), 2.30 (1H, m), 2.20 (1H, m), 1.72 (4H, m), 1.36 (2H, m), 0.99 (3H, t), 0.91 (3H, t).

EXAMPLE 73

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-hydroxy-2-(3-hydroxyphenyl)-ethyl]-cyclopentanecarboxamide Prepared according to the method of example 59, step a) using the product of example 2 and α-(aminomethyl)-3-hydroxybenzylalcohol hydrochloride.

NMR δH (d₆-DMSO) 9.27 (1H, s), 8.98 (1H, t), 7.97 (1H, t), 7.08 (1H, m), 6.72 (2, m), 6.62 (1H, d), 5.38 (1H, m), 5.12 (1H, d), 4.95 (2H, m), 4.52 (1H, m),.4.45 (1H, m), 4.12 (1H, m), 3.50 (2H, q), 3.30 (1H, m), 3.09 (3H, m), 2.82 (1H, m), 1.71 (2H, m), 1.60 (2H, m), 1.35 (2H, m), 0.98 (3H, t), 0.90 (3H, t).

EXAMPLE 74

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(4-hydroxy-3-methoxyphenyl)-methyl]-cyclopentanecarboxamide Prepared according to the method of example 59, step a) using the product of example 2 and 4-hydroxy-3-methoxybenzylamine hydrochloride.

NMR δH (d₆-DMSO) 8.81 (1H, s), 8.98 (1H, t), 8.33 (1H, t), 6.83 (1H, d), 6.68 (2H, m), 5.16 (1H, d), 5.00 (1H, d), 4.98 (1H, t), 4.45 (1H, m), 4.20 (3H, m), 3.72 (3H, s), 3.50 (2H, q), 3.09 (2H, m), 2.84 (1H, m), 2.32 (2H, m), 1.70 (2H, m), 1.59 (2H, m), 1.35 (2H, m), 0.97 (3H, t), 0.90 (3H, t).

EXAMPLE 75

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(4-hydroxyphenyl)-methyl]-cyclopentanecarboxamide.

a) 4-Hydroxybenzylamine hydrobromide

4-Methoxybenzylamine (1.00 ml) in 48% HBr aq (10 ml) and heated at reflux for 10 hours. The cooled reaction mixture was filtered to give the sub-title compound (2.25 g).

NMR δH (d₆-DMSO) 9.59 (1H, s), 8.01 (3H, br s), 7.27 (2H, d), 6.80 (2H, d), 3.91 (3H, d).

b) [1S-(1α,2β,3β,4α)]-4-[7-(Butylamino)-5-(propylthio)-3H-1,2,3-triazolo[4,5-d]pyrimidin-3-yl]-2,3-dihydroxy-N-[(4-hydroxyphenyl)-methyl]-cyclopentanecarboxamide.

Prepared according to the method of example 59, step a) using the product of example 2 and product of step a).

NMR δH (d₆-DMSO) 9.26 (1H, s), 8.99 (1H, t), 8.32 (1H, t), 7.08 (2H, d), 6.70 (2H, d), 5.14 (1H, d), 5.00 (1H, d), 4.95 (1H, m), 4.46 (1H, m), 4.19 (3H, m), 3.51 (2H, q), 3.10 (1H, m), 2.83 (1H, m), 2.31 (2H, m), 1.69 (2H, m), 1.60 (2H, m), 1.36 (2H, m), 0.99 (3H, t), 0.91 (3H, t).

EXAMPLE 76

[1S-[1α,2β,3β,4α(1R*,2S*)]]-2,3-Dihydroxy-N-(2-hydroxyethyl)-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1S*,2R*),6aα]]-Tetrahydro-N-(2-hydroxyethyl)-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide Prepared according to the method of example 20, step a) using the product of example 56, step a).

MS (APCI) 554 (M+H⁺, 100%).

b) [1S-[1α,2β,3β,4α(1R*,2S*)]]-2,3-Dihydroxy-N-(2-hydroxyethyl)-4-[7-[(2-phenylcyclopropyl)amino]-5-(propylthio)-3H-1,2,3-triazolo[4,5-d]pyrimidin-3-yl]-cyclopentanecarboxamide Prepared according to the method of example 1, step i) using the product of step a).

MS (APCI) 514 (M+H⁺, 100%); NMR δH (d₆-DMSO) 9.35 and 8.96 (1H, m), 8.02 (1H, t), 7.31–7.15 (5H, m), 5.29 (2H, br s), 4.96 (1H, m), 4.78 (1H, br s), 4.41 (1H, m), 4.10 (1H, m), 3.42 (2H, m), 3.25–2.74 and 3.82 (6H, m), 2.40–2.10 (3H, m), 1.80–1.28 (4H, m), 0.81 and 0.99 (3H, t).

EXAMPLE 77

[1S-[1α,2β,3β,4α(1S*,2R*)]]-2,3-Dihydroxy-N-(2-hydroxyethyl)-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-Tetrahydro-N-(2-hydroxyethyl)-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide Prepared according to the method of example 20, step a) using the product of example 34, step a).

MS (APCI) 554 (M+H⁺, 100%).

b) [1S-[1α,2β,3β,4α(1S*,2R*)]]-2,3-Dihydroxy-N-(2-hydroxyethyl)-4-[7-(2-phenylcyclopropylamino)-5-(propylthio)-3H-1,2,3-triazolo[4,5-d]pyrimidin-3-yl]-cyclopentanecarboxamide Prepared according to the method of example 1, step i) using the product of step a).

MS (APCI) 514 (M+H+, 100%); NMR δH (d$_6$-DMSO) 9.35 and 8.95 (1H, d), 7.92 (1H, t), 7.31–7.15 (5H, m), 5.12 (1H, d) 5.00–4.92 (2H, m), 4.67 (1H, t), 4.43 (1H, m), 4.10 (1H, q), 3.41 (2H, q), 3.21–3.12 and 3.85 (3H, m), 3.01–2.72 (3H, m), 2.40–2.10 (3H, m), 1.77–1.42 (3H, m), 1.32 (1H, m), 0.81 and 0.99 (3H, t)

EXAMPLE 78

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(2-hydroxy-5-nitrophenyl)methyl]-cyclopentanecarboxamide a) [3aR-(3aα,4α,6α,6aα)]-6-[7-(Butylamino)-5-(propylthio)-3H-1,2,3-triazolo[4,5-]pyrimidin-3yl]-tetrahydro-N-[(2-hydroxy-5-nitrophenyl)methyl]-2,2-dimethyl-4H-cyclopenta-1,3-dioxole-4-carboxamide Prepared according to the method of example 59, step a) using the product of example 1, step g) and 2-(aminomethyl)-4-nitrophenol.

MS (APCI) 601 (M+H+, 100%).

b) [1S-(1α,2β,3β,4α)]-4-[7-(Butylamino)-5-(propylthio)-3H-1,2,3-triazolo[4,5-d]pyrimidin-3-yl]-2,3-dihydroxy-N-[(2-hydroxy-5-nitrophenyl)methyl]-cyclopentanecarboxamide Prepared according to the method of example 1 step i) using the product of step a).

MS (APCI) 561 (M+H+, 100%); NMR δH (d$_6$-DMSO) 0.88–0.98 (6H, m), 1.31–1.38 (2H, m), 1.57–1.71 (4H, m), 2.27–2.41 (2H, m), 2.90–2.93 (1H, m), 3.04–3.10 (2H, m), 3.46–3.52 (1H, m), 4.17–4.18 (1H, m), 4.27–4.29 (2H, m), 4.42–4.46 (1H, m), 4.97–5.06 (2H, m), 5.19 (1H, d), 6.95–6.99 (1H, m), 8.03–8.06 (2H, m), 8.54 (1H, t), 8.99 (1H, t).

EXAMPLE 79

[1S-[1α,2β,3β,4α(trans)]]-2,3-Dihydroxy-N-(2-Hydroxyethyl)-4-[5-[[(4-trifluoromethyl)phenyl]thio]-7-[(2-phenylcyclopropyl)amino]-3H-1,2,3-triazolo[4,5-d]pyrimidin-3-yl]-cyclopentanecarboamide Prepared according to the method of example 20, step a) using the product of example 5.

MS (APCI) 616 (M+H+, 100%); NMR δH (d$_6$-DMSO) 9.44 (1H, d), 7.93–7.60 (4H, m), 7.29–7.06 (5H, m), 5.11 (1H, d), 4.95–4.91 (2H, m), 4.67 (1H, t), 4.38–4.34 (1H, m), 4.04 (1H, q), 3.41 (2H, q), 3.16 (2H, q), 3.08–3.04 (1H, m), 2.80–2.75 (1H, m), 2.35–2.17 (3H, m), 1.41–1.37 (1H, m), 1.13 (1H, q).

EXAMPLE 80

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(3,4-dihydroxyphenyl)methyl]-cyclopentanecarboxamide.

Prepared according to the method of example 20, step a) using the product of example 2 and 3,4-dihydroxybenzylamine hydrochloride.

NMR δH (d$_6$-DMSO) 9.05 (1H, t), 8.75 (1H, br s), 8.29 (1H, br s), 6.65 (2H, m), 6.52 (1H, d), 4.99 (2H, m), 4.47 (1H, m), 4.13 (2H, m), 3.51 (2H, q), 3.32 (2H, s), 3.10 (2H, m), 2.80 (1H, m), 2.30 (2H, m), 1.69 (2H, m), 1.58 (2H, m), 1.36 (2H, m), 0.99 (3H, t), 0.91 (3H, t).

EXAMPLE 81

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(2-hydroxyphenyl)methyl]-cyclopentanecarboxamide.

a) 2-Hydroxyphenylmethylamine, hydrobromide

Prepared according to the method of example 75, step a) using 2-methoxybenzylamine.

NMR δH (d$_6$-DMSO) 9.55 (1H, s), 8.99 (1H, t), 8.36 (1H, t), 7.10 (1H, m), 6.77 (1H, m), 5.16 (1H,d), 5.03 (1H, d), 4.95 (1H, d), 4.42 (1H, m), 4.24 (2H, m), 4.17 (1H, m), 3.90 (2H, q), 3.09 (2H, m), 2.85 (1H, m), 2.35 (2H, m), 1.69 (2H, m), 1.60 (2H, m), 1.36 (3H, m), 0.98 (3H, m), 0.91 (3H, m).

b) [1S-(1α,2β,3β,4α)]-4-[7-(Butylamino)-5-(propylthio)-3H-1,2,3-triazolo[4,5-d]pyrimidin-3-yl]-2,3-dihydroxy-N-[(2-hydroxyphenyl)methyl]-cyclopentanecarboxamide.

Prepared according to the method of example 59, step a) using the product of example 2 and product of step a).

NMR δH (d$_6$-DMSO) 9.55 (1H, s), 8.99 (1H, t), 8.36 (1H, t), 7.10 (2H, d), 6.77 (1H, m), 5.16 (1H, d), 5.03 (1H, d), 4.95 (1H, m), 4.42 (1H, m), 4.17 (3H, m), 3.51 (2H, q), 3.09 (2H, m), 2.85 (1H, m), 2.35 (2H, m), 1.69 (2H, m), 1.60 (2H, m), 1.36 (2H, m), 0.98 (3H, t), 0.91 (3H, t).

EXAMPLE 82

[1S-(1α,2β,3β,4α)]-2,3-Dihydroxy-N-[2-hydroxyethyl]-4-[7-[(4-phenylbutyl)amino]-5-(propylthio)-3H-1,2,3-triazolo[4,5-d]pyrimidin-3-yl]-cyclopentanecarboxamide Prepared according to the method of example 59, step a) using the product of example 66, step a) and ethanolamine, followed by the method of example 1, step i).

MS (APCI) 530 (M+H+); NMR δH (d$_6$-DMSO) 9.01 (1H, t), 7.92–7.90 (1H, m), 7.27–7.15 (5H, m), 5.12 (1H, d), 4.98–4.93 (2H, m), 4.67 (1H, t), 4.43–4.41 (1H, m), 4.10–4.09 (1H, m), 3.53–3.51 (2H, m), 3.43–3.38 (2H, m), 3.17–3.05 (4H, m), 2.78–2.77 (1H, m), 2.63–2.59 (2H, m), 2.24 (2H, m), 1.71–1.63 (6H, m), 0.98 (3H, t).

EXAMPLE 83

[1S-(1α,2β,3β,4α)]-4-[7-(Cyclopropylamino)-5-(propylthio)-3H-1,2,3-triazolo[4,5-d]pyrimidin-3-yl]-2,3-dihydroxy-N-(2-hydroxyethyl)-cyclopentanecarboxamide a) [3aR-(3aα,4α,6α,6aα)]-6-[7-(Cyclopropylamino)-5-(propylthio)-3H-1,2,3-triazolo[4,5-d]pyrimidin-3-yl]-tetrahydro-N-(2-hydroxyethyl)-2,2-dimethyl-4N-cyclopenta-1,3-dioxole-4-carboxamide Prepared according to the method of example 59, step a) using the product of example 3, step a).

MS (APCI) 478 (M+H+).

a) [1S-(1α,2β,3β,4α)]-4-[7-Cyclopropylamino-5-(propylthio)-3H-1,2,3-triazolo[4,5-d]pyrimidin-3-yl]-2,3-dihydroxy-N-(2-hydroxyethyl)-cyclopentanecarboxamide Prepared according to the method of example 1, step i) using the product of step a).

MS (APCI) 438 (M+H+); NMR δH (d$_6$-DMSO) 9.10 (1H, d), 7.93 (1H, t), 5.01–4.90 (1H, m), 4.51–4.40 (1H, m), 4.16–4.11 (1H, m), 3.42 (2H, t), 3.25–3.00 (5H, m), 2.76 (1H, td), 2.39–2.21 (2H, m), 1.80–1.65 (2H, m), 0.98 (3H, t), 0.90–0.65 (4H, m).

EXAMPLE 84

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(3-hydroxyphenyl)methyl]-cyclopentanecarboxamide Prepared according to the method of example 59, step a) using the product of example 2 and 3-hydroxyphenylmethylamine.

MS (APCI) 516 (M+H⁺); NMR δH (d₆-DMSO) 9.28 (1H, s), 8.59 (1H, t), 8.36 (1H, t), 7.05 (1H,t), 6.64–6.51 (3H, m), 5.11 (1H, d), 4.97 (1H,d), 4.94 (1H, m), 4.40 (1H, m), 4.18 (2H,d), 4.12 (1H, m), 3.46 (2H, q), 3.10–3.00 (2H, m), 2.85–2.75 (1H, m), 2.40–2.30 (1H,m), 2.28–2.20 (1H, m), 1.68–1.63 (2H, m), 1.58–1.54 (2H, m), 0.94 (3H, t), 0.87 (3H, t).

EXAMPLE 85

[1S-[1α,2β,3β,4α(1S*,2R*)]]-4-[7-[[2-(4-Chlorophenyl)cyclopropyl]amino]-5-(propylthio)-3H-1,2,3-triazolo[4,5-d]pyrimidin-3-yl]-2,3-dihydroxy-cyclopentanecarboxylic acid a) [1R-[1α(S*),2β]]-N-[2-(4-Chlorophenyl)cyclopropyl]-2-methoxy-2-phenyl-acetamide and [1S-[1α(R*),2β]]-N-[2-(4-Chlorophenyl)cyclopropyl]-2-methoxy-2-phenyl-acetamide Oxalyl chloride (4.00 ml) was added to a solution of (S)-α-methoxyphenylacetic acid (2.00 g) in dichloromethane (100 ml)/DMF (10 ml). The reaction mixture was stirred at room temperature for 4 hours then concentrated and the residue azeotroped with dichloromethane (3×10 ml). The resulting oil was taken into dichloromethane (4 ml) and treated with a solution of ²-(⁴-chlorophenyl) cyclopropylamine (Prepared as described by C Kaiser etal J. Med. Pharm. Bul., 1962, 5, 1243) (1.86 g) in pyridine (8 ml). The reaction mixture was stirred at room temperature for 30 minutes then partitioned between dichloromethane (500 ml) and water (500 ml). The organic phase was dried and concentrated and the residue purified (SiO₂, isohexane:ethyl acetate:acetic acid 66:33:1) to afford [1S-[1α(R*),2β]]-N-[2-(4-Chlorophenyl)cyclopropyl]-2-methoxy-2-phenyl-acetamide (1.23 g)

MS (APCI, negative ionization) 314 (M−H⁺, 100%).

Further elution of the column gave [1R-[1α(S*),2β]]-N-[2-(4-Chlorophenyl)cyclopropyl]-2-methoxy-2-phenyl-acetamide (1.40 g).

MS (APCI, negative ionization) 314 (M−H⁺, 100%).

b) (1R-trans)-2-(4-Chlorophenyl)-cyclopropylamine

A solution of [1R-[1α(S*),2β]]-N-[2-(4-Chlorophenyl) cyclopropyl]-2-methoxy-2-phenyl-acetamide (1.10 g) (prepared as described in step a)) in 1,4-dioxane (20 ml) containing 5M HCl (aq) (40 ml) was heated at reflux for 18 hours. The reaction was concentrated and the residue partitioned between water and diethyl ether. The aqueous phase was treated with 2M aqueous sodium hydroxide solution (100 ml) then extracted with diethyl ether (2×100 ml). The organic phase was concentrated to afford the sub-title compound (0.55 g). Optical rotation −138.3° (c=0.2, methanol).

c) [3aR-[3aα,4α,6α(1(R*,2S*),6α]]-6-[7-[[2-(4-Chlorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step g) using the product of example 1, step f) and the product of step b).

MS (APCI) 547, 545 (M+H⁺), 545 (100%).

d) [1S-[1α,2β,3β,4α(1S*,2R*)]]-4-[7-[[2-(4-Chlorophenyl) cyclopropyl]amino]-5-(propylthio)-3H-1,2,3-triazolo[4,5-d] pyrimidin-3-yl]-2,3-dihydroxy-cyclopentanecarboxylic acid Prepared according to the method of example 1, step i) using the product of step c).

MS (APCI) 507, 505 (M+H⁺), 505 (100%); NMR δH (d₆-DMSO) 9.37 (1H, d), 7.33 (2H, d), 7.22 (2H, d), 5.01 (1H, q), 4.41 (1H, q), 4.22 (1H, t), 3.18–3.15 (1H, m), 2.96–2.90 (1H, m), 2.87–2.80 (2H, m), 2.50–2.45 (1H, m), 2.38–2.30 (1H, m), 2.15–2.11 (1H, m), 1.56–1.47 (3H, m), 1.38–1.33 (1H, m), 0.81 (3H, t).

EXAMPLE 86

[1S-[1α,2β,3β,4α(1S*,2R*)]]-4-[7-[[2-(4-Chlorophenyl)cyclopropyl]amino]-5-(propylthio)-3H-1,2,3-triazolo[4,5-d]pyrimidin-3-yl]-2,3-dihydroxy-cyclopentanecarboxamide Prepared according to the method of example 63, step a) using the product of example 85, step d).

MS (APCI) 506, 504 (M+H⁺), 504 (100%); NMR δH (d₆-DMSO) 9.36 (1H, d), 7.38 (1H, s), 7.34 (2H, d), 7.22 (2H, m), 6.92 (1H, m), 5.14 (1H, d), 5.02–.4.94 (2H, m), 4.42–4.39 (1H, m), 4.13–4.11 (1H, m), 3.19–2.95 (1H, m), 2.92–2.74 (3H, m), 2.35–2.24 (2H, m), 2.15–2.11 (1H, m), 1.57–1.45 (3H, m), 1.38–1.33 (1H, m), 0.81 (3H, t).

EXAMPLE 87

[1S-[1α,2β,3β,4α(1R*,2S*)]]-4-[7-[[2-(4-Chlorophenyl)cyclopropyl]amino]-5-(propylthio)-3H-1,2,3-triazolo[4,5-d]pyrimidin-3-yl]-2,3-dihydroxy-cyclopentanecarboxylic acid a) (1S-trans)-2-(4-Chlorophenyl)cyclopropylamine Prepared according to the method of example 85, step b) using [1S-[1α(R*),2β]]-N-[2-(4-Chlorophenyl) cyclopropyl]-2-methoxy-2-phenyl-acetamide (the product of example 85, step a).

Optical rotation +159.0° (c=0.2, methanol).

b) [3aR-[3aα,4α,6α(1S*,2R*),6aα]]-6-[7-[[2-(4-Chlorophenyl)cyclopropyl]amino]-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step g) using the product of example 1, step f) and the product of step a).

MS (APCI) 547, 545 (M+H⁺), 545 (100%).

b) [1S-[1α,2β,3β,4α(1R*,2S*)]]-4-[7-[[2-(4-Chlorophenyl) cyclopropyl]amino]-5-(propylthio)-3H-1,2,3-triazolo[4,5-d] pyrimidin-3-yl]-2,3-dihydroxy-cyclopentanecarboxylic acid Prepared according to the method of example 1, step i) using the product of step b).

MS (APCI) 507, 505 (M+H⁺), 505 (100%); NMR δH (d₆-DMSO) 12.43 (1h, br s), 9.36 (1H, d), 7.34 (2H, d), 7.23 (2H, d), 5.19–5.16(2H, m), 5.01 (1H, q), 4.43–4.38 (1H, m), 4.23–4.20 (1H, m), 3.18–3.15 (1H, m), 2.92–2.80 (3H, m), 2.50–2.27 (2H, m), 2.15–2.11 (1H, m), 1.56–1.46 (3H, m), 1.38–1.33 (1H, m), 0.81 (3H, t).

EXAMPLE 88

[1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-cyclopentanecarboxylic acid a) 4,6-Dihydroxy-2-(methylthio)-pyrimidine Prepared according to the method of example 1, step a), using iodomethane.

MS (APCI) 159 (M+H⁺, 100%).

b) 4,6-Dihydroxy-2-(methylthio)-5-nitro-pyrimidine

Prepared according to the method of example 1, step b), using the product of step a).

MS (APCI, negative ionization) 202 (M−H⁺, 100%).

c) 4,6-Dichloro-2-(methylthio)-5-nitro-pyrimidine

Prepared according to the method of example 1, step c), using the product of step b).

m. pt. 59° C.

d) (3aS-(3aα,4β,7β,7aα)]-5-[6-Chloro-2-(methylthio)-5-nitro-pyrimidin-4-yl]-tetrahydro-2,2-dimethyl-4,7-methano-1,3-dioxolo[4,5-c]pyridin-6(3aH)-one Prepared according to the method of example 1, step d), using the product of step c).

MS (APCI) 389, 387 (M+H⁺), 387 (100%).

e) [3aR-(3aα,4α,6α,6aα)]-6-[[5-Amino-6-chloro-2-(methylthio)-4-pyrimidinyl]amino]-tetrahydro-2,2-dimethyl-4H-cyclopenta-1,3-dioxole-4-carboxylic acid Prepared according to the method of example 1, step e), using the product of step d).

MS (APCI) 375 (M+H⁺, 100%).

f) [3aR-(3aα,4α,6α,6aα))]-6-[7-Chloro-5-(methylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step f), using the product of step e).

MS (APCI) 388, 386 (M+H⁺), 386 (100%).

g) [3aR-[3aα,4α,6α(R*S*),6aα]]-Tetrahydro-2,2-dimethyl-6-[5-(methylthio)-7-[(2-phenylcyclopropyl)amino]-3H-1,2,3-triazolo[4,5-d]pyrimidin-3-yi]-4H-cyclopenta-1,3-dioxole-4-carboxylic acid Prepared according to the method of example 34, step a) using the product of step f).

MS (APCI) 483 (M+H⁺, 100%).

h) [1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-cyclopentanecarboxylic acid Prepared according to the method of example 1, step i) using the product of step g).

MS (APCI) 443 (M+H⁺, 100%); NMR δH (d₆-DMSO) 7.31–7.15 (5H, m), 5.00 (1H, q), 4.43 (1H, q), 4.19 (1H, t), 3.19 (1H, m), 2.68 (1H, m), 2.37 (1H, m), 2.32 (3H, s), 2.12 (1H, m), 1.87 (2H, s), 1.50 (1H, m), 1.33 (1H, m).

EXAMPLE 89

[1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-cyclopentanecarboxamide a) [3aR-[3aα,4α,6α(R*,S*),6aα]]-Tetrahydro-2,2-dimethyl-6-[5-(methylthio)-7-[(2-phenylcyclopropyl)amino]-3H-1,2,3-triazolo[4,5-d]pyrimidin-3-yl]-4H-cyclopenta-1,2,3-dioxole-4-carboxamide Prepared according to the method of example 1, step h) using the product of example 88, step g).

MS (APCI) 481 (M+H⁺, 100%).

b) [1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-cyclopentanecarboxamide Prepared according to the method of example 1, step i) using the product of step a).

MS (APCI) 442 (M+H⁺, 100%); NMR δH (d₆-DMSO) 9.36 (1H, d), 7.38 (1H, s), 7.31–7.15 (5H, m), 6.92 (1H, d), 5.12 (1H, d), 4.98 (2H, m), 4.41 (1H, q), 4.13 (1H, q), 3.19 (2H, m), 2.76 (2H, m), 2.25 (2H, m), 2.13 (1H, m), 1.50 (1H, m), 1.32 (1H, m).

EXAMPLE 90

[1S-(1α,2β,3β,4α)]-2,3-Dihydroxy 4-[7-[2-(phenylamino)ethylamino]-5-(propylthio)-3H-1,2,3-triazolo[4,5-d]pyrimidin-3-yl]-cyclopentanecarboxylic acid Prepared according to the method of example 1, step g,) using the product of example 1, step f) and 2-(phenylaminoethylamine, followed by the method of example 1, step i).

MS (APCI) 474 (M+H⁺, 100%).

EXAMPLE 91 a) [3aR-(3aα,4α,6α,6aα)]-6-[7-(Butylamino)-5-[(1-methyl)ethylthio]-3H- 1,2,3-triazolo[4,5-d]pyrimidin-3-yl]-tetrahydro-2,2-dimethyl-4H-cyclopenta-1,3-dioxole-4-carboxylic acid Prepared according to the method of example 11, step b), using the product of example 13, step a) and 2-propanethiol.

MS (APCI) 451 (M+H⁺, 100%).

b) [1S-(1α,2β,3β,4α)]-4-[7-(Butylamino)-5-[(1-methyl)ethylthio]-3H-1,2,3-triazolo[4,5-d]pyrimidin-3-yl]-2,3-dihydroxy-cyclopentanecarboxamide Prepared according to the method of example 1, step h), followed by the method of example 1, step i) using the product of step a).

MS (APCI) 410 (M+H⁺, 100%); NMR δH (d₆-DMSO) 8.97 (1H, t), 7.36 (1H, s), 6.91 (1H, s), 5.11 (1H, d), 4.93 (2H, m), 4.39 (1H, m), 4.10 (1H, m), 3,91 (1H, m), 3.50 (2H, m), 2.33 (1H, m), 2.35–2.21 (2H, m), 1.62 (2H, m), 1.39 (8H, m), 0.91 (3H, m).

EXAMPLE 92

[1S-(1α,2β,3β,4α)]-4-[7-[2-(4-Chlorophenyl)-ethylamino]-5-(propylthio)-3H-1,2,3-triazolo[4,5-d]pyrimidin-3-yl]-2,3-dihydroxy-cyclopentanecarboxylic acid a) (3aR-(3aα,4α,6α,6aα)]-6-[7-[2-(4-Chlorophenyl)-ethylaminol-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 1, step g), using the product of example 1, step f) and 2-(4-chlorophenyl)ethylamine.

MS (APCI) 535, 533 (M+H⁺), 533 (100%).

b) [1S-(1α,2β,3β,4α)]-4-[7-[2-(4-Chlorophenyl)-ethylamino]-5-(propylthio)-3H-1,2,3-triazolo[4,5-d]pyrimidin-3-yl]-2,3-dihydroxy-cyclopentanecarboxylic acid Prepared according to the method of example 1, step i), using the product of step a)

(APCI) 495, 493 (M+H⁺), 493 (100%).

EXAMPLE 93

[1S-[1α,2β,3β,4α(E)]]-2,3-Dihydroxy-4-[7-(3-iodo-prop-2-enylamino)-5-(propylthio)-3H-1,2,3-triazolo[4,5-d]pyrimidin-3-yl]-cyclopentanecarboxylic acid a) [3aR-[3aα,4α,6α(E),6aα]]-6-[7-(3-Tributylstannyl-prop-2-enylamino)-5-(propylthio)-3H-1,2,3-triazolo[4,5-d]pyriuddin-3-yl]-tetrahydro-2,2-dimethyl-4H-cyclopenta-1,3-dioxole-4-carboxylic acid Prepared according to the method of example 1, step g), using the product of example 1, step f) and (3-tributylstannyl)-prop-2-enylamine.

NMR δH (CDCl₃) 6.15 (1H, d), 5.92 (1H, d t), 5.65 (1H, m), 5.52 (1H, m), 5.13 (1H, m), 4.39 (1H, m), 3.15 (2H, m), 2.95 (2H, m), 2.60 (1H, m), 1.82 (2H, m), 1.58 (3H, s), 1.62–1.45 (9H, m), 1.39–1.28 (8H, m), 1.91 (3H, t), 1.00–0.81 (15H, m).

b) [3aR-[3aα,4α,6α(E),6aα]]-Tetrahydro-6-[7-(3-iodo-prop-2-enylamino)-5-(propylthio)-3H-1,2,3-triazolo[4,5-d]pyrimidin-3-yl]-2,2-dimethyl-4H-cyclopenta-1,3-dioxole-4-carboxylic acid A solution of iodine (0.18 g) in THF (1 ml) was added to a solution of the product of step a) (0.45 g) in THF (5 ml) at 0C. After 10 minutes the reaction mixture was partitioned between ethyl acetate (50 ml) and 10% sodium metabisulfite (aq) (50 ml). The organic layer was dried and concentrated. Purification (SiO₂, diethyl ether as eluant) gave the subtitle compound (0.21 g).

NMR δH (CDCl₃) 7.94 (1H, t), 6.43 (1H, d t), 6.30 (1H, d), 5.78 (1H, d), 5.70 (1H, d), 5.12 (1H, d), 4.20 (1H, m), 3.56 (1H, m), 3.26–3.01 (4H, m), 2.62 (1H, m), 1.83 (2H, m), 1.65 (3H, s), 1.45 (3H, s), 1.10–0.81 (3H, t).

c) [1S-[1α,2β,3β,4α(E)]]-2,3-Dihydroxy 4-[7-(3-iodo-prop-2-enylamino)-5-(propylthio)-3H-1,2,3-triazolo[4,5-d]pyrimidin-3-yl]-cyclopentanecarboxylic acid Prepared according to the method of example 1, step i), using the product of step b).

MS (APCI) 521 (M+H⁺, 100%); NMR δH (d₆-DMSO) 6.65 (1H, d t), 6.45 (1H, d), 4.98 (1H, q), 4.40 (1H, m), 4.26 (1H, m), 4.08 (2H, d), 3.20–3.00 (2H, m), 2.75–2.65 (1H, m), 2.53–2.22 (2H, m), 1.68 (2H, m), 0.99 (3H, t).

Pharmacological Data

The preparation for the assay of the P$_{2T}$-receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125 G followed by further centrifugation for 15 minutes at 640 G. The supernatant was discarded and the platelet pellet resuspended in modified, Calcium Free Tyrode solution (10 ml) (CFT), composition: NaCl 137 mM, NaHCO₃ 11.9 mM, NaH₂PO₄ 0.4 mM, KCl 2.7 mM, MgCl₂ 1.1 mM, dextrose 5.6 mM, gassed with 95% 02/5% CO₂ and maintained at 37° C. Following addition of a further 300 ng/ml PGI₂, the pooled suspension was centrifuged once more for 15 minutes at 640 G. The supernatant was discarded and the platelets resuspended initially in 10 ml CFT with further CFT added to adjust the final platelet count to 2×10⁵/ml. This final suspension was stored in a 60 ml syringe at 3° C. with air excluded. To allow recovery from PGI₂-inhibition of normal function, platelets were used in aggregation studies no sooner than 2 hours after final resuspension.

In all studies, 3 ml aliquots of platelet suspension were added to tubes containing CaCl₂ solution (60 gl of 50 mM solution with a final concentration of 1 mM). Human fibrinogen (Sigma, F 4883) and 8-sulphophenyltheophylline (8-SPT which was used to block any P₁-agonist activity of compounds) were added to give final concentrations of 0.2 mg/ml (60 μl of 10 mg/ml solution of clottable protein in saline) and 300 nM (10 μl of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an IC₅₀. Compounds of the invention have pIC₅₀ values of more than 5.0

What is claimed is:

1. A compound of formula (I):

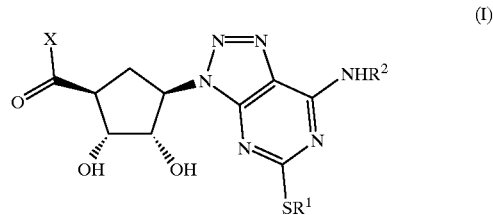

(I)

wherein;

X is OH or NHR³;

R¹ is C₁₋₆-alkyl, C₃₋₈-cycloalkyl or a phenyl group, each group being optionally substituted by one or more halogen atoms and/or OR⁴, NR⁴R⁵, C₁₋₆-thioalkyl and/or C₁₋₆-alkyl (itself optionally substituted by one or more halogen atoms);

R² is C₁₋₈-alkyl or C₂₋₈-alkenyl each of which is optionally substituted by one or more halogen atoms and/or OR⁴, NR⁴R⁵, C₁₋₆-thioalkyl, C₃₋₈-cycloalkyl, aryl and/or C₁₋₆-alkyl groups; or R² is a C₃₋₈-cycloalkyl group optionally substituted by one or more halogen atoms and/or OR⁴, NR⁴R⁵, C₁₋₆-thioalkyl, phenyl and/or C₁₋₆-alkyl groups; the optional phenyl substituent being further optionally substituted by one or more halogen atoms and/or NO₂, C(O)R⁴, OR⁴, NR⁴R⁵, C₁₋₆-thioalkyl and/or C₁₋₆-alkyl groups;

R³ is hydrogen or C₁₋₆-alkyl substituted by one or more hydroxy and/or phenyl groups and optionally by one or more halogen atoms, wherein the phenyl group is substituted by one or more hydroxy groups and optionally substituted by one or more halogen atoms and/or NO₂, C(O)R⁴, OR⁴, NR⁴R⁵, C₁₋₆-thioalkyl and/or C₁₋₆-alkyl groups, or R³ is a C₁₋₆-alkyl group substituted by a C(O)NR⁴R⁵ or a COOH group and optionally by one or more halogen atoms and/or OR⁴, C(NH)NR⁴R⁵, C(O)NR⁴R⁵, phenyl and/or C₁₋₆-alkyl groups, wherein the alkyl group is optionally substituted by one or more hydroxy and/or phenyl groups and wherein the phenyl group is optionally substituted as defined above for R³; or R³ is a lactam ring of formula (i):

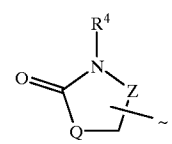

wherein Q is a (CH₂)$_m$ moiety wherein m is 1, 2 or 3, Z is O, C(O) or CH₂;

R⁴ and R⁵ each independently represent hydrogen, phenyl or a C₁₋₆-alkyl wherein the alkyl group is optionally substituted by one or more phenyl groups;

or a salt thereof.

2. A compound according to claim 1 in which R¹ is C₁₋₄-alkyl, C₄₋₈-cycloalkyl or a phenyl group optionally substituted by one or more halogen atoms or by a CF₃ group.

3. A compound according to claim 1 in which $R^2$ is $C_{1-6}$-alkyl optionally substituted by phenyl or $C_{1-6}$-thioalkyl or $R^2$ is a $C_{3-8}$-cycloalkyl group optionally substituted by phenyl.

4. A compound according to claim 1 in which X is OH or $NHR^3$ where $R^3$ is hydrogen or $C_{1-6}$-alkyl substituted by hydroxy and optionally by $C(O)NH_2$ or di-fluoro; $C_{1-6}$-alkyl substituted by $C(O)NH_2$; $C_{1-6}$-alkyl substituted by $C(O)NHMe$; $C_{1-6}$-alkyl substituted by hydroxyphenyl and optionally by $C(O)NR^4R^5$ or $R^3$ is a lactam ring of formula:

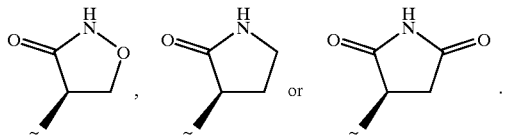

5. A compound according to claim 1, which is

[1S-(1α,2β,3β,4α)]-4-[7-(butylamino)-5-(propylthio)-3H-1,2,3-triazolo[4,5-d]pyrimidin-3-yl]-2,3-dihydroxy-cyclopentanecarboxamide,

[1S-(1α,2β,3β4α)]-4-[7-(butylamino)-5-(propylthio)-3H-1,2,3-triazolo[4,3-d]pyrimidin-3-yl]-2,3-dihydroxy-cyclopentanecarboxylic acid,

[1S(1α,2β,3β,4α)]-4-[7-(cyclopropylamino)-5-(propylthio)-3H-1,2,3-tiazolo[4,5-d]pyrimidin-3-yl]-2,3-dihydroxy-cyclopentanecarboxamide,

[1S-(1α,2β,3β,4α)]-4-[7-(cyclopropylamino)-5-(propylthio)-3H-1,2,3-triazolo[4,5-d]pyrimidin-3-yl]-2,3-dihydroxy-cyclopentanecarboxylic acid,

[1S-[1α,2β,3β,4α(trans)]]-2,3-dihydroxyy-4-[7-[(2-phenylcyclopropyl)amino]-5-(propylthio)-3H-1,2,3-triazolo[4,5-d]pyrimidin-3-yl]-cyclopentanecarboxylic acid,

[1S-[1α,2β,3β,4α(trans)]]-2,3-dihydroxyy-4-[7-[(2-phenylcyclopropyl)-amino]-5-(propylthio)-3H-1,2,3-triazolo[4,5-d]pyrimidin-3-yl]-cyclopentanecarboxamide,

[1S-(1α,2β,3β,4α)]]-2,3-dihydroxy-4-[7-(2-phenylethylamino)-5-(propylthio)-3H-1,2,3-triazolo[4,5-d]pyrimidin-3-yl]-cyclopentanecarboxylic acid,

[1S-(1α,2β,3β,4α)]-2,3-dihydroxy-4-[7-(2-phenylethylamino)-5-(propylthio)-3H-1,2,3-triazolo[4,5-d]pyrimidin-3-yl]-cyclopentanecarboxamide,

[1S-(1α,2β,3β,4α)]-2,3-dihydroxy-4-[7-[2-(methylthio)ethylamino]-5-(propylthio)-3H-1,2,3-triazolo[4,5-d]pyrimidin-3-yl]-cyclopentanecarboxylic acid,

[1S-(1α,2β,3β,4α)]-2,3-dihydroxy-4-[7-[2-(methylthilo)ethylamino]-5-(propylthio)-3H-1,2,3-triazolo[4,5-d]pyrimidin-3-yl]-cyclopentanecarboxamide,

[1S-[1α,2β,3β,4α(trans)]]-4-[5-(Cyclohexylthio)-7-[2-phenylcyclopropyl)amino]-3H-1,2,3-triazolo[4,5-d]pyrimidin-3-yl]-2,3dihydroxy-cyclopentanecarboxylic acid,

[1S-[1α,2β,3β,4α(trans)]]-2,3-Dihydroxy-4-[7-[(2-phenylcyclopropyl)amino]-5-(cyclohexylthio)-3H-1,2,3-triazolo[4,5-d]pyrimidin-3-yl]-cyclopentanecarboxamide,

[1S-(1α,2β,3β,4α)]-4-[7-(Butylamino)-5-(3,4-dichilorophenylthio)-3H-1,2,3-triazolo[4,5-d]pyrimidin-3-yl]-2,3-dihydroxy-cyclopentanecarboxylic acid,

[1S-(1α,2β,3β,4α)]-4-[7-(Butylamino)-5-(3,4-dichlorophenylthio)-3H-1,2,3-triazolo[4,5-d]pyrimidin-3-yl]-2,3-dihydroxy-cyclopentanecarboxamide,

[1S-(1α,2β,3β,4α)]-4-[7-(Butylamino)-5-[4-(trifluoromethyyl)phenylthio]-3H-1,2,3-triazolo[4,5-d]pyrimidin-3-yl]-2,3-dihydroxy-cyclopentanecarboxylic acid, and pharmaceutically acceptable salts thereof.

6. A compound according to claim 1, which is

[1S-(1α,2β,3β,4α)]-4-[7-(Butylamino)-5-[4-(trifluoromethyl)phenylthio]-3H-1,2,3-triazolo[4,5-d]pyrimidin-3-yl]-2,3-dihydroxy-cyclopentanecarboxamide,

[1S-(1α,2β,3β,4α)]-4-[7-(Butylamino)-5-(phenylthio)-3H-1,2,3-triazolo[4,5-d]pyrimidin-3-yl]-2,3-dihydroxy-cyclopentanecarboxylic acid,

[1S-(1α,2β,3β,4α)]-4-[7-(Butylamino)-5-(phenylthio)-3H-1,2,3-triazolo[4,5-d]pyrimidin-3-yl]-2,3-dihydroxy-cyclopentanecarboxamide,

[1S-(1α,2β,3β,4α)]-4-[7-(Cyclopropylamino)-5-(3,4-dichlorophenylthio)-3H-1,2,3-triazolo[4,5-d]pyrimidin-3-yl]-2,3-dihydroxy-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-(2-hydroxyethyl)-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-(3-hydroxy-2,2-difluoropropyl)-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-(4-hydroxyphenyl)ethyl]cyclopentanecarboxamide,

[1S-(1α,2β,3β,4α)]-4-[7-(Butylamino)-5-[4-(trifluoromethyl)phenylthio]-3H-1,2,3-triazolo[4,5-d]pyrimidin-3-yl]-2,3-dihydroxy-N-(2-hydroxyethyl)-cyclopentanecarboxamide,

[1S-(1α,2β,3β,4α)]-N-[1-(Aminocarbonyl)-2-(hydroxy)ethyl]-4-[7-(butylamino)-5-(propylthio)-3H-1,2,3-triazolo[4,5-d]pyrimidin-3-yl]-2,3-dihydroxy-cyclopentanecarboxamide,

[1S-[1α(S*),2β,3β,4α]]-4-[7-(Butylamino)-5-(propylthio)-3H-1,2,3-triazolo[4,5-d]pyrimidin-3-yl]-N-(tetrahydro-3-oxo-isoxazol-4-yl)-2,3-dihydroxy-cyclopentanecarboxamide,

[1S-[1α(R*),2β,3β,4α]]-4-[7-(Butylamino)-5-(propylthio)-3H-1,2,3-triazolo[4,5-d]pyrimidin-3-yl]-2,3-dihydroxy-N-(2-oxo-pyrrolidin-3-yl)-cyclopentanecarboxamide,

[1S-[1α(R*),2β,3β,4α]]-4-[7-(Butylamino)-5-(propylthio)-3H-1,2,3-triazolo[4,5-d]pyrimidin-3-yl]-2,3-dihydroxy-N-(2,3-di-oxo-pyrrolidin-3-yl)-cyclopentanecarboxamide,

[1S-[1α(R*),2β,3β,4α]]-N-[(Aminocarbonyl)-methyl]-4-[7-(butylamino)-5-(propylthio)-3H-1,2,3-triazolo[4,5-d]pyrimidin-3-yl]-2,3-dihydroxy-cyclopentanecarboxamide,

[1S-[1α(R*),2β,3β,4α]]-N-[1-(Aminocarbonyl)-2-(4-hydroxyphenyl)ethyl]-4-[7-(butylamino)-5-(propylthio)-3H-1,2,3-triazolo[4,5-d]pyrimidin-3-yl]-2,3-dihydroxy-cyclopentanecarboxamide, and pharmaceutically acceptable salts thereof.

7. A compound according to claim 1, which is

[1S-[1α(R*),2β,3β,4α]]-N-[1-(Aminocarbonyl)-2-(hydroxyethyl)-4-[7-(butylamino)-5-[4-(trifluoromethyl)phenylthio]-3H-1,2,3-triazolo[4,5-d]pyrimidin-3-yl]-2,3-dihydroxy-cyclopentanecarboxamide,

[1S-[1α(1R*,2S*),2β,3β,4α]]-N-[1-(Amino-carbonyl)-2-(hydroxy)propyl]-4-[7-(butylamino)-5-(propylthio)-3H-1,2,3-triazolo[4,5-d]pyrimidin-3-yl]-2,3-dihydroxycyclopentanecarboxamide,

[1S-[1α,2β,3β,4α]]-N-[2-(Aminocarbonyl)ethyl]-4-[7-(butylamino)-5-(propylthio)-3H-1,2,3-triazolo[4,5-d]pyrimidin-3-yl]-2,3-dihydroxy-cyclopentanecarboxamide,

[1S-[1α,2β,3β,4α]]-4-[7-(Butylamino)-5-(propylthio)-3H-1,2,3-triazolo[4,5-d]pyrimidin-3-yl]-2,3-dihydroxy-N-[2-(methylaminocarbonyl)-ethyl]-cyclopentanecarboxamide,

[1S-[1α,2β,3β,4α(1S*,2R* )]]-2,3-Dihydroxy-4-[7-[(2-phenylcyclopropyl)amino]-5-(propylthio)-3H-1,2,3-triazolo[4,5-d]pyrimidin-3-yl]cyclopentanecarboxylic acid,

[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentanecarboxamide,

[1S-(1α,2β,3β,4α)]-2,3-Dihydroxy-4-[7-(cyclobutylamino)-5-(propylthio)-3H-1,2,3-triazolo[4,5-d]pyrimidin-3-yl]-cyclopentanecarboxylic acid,

[1S-(1α,2β,3β,4α)]-4-[7-(Cyclobutylamino)-5-(propylthio)-3H-1,2,3-triazolo[4,5-d]pyrimidin-3-yl]-2,3-dihydroxy-cyclopentanecarboxamide,

[1S-(1α,2β,3β,4α)]-4-[7-(Cyclopropylamino)-5-[[4-(trifluomomethyl)phenyl]thio]-3H-1,2,3-triazolo[4,5-d]pyrimidin-3-yl]-2,3-dihydroxy-cyclopentanecarboxylic acid,

[1S-(1α,2β,3β,4α)]-4-[7-(Cyclopropylamino)-5-[[4-(trifluoromethyl)phenyl]thio]-3H-1,2,3-triazolo[4,5-d]pyrimidin-3-yl]-2,3-dihydroxy-cyclopentanecarboxamide,

[1S-(1α,2β,3β,4α)]-4-[7-(Butylamino)-5-[(3,3,3-trifluoropropyl)thio]-3H-1,2,3-triazolo[4,5-d]pyrimidin-3-yl]-2,3-dihydroxy-cyclopentanecarboxylic acid,

[1S-(1α,2β,3β,4α)]-4-[7-(Butylamino)-5-[(3,3,3-trifluoropropyl)thio]-3H-1,2,3-triazolo[4,5-d]pyrimidin-3-yl]-2,3-dihydroxy-cyclopentanecarboxamide,

[1S-(1α,2β,3β,4α)]-2,3-Dihydroxy-4-7-[(1,4-dimethylpentyl)amino]-5-(propylthio)-3H-1,2,3-triazolo[4,5-d]pyrimidin-3-yl]-cyclopentanecarboxylic acid,

[1S-(1α,2β,3β,4α)]-2,3-Dihydroxy-4-[7-[(1,4-dimethylpentyl)amino]-5-(propylthio)-3H-1,2,3-triazolo[4,5-d]pyrimidin-3-yl]cyclopentanecarboxamide,

[1S-(1α,2β,3β,4α)]-2,3-Dihydroxy-4-[7-[(1-methylbutyl)amino]-5-(propylthio)-3H-1,2,3-triazolo[4,5-d]pyrimidin-3-yl]-cyclopentanecarboxylic acid, and pharmaceutically acceptable salts thereof.

8. A compound according to claim 1, which is:

[1S-(1α,2β,3β,4α)]-2,3-Dihydroxy-4-[7-[(1-methylbutyl)amino]-5-(propylthio)-3H-1,2,3-triazolo[4,5-d]pyrimidin-3-yl]-cyclopentanecarboxamide,

[1S-(1α,2β,3β,4α)]-2,3-Dihydroxy-4-[7-[(1,3-dimethylbutyl)amino]-5-(propylthio)-3H-1,2,3-triazolo[4,5-d]pyrimidin-3-yl]-cyclopentanecarboxylic acid,

[1S-(1α,2β,3β,4α)]-2,3-Dihydroxy-4-[7-[(1,3-dimethylbutyl)amino]-5-(propylthio)-3H-1,2,3-triazolo[4,5-d]pyrimidin-3-yl]cyclopentanecarboxamide,

[1S-(1α,2β,3β,4α)]-4-[7-(Ethylamino)-5-(propylthio)-3H-1,2,3-triazolo[4,5-d]pyrimidin-3-yl]-2,3-dihydroxy-cyclopentanecarboxylic acid,

[1S-(1α,2β,3β,4α)]-4-[7-(4-Hydroxybutylamino)-5-(propylthio)-3H-1,2,3-triazolo[4,5-d]pyrimidin-3-yl]-2,3-dihydroxy-cyclopentanecarboxylic acid,

[1S-(1α,2β,3β,4α)]-4-[7-(Cyclopentylamino)-5-(propylthio)-3H-1,2,3-triazolo[4,5-d]pyrimidin-3-yl]-2,3-dihydroxy-cyclopentanecarboxylic acid,

[1S-(1α,2β,3β,4α)]-4-[5-[(4-Bromophenyl)thio]-7-(butylamino)-3H-1,2,3-triazolo[4,5-d]pyrimidin-3-yl]-2,3-dihydroxy-cyclopentanecarboxylic acid,

[1S-(1α,2β,3β,4α)]-4-[7-[(6-Hydroxyhexyl)amino]-5-(propylthio)-3H-1,2,3-triazolo[4,5-d]pyrimidin-3-yl]-2,3-dihydroxy-cyclopentanecarboxylic acid,

[1S-[1α,2β,3β,4α(trans)]]-2,3-Dihydroxy-4-[5-[[4-(trifluoromethyl)phenyl]thio]-7-[(2-phenylcyclopropyl)amino]-3H-1,2,3-triazolo[4,5-d]pyrimidin-3-yl]-cyclopentanecarboxylic acid,

[1S-(1α,2β,3β,4α)]-4-[7-(Butylamino)-5-(cyclopentylthio)-3H-1,2,3-triazolo[4,5-d]pyrimidin-3-yl]-2,3-dihydroxy-cyclopentanecarboxylic acid,

[1S-(1α,2β,3β,4α)]-2,3-Dihydroxy-4-[7-[(3-methylbutyl)amino]-5-(propylthio)-3H-1,2,3-triazolo[4,5-d]pyrimidin-3-yl]-cyclopentanecarboxylic acid,

[1S-[1α,2β,3β,4α(1R*,2S*)]]-2,3-Dihydroxy-4-[7-[(2-phenylcyclopropyl)amino]-5-(propylthio)-3H-1,2,3-triazolo[4,5-d]pyrimidin-3-yl]-cyclopentanecarboxylic acid,

[1S-[1α(R*),2β,3β,4α]]-N-(3-Amino-3-oxo-2-propyl)-4-[7-(butylamino)-5-(propylthio)-3H-1,2,3-triazolo[4,5-d]pyrimidin-3-yl]-2,3-dihydroxy-cyclopentylcarboxamide,

[1S-[1α(R*),2β,3β,4α]]-3-[7-(Butylamino)-5-(propylthio)-3H-1,2,3-triazolo[4,5-d]pyrimidin-3-yl]-2,3-dihydroxy-N-[3-hydroxy-1-(methylamino)-1-oxo-2-propyl]-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-[3-(dimethylamino)-3-oxo-propyl]-cyclopentanecarboxamide, and pharmaceutically acceptable salts thereof.

9. A compound according to claim 1, which is

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-(dimethylamino)-2-oxo-ethyl)-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxyl-N-[3-oxo-3-[(phenylmethyl)amino]-propyl]-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-2-(methylamino)-2-oxo-ethyl)-cyclopentanecarboxamide,

[1S-(1α(R*),2β,3β,4α)]-N-[4-Amino-1-(aminocarbonyl)-4-oxo-butyl]-4-[7-(butylamino)-5-(propylthio)-3H-1,2,3-triazolo[4,5-d]pyrimidin-3yl]-2,3-dihydroxy-cyclopentanecarboxamide,

[1S-(1α,2β,3β,4α)]-N-[4-Amino-1-[(methylamino)carbonyl]-4-oxo-butyl]-4-[7-(butylamino)-5-

(propylthio)-3H-1,2,3-triazolo[4,5-d]pyrimidin-3-yl]-2,3-dihydroxy-cyclopentanecarboxamide,

[1S-(1α(R*),2β,3β,4α)]-N-[1-(Aminocarbonyl)-3-hydroxy-propyl)-4-[7-(butylamino)-5-(propylthio)-3H-1,2,3-triazolo[4,5-d]pyrimidin-3-yl]-2,3-dihydroxy-cyclopentanecarboxamide,

[1S-(1α(R*),2β,3β,4')]-N-[1-(Aminocarbonyl)-2-hydroxy-ethyl)-2,3-dihydroxy-4-[7-[(4-phenylbutyl)amino]-5-(propylthio)-3H-1,2,3-triazolo[4,5-d]pyrimidin-3-yl]-cyclopentanecarboxamide, 1S-[1α,2β,3β,4α(1S*,2R*)]]-N-[(Aminocarbonyl)methyl]-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide,

[1S-(1α(R*),2β,3β,4α)]-N-[(1-Aminocarbonyl)-4-(methylamino)-4-oxo-butyl]-4-[7-(butylamino)-5-(propylthio)-3H-1,2,3-triazolo[4,5-d]pyrimidin-3-yl]-2,3-dihydroxy-cyclopentanecarboxamide,

[1S-(1α,2β,3β,4α)]-2,3-Dihydroxy-4-[7-[(4-phenylbutyl)amino]-5-(propylthio)-3H-1,2,3-triazolo[4,5-d]pyrimidin-3-yl]-cyclopentanecarboxylic acid,

[1S-(1α,2β,3β,4α)]-2,3-Dihydroxy-4-[7-[(1-phenylcyclopropyl)amino]-5-(propylthio)-3H-1,2,3-triazolo[4,5-d]pyrimidin-3-yl]-cyclopentanecarboxylic acid,

[1S-(1α,2β,3β,4α)]-4-[7-(Butylamino)-5-(propylthio)-3H-1,2,3-triazolo[4,5-d]pyrimidin-3-yl]-2,3-dihydroxy-N-(2,3-dihydroxypropyl)-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-[2-hydroxy-2-(4-hydroxyphenyl)ethyl]-cyclopentanecarboxamide,

[1S-(1α,2β,3β,4α)]-4-[7-(Butylamino)-5-propylthio)-3H-1,2,3-triazoio[4,5-d]pyrimidin-3-yl]-2,3-dihydroxy-N-[2-hydroxy-2-(3-hydroxyphenyl)ethyl]-cyclopentanecarboxamide, and pharmaceutically acceptable salts thereof.

10. A compound according to claim 1, which is

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(4-hydroxy-3-methoxyphenyl)-methyl]-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(4-hydroxyphenyl)-methyl]-cycylopentanecarboxamide,

[1S-[1α,2β,3β,4α(1R*,2S*)]]-2,3-Dihydroxy-N-(2-hydroxyethyl)-4-[7-[(2-phenylcyclopropyl)amino]-5-propylthio)-3H-1,2,3-triazolo[4,5-d]pyrimidin-3-yl]-cyclopentanecarboxamide,

[1S-[1α,2β,3β,4α(1S*,2R*)]]-2,3-Dihydroxy-N-(2-hydroxyethyl)-4-[7-[(2-phenylcyclopropyl)amino]-5-propylthio)-3H-1,2,3-triazolo[4,5-d]pyrimidin-3-yl]-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(2-hydroxy-5-nitrophenyl)methyl]-cyclopentanecarboxamide,

[1S-[1α,2β,3β,4α(trans)]]-2,3-Dihydroxy-N-(2-Hydroxyethyl)-4-[5-[[(4-trifluoromethyl)phenyl]thio]-7-[(2-phenylcyclopropyl)amino]-3H-1,2,3-triazolo[4,5-d]pyrimidin-3-y]-cyclopentanecarboaxmide,

[1S-(1α,2β,3β,4α)]-4-[7-(Butylamino)-5-propylthio)-3H-1,2,3-triazolo[4,5-d]pyrimidin-3-yl]-2,3-dihydroxy-N-[(3,4-dihydroxyphenyl)methyl]-cyclopentanecarboxamide,

[1S-(1α,2β,3β,4α)]-4-[7-(Butylamino)-5-(propylthio)-3H-1,2,3-triazolo[4,5-d]pyrimidin-3-yl]-2,3-dihydroxy-N-[(2-hydroxyphenyl)methyl]-cyclopentanecarboxamide,

[1S-(1α,2β,3β,4α)]-2,3-Dihydroxy-N-[2-hydroxyethyl]-4-[7-[(4-phenylbutyl)amino]-5-(propylthio)-3H-1,2,3-triazolo[4,5-d]pyrimidin-3-yl]-cyclopentanecarboxamide,

[1S-(1α,2β,3β,4α)]-4-[7-(Cyclopropylamino)-5-(propylthio)-3H-1,2,3-triazolo[4,5-d]pyrimidin-3-yl]-2,3-dihydroxy-N-(2-hydroxyethyl)-cyclopentanecarboxamide.

11. A pharmaceutical composition comprising a compound according to claim 1 in combination with a pharmaceutically acceptable diluent, adjuvent or carrier.

12. A method for the treatment of unstable angina, coronary angioplasty (PTCA), perithrombolysis, primary arterial thrombotic complications due to interventions in atherosclerotic disease, or thrombotic complications of surgical or mechanical damage, which comprises administering to a patient suffering from such a disorder a therapeutically effective amount of a compound according to claim 1.

13. A process for the preparation of a compound of formula (I) as defined in claim 1 which comprises (a) deprotecting a compound of formula (II):

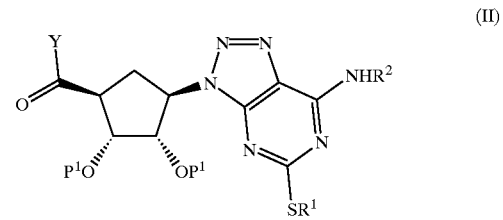

(II)

wherein $R^1$ and $R^2$ are as defined above, $P^1$ is a protecting group and Y is X as defined above or O—$C_{1-6}$-alkyl, O-benzyl or $NHR^7$ wherein $R^7$ is a $C_{1-6}$-alkyl group substituted by a $C(O)OR^8$ group and optionally one or more halogen atoms and/or $OR^4$, $C(NH)NR^4R^5$, $C(O)NR^4R^5$, phenyl and/or $C_{1-6}$-alkyl groups, wherein $R^4$ and $R^5$ are as defined above and $R^8$ is $C_{1-6}$-alkyl or benzyl; and, optionally (b) reacting the compound of formula (I) thus obtained with a suitable acid or base to prepare a pharmaceutically acceptable salt.

14. A compound of formula (II) as defined in claim 13.

* * * * *